United States Patent
Baumann et al.

(10) Patent No.: US 6,645,919 B1
(45) Date of Patent: Nov. 11, 2003

(54) 3-(4,5-DIHYDROISOXAZOL-5-YL) BENZOYLCYCLOHEXENONES AND THE USE THEREOF AS HERBICIDES

(75) Inventors: Ernst Baumann, Dudenhofen (DE); Wolfgang von Deyn, Neustadt (DE); Steffen Kudis, Mannheim (DE); Klaus Langemann, Schauenburg (DE); Guido Mayer, Neustadt (DE); Ulf Misslitz, Neustadt (DE); Ulf Neidlein, Mannheim (DE); Helmut Walter, Obrigheim (DE); Cyrill Zagar, Ludwigshaften (DE); Matthias Witschel, Bad Dürkheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/276,225
(22) PCT Filed: May 11, 2001
(86) PCT No.: PCT/EP01/05390
§ 371 (c)(1), (2), (4) Date: Nov. 14, 2002
(87) PCT Pub. No.: WO01/87856
PCT Pub. Date: Nov. 22, 2001

(30) Foreign Application Priority Data

May 18, 2000 (DE) .......................... 100 24 107

(51) Int. Cl.⁷ ....................... A01N 43/80; C07D 261/04
(52) U.S. Cl. ....................... 504/271; 548/240
(58) Field of Search ........................... 548/240; 504/271

(56) References Cited

U.S. PATENT DOCUMENTS 6,004,903 A * 12/1999 von Deyn et al. .......... 504/239

OTHER PUBLICATIONS

Von Deyn et al, WO 96/26200 Aug. 1996.*

* cited by examiner

Primary Examiner—Robert W. Ramsuer
(74) Attorney, Agent, or Firm—Keil & Weinkauf

(57) ABSTRACT

3-(4,5-Dihydroisoxazol-5-yl)benzoylcyclohexenones of the formula I

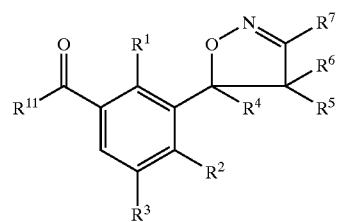

in which the variables have the following meanings:

$R^1$, $R^2$ are hydrogen, nitro, halogen, cyano, alkyl, haloalkyl, alkoxy, haloalkoxy, alkylthio, haloalkylthio, alkylsulfinyl, haloalkylsulfinyl, alkylsulfonyl or $C_1$–$C_6$-haloalkylsulfonyl;

$R^3$ is hydrogen, halogen or alkyl;

$R^4$ is hydrogen or alkyl;

$R^5$, $R^6$ are hydrogen, halogen, cyano, nitro, alkyl, alkoxy, alkylthio, dialkylamino, phenyl, benzyl or carbonyl, it being possible for the 7 last-mentioned radicals to be substituted;

$R^{11}$ is unsubstituted or substituted cyclohexenone which is linked in position 2 and has attached to it in position 1 a hydroxyl radical or derivatives thereof;

and their agriculturally useful salts, processes for the preparation of the 3-(4,5-dihydroisoxazol-5-yl) benzoylcyclohexenones, compositions comprising them, and the use of these derivatives or of compositions comprising them for controlling undesired plants.

16 Claims, No Drawings

3-(4,5-DIHYDROISOXAZOL-5-YL) BENZOYLCYCLOHEXENONES AND THE USE THEREOF AS HERBICIDES

The present invention relates to 3-(4,5-dihydroisoxazol-5-yl)benzoylcyclohexenones of the formula I

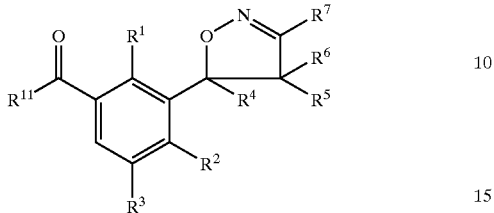

in which the variables have the following meanings:

$R^1$, $R^2$ are hydrogen, nitro, halogen, cyano, $C_1$–$C_6$-alkyl, $C_1$–$C_6$-haloalkyl, $C_1$–$C_6$-alkoxy, $C_1$–$C_6$-haloalkoxy, $C_1$–$C_6$-alkylthio, $C_1$–$C_6$-haloalkylthio, $C_1$–$C_6$-alkylsulfinyl, $C_1$–$C_6$-haloalkylsulfinyl, $C_1$–$C_6$-alkylsulfonyl or $C_1$–$C_6$-haloalkylsulfonyl;

$R^3$ is hydrogen, halogen or $C_1$–$C_6$-alkyl;

$R^4$ is hydrogen or $C_1$–$C_4$-alkyl;

$R^5$, $R^6$ are hydrogen, halogen, cyano, nitro, $C_1$–$C_4$-alkyl, $C_1$–$C_4$-alkoxy-$C_1$–$C_4$-alkyl, di($C_1$–$C_4$-alkoxy)-$C_1$–$C_4$-alkyl, di($C_1$–$C_4$-alkyl)amino-$C_1$–$C_4$-alkyl, di($C_1$–$C_4$-alkyl)aminoimino-$C_1$–$C_4$-alkyl, hydroxyimino-$C_1$–$C_4$-alkyl, $C_1$–$C_6$-alkoxyimino-$C_1$–$C_4$-alkyl, $C_1$–$C_4$-alkoxycarbonyl-$C_1$–$C_4$-alkyl, $C_1$–$C_4$-alkylthio-$C_1$–$C_4$-alkyl, $C_1$–$C_4$-haloalkyl, $C_1$–$C_4$-cyanoalkyl, $C_3$–$C_8$-cycloalkyl, $C_1$–$C_4$-alkoxy, $C_1$–$C_4$-haloalkoxy, $C_1$–$C_4$-alkoxy-$C_2$–$C_4$-alkoxy, $C_1$–$C_4$-haloalkoxy, $C_1$–$C_4$-alkylthio, $C_1$–$C_4$-haloalkylthio, di($C_1$–$C_4$-alkyl)amino, $COR^8$, phenyl or benzyl, it being possible for the two last-mentioned substituents to be partially or fully halogenated and/or to have attached to them one to three of the following groups: nitro, cyano, $C_1$–$C_4$-alkyl, $C_1$–$C_4$-haloalkyl, $C_1$–$C_4$-alkoxy or $C_1$–$C_4$-haloalkoxy; or $R^5$ and $R^6$ together form a $C_2$–$C_6$-alkanediyl chain which can be mono- to tetrasubstituted by $C_1$–$C_4$-alkyl and/or can be interrupted by oxygen or by unsubstituted or $C_1$–$C_4$-alkyl-substituted nitrogen;

$R^7$ is halogen, cyano, hydroxyl, $C_1$–$C_6$-alkyl, $C_1$–$C_6$-haloalkyl, $C_1$–$C_6$-alkoxy, $C_1$–$C_6$-haloalkoxy, $C_1$–$C_6$-alkylthio, $C_1$–$C_6$-haloalkylthio, $C_1$–$C_6$-alkylsulfinyl, $C_1$–$C_6$-haloalkylsulfinyl, $C_1$–$C_6$-alkylsulfonyl, $C_1$–$C_6$-haloalkylsulfonyl, amino, $C_1$–$C_6$-alkylamino, di($C_1$–$C_6$-alkyl)amino, di($C_1$–$C_4$-alkoxy)methyl, hydroxylamino-$C_1$–$C_4$-alkyl, $C_1$–$C_6$-alkoxyimino-$C_1$–$C_4$-alkyl or $COR^8$;

$R^8$ is hydrogen, $C_1$–$C_4$-alkyl, $C_1$–$C_4$-haloalkyl, hydroxyl, $C_1$–$C_4$-alkoxy, $C_1$–$C_4$-alkoxy-$C_2$–$C_4$-alkoxy, $C_1$–$C_4$-haloalkoxy, $C_3$–$C_6$-alkenyloxy, $C_3$–$C_6$-alkynyloxy or $NR^9R^{10}$;

$R^9$ is hydrogen or $C_1$–$C_4$-alkyl;

$R^{10}$ is $C_1$–$C_4$-alkyl;

$R^{11}$ is a cyclohexenone of the formula II

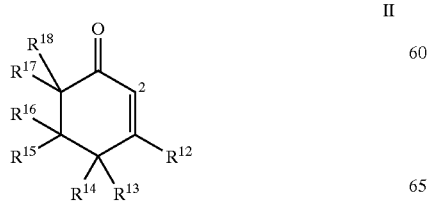

which is linked in the 2-position and where $R^{12}$ is hydroxyl, mercapto, halogen, $OR^{19}$, $SR^{19}$, $SOR^{20}$ or $SO_2R^{20}$;

$R^{13}$, $R^{17}$ are hydrogen, $C_1$–$C_4$-alkyl, $C_1$–$C_4$-alkylthio or $C_1$–$C_4$-alkoxycarbonyl;

$R^{14}$, $R^{16}$, $R^{18}$ are hydrogen or $C_1$–$C_4$-alkyl;

$R^{15}$ is hydrogen, hydroxyl, halogen, $C_1$–$C_6$-alkyl, $C_1$–$C_6$-haloalkyl, di($C_1$–$C_6$-alkoxy)methyl, ($C_1$–$C_6$-alkoxy)($C_1$–$C_6$-alkylthio)methyl, di($C_1$–$C_6$-alkylthio)methyl, $C_1$–$C_6$-alkoxy, $C_1$–$C_6$-haloalkoxy, $C_1$–$C_6$-alkylthio, $C_1$–$C_6$-haloalkylthio, $C_1$–$C_6$-alkoxycarbonyl, $C_1$–$C_6$-haloalkoxycarbonyl, 1,3-dioxolan-2-yl, 1,3-dioxan-2-yl, 1,3-oxathiolan-2-yl, 1,3-oxathian-2-yl, 1,3-dithiolan-2-yl or 1,3-dithian-2-yl, it being possible for the six last-mentioned radicals to have attached to them one, two or three substituents selected from amongst $C_1$–$C_4$-alkyl; or $R^{13}$ and $R^{14}$ or $R^{17}$ and $R^{18}$ together are $C_1$–$C_5$-alkanediyl which can have attached to it one, two or three substituents selected from amongst halogen, cyano, $C_1$–$C_4$-alkyl, $C_1$–$C_4$-haloalkyl or $C_1$–$C_4$-alkoxycarbonyl;

$R^{14}$ and $R^{15}$ or $R^{15}$ and $R^{18}$ together are a chemical bond or $C_1$–$C_5$-alkanediyl which can have attached to it one, two or three substituents selected from amongst halogen, cyano, $C_1$–$C_4$-alkyl, $C_1$–$C_4$-haloalkyl or $C_1$–$C_4$-alkoxycarbonyl; or $R^{14}$ and $R^{18}$ together are $C_1$–$C_5$-alkanediyl which can have attached to it one, two or three substituents selected from amongst halogen, cyano, $C_1$–$C_4$-alkyl, $C_1$–$C_4$-haloalkyl or $C_1$–$C_4$-alkoxycarbonyl; or $R^{15}$ and $R^{16}$ together are —O—$(CH_2)_p$—O—, —O—$(CH_2)_p$—S—, —S—$(CH_2)_p$—S—, —O—$(CH_2)_q$— or —S—$(CH2)_q$—, each of which can have attached to it one, two or three substituents selected from amongst halogen, cyano, $C_1$–$C_4$-alkyl, $C_1$–$C_4$-haloalkyl or $C_1$–$C_4$-alkoxycarbonyl; or $R^{15}$ and $R^{16}$ together are an oxygen atom;

$R^{19}$ is $C_1$–$C_6$-alkyl, $C_3$–$C_6$-alkenyl, $C_3$–$C_6$-haloalkenyl, $C_3$–$C_6$-alkynyl, $C_3$–$C_6$-cycloalkyl, $C_1$–$C_{20}$-alkylcarbonyl, $C_2$–$C_{20}$-alkenylcarbonyl, $C_2$–$C_6$-alkynylcarbonyl, $C_1$–$C_6$-alkoxycarbonyl, $C_3$–$C_6$-alkenyloxycarbonyl, $C_3$–$C_6$-alkynyloxycarbonyl, $C_1$–$C_6$-alkylthiocarbonyl, $C_1$–$C_6$-alkylaminocarbonyl, $C_3$–$C_6$-alkenylaminocarbonyl, $C_3$–$C_6$-alkynylaminocarbonyl, N,N-di($C_1$–$C_6$-alkyl)aminocarbonyl, N-($C_3$–$C_6$-alkenyl)-N-($C_1$–$C_6$-alkyl)aminocarbonyl, N-($C_3$–$C_6$-alkynyl)-N-($C_1$–$C_6$-alkyl)aminocarbonyl, N-($C_1$–$C_6$-alkoxy)-N-($C_1$–$C_6$-alkyl)aminocarbonyl, N,N-di($C_1$–$C_6$-alkyl)aminothiocarbonyl, $C_1$–$C_6$-alkoxyimino-$C_1$–$C_6$-alkyl, it being possible for the abovementioned alkyl, alkoxy and cycloalkyl radicals to be partially or fully halogenated and/or to have attached to them one, two or three substituents selected from amongst cyano, $C_1$–$C_4$-alkoxy, $C_1$–$C_4$-alkylthio, di($C_1$–$C_4$-alkyl)amino, $C_1$–$C_4$-alkylcarbonyl, $C_1$–$C_4$-alkoxycarbonyl, $C_1$–$C_4$-alkoxy-$C_1$–$C_4$-alkoxycarbonyl, $C_1$–$C_4$-alkylaminocarbonyl, N,N-di($C_1$–$C_4$-alkyl)aminocarbonyl or $C_3$–$C_6$-cycloalkyl; phenyl, phenyl-$C_1$–$C_6$-alkyl, phenylcarbonyl-$C_1$–$C_6$-alkyl, phenylcarbonyl, phenoxycarbonyl, phenoxythiocarbonyl, heterocyclyl, heterocyclyl-$C_1$–$C_6$-alkyl, heterocyclylcarbonyl-$C_1$–$C_6$-alkyl, heterocyclylcarbonyl, heterocyclyloxycarbonyl, heterocyclyloxythiocarbonyl, it being possible for the phenyl or heterocyclyl radical of the abovementioned radicals to be partially or fully halogenated and/or to have attached to it one, two or three substituents selected from amongst nitro, cyano, $C_1$–$C_4$-alkyl, $C_1$–$C_4$-haloalkyl, $C_1$–$C_4$-alkoxy or $C_1$–$C_4$-haloalkoxy;

$R^{20}$ is $C_1$–$C_6$-alkyl, $C_3$–$C_6$-alkenyl, $C_3$–$C_6$-haloalkenyl, $C_3$–$C_6$-alkynyl or $C_3$–$C_6$-cycloalkyl, it being possible for the abovementioned alkyl and cycloalkyl radicals to be partially or fully halogenated and/or to have attached to them one, two or three substituents selected from amongst cyano, $C_1$–$C_4$-alkoxy, $C_1$–$C_4$-alkylthio, di($C_1$–$C_4$-alkyl)amino, $C_1$–$C_4$-alkylcarbonyl, $C_1$–$C_4$-alkoxycarbonyl, $C_1$–$C_4$-alkoxy-$C_1$–$C_4$-alkoxycarbonyl, $C_1$–$C_4$-alkylaminocarbonyl, N,N-di($C_1$–$C_4$-alkyl)aminocarbonyl or $C_3$–$C_6$-cycloalkyl; phenyl, phenyl-$C_1$–$C_6$-alkyl, phenylcarbonyl-$C_1$–$C_6$-alkyl, heterocyclyl, heterocyclyl-$C_1$–$C_6$-alkyl or heterocyclylcarbonyl-$C_1$–$C_6$-alkyl, it being possible for the phenyl or heterocyclyl radical of the abovementioned radicals to be partially or fully halogenated and/or to have attached to it one, two or three substituents selected from amongst nitro, cyano, $C_1$–$C_4$-alkyl, $C_1$–$C_4$-haloalkyl, $C_1$–$C_4$-alkoxy or $C_1$–$C_4$-haloalkoxy;

p is 2, 3 or 4;

q is 1, 2, 3, 4 or 5;

and to their agriculturally useful salts.

The invention furthermore relates to processes for the preparation of compounds of the formula I, to compositions comprising them, and to the use of these derivatives or compositions comprising them for controlling harmful plants.

Benzoylcyclohexenones are disclosed in the literature, for example in WO 96/26200.

However, the herbicidal properties of the prior-art compounds and their tolerance by crop plants are only moderately satisfactory.

It is an object of the present invention to find novel, in particular herbicidally active, compounds with improved properties.

We have found that this object is achieved by the 3-(4,5-dihydroisoxazol-5-yl)benzoylcyclohexenones of the formula I and their herbicidal action.

Furthermore, there have been found herbicidal compositions which comprise the compounds I and which have very good herbicidal action. Moreover, there have been found processes for the preparation of these compositions and methods of controlling undesired vegetation using the compounds I.

Depending on the substitution pattern, the compounds of the formula I may contain one or more chiral centers, in which case they are present as enantiomer or diastereomer mixtures. The invention relates both to the pure enantiomers or diastereomers and to their mixtures.

The compounds of the formula I can also be present in the form of their agriculturally useful salts, the type of the salt generally being of no importance. Suitable are in general the salts of those cations, or the acid addition salts of those acids, whose cations, or anions, respectively, do not adversely affect the herbicidal action of the compounds I.

Suitable cations are, in particular, ions of the alkali metals, preferably lithium, sodium and potassium, of the alkaline earth metals, preferably calcium and magnesium, and of the transition metals, preferably manganese, copper, zinc and iron, and also ammonium, it being possible here, if desired, for one to four hydrogen atoms to be replaced by $C_1$–$C_4$-alkyl or hydroxy-$C_1$–$C_4$-alkyl and/or a phenyl or benzyl, preferably ammonium, diisopropylammonium, tetramethylammonium, tetrabutylammonium, trimethylbenzylammonium, and furthermore phosphonium ions, sulfonium ions, preferably tri($C_1$–$C_4$-alkyl)sulfonium and sulfoxonium ions, preferably tri($C_1$–$C_4$-alkyl) sulfoxonium.

Anions of useful acid addition salts are mainly chloride, bromide, fluoride, hydrogensulfate, sulfate, dihydrogenphosphate, hydrogenphosphate, nitrate, hydrogencarbonate, carbonate, hexafluorosilicate, hexafluorophosphate, benzoate, and the anions of $C_1$–$C_4$-alkanoic acids, preferably formate, acetate, propionate and butyrate.

The organic moieties stated for the substituents $R^1$–$R^{20}$ or as radicals on phenyl rings constitute collective terms for individual enumerations of the individual group members. All hydrocarbon chains, that is to say all alkyl, haloalkyl, cyanoalkyl, alkoxy, haloalkoxy, alkylthio, haloalkylthio, alkylsulfinyl, haloalkylsulfinyl, alkylsulfonyl, haloalkylsulfonyl, alkylcarbonyl, haloalkylcarbonyl, alkenylcarbonyl, alkynylcarbonyl, alkoxycarbonyl, haloalkoxycarbonyl, alkenyloxycarbonyl, alkynyloxycarbonyl, alkylthiocarbonyl, alkylaminocarbonyl, alkenylaminocarbonyl, alkynylaminocarbonyl, dialkylaminocarbonyl, (alkenyl)(alkyl)aminocarbonyl, (alkynyl)(alkyl)aminocarbonyl, N-alkoxy-N-alkylaminocarbonyl, N,N-dialkylaminothiocarbonyl, alkoxyalkoxycarbonyl, alkenyloxy, alkynyloxy, alkylamino, dialkylamino, alkoxyalkyl, dialkoxymethyl, (alkoxy)(alkylthio)methyl, dialkoxyalkyl, alkylthioalkyl, di(alkylthio)methyl, dialkylaminoalkyl, dialkylaminoiminoalkyl, hydroxyiminoalkyl, alkoxyiminoalkyl, alkoxycarbonylalkyl, alkoxyalkoxy, alkenyl, haloalkenyl, alkenyloxy, alkynyl and alkynyloxy moieties and the hydrocarbon chains of phenylalkyl, phenylcarbonylalkyl, heterocyclylalkyl and heterocyclylcarbonylalkyl, $C_1$–$C_4$-alkylaminocarbonyl, di($C_1$–$C_4$-alkyl)aminocarbonyl, phenyl-$C_1$–$C_4$-alkyl, phenylcarbonyl-$C_1$–$C_4$-alkyl, heterocyclyl-$C_1$–$C_4$-alkyl and heterocyclylcarbonyl-$C_1$–$C_4$-alkyl can be straight-chain or branched. Unless otherwise specified, halogenated substituents preferably have attached to them one to five identical or different halogen atoms. The meaning halogen is in each case fluorine, chlorine, bromine or iodine.

Other examples of meanings are:

$C_1$–$C_4$-alkyl and the alkyl moieties of $C_1$–$C_4$-alkylcarbonyl, di($C_1$–$C_4$-alkoxy)-$C_1$–$C_4$-alkyl, di($C_1$–$C_4$-alkyl)aminoimino-$C_1$–$C_4$-alkyl, $C_1$–$C_6$-alkoxyimino-$C_1$–$C_4$-alkyl, hydroxyimino-$C_1$–$C_4$-alkyl, $C_1$–$C_4$-alkylaminocarbonyl, di($C_1$–$C_4$-alkyl)aminocarbonyl, phenyl-$C_1$–$C_4$-alkyl, phenylcarbonyl-$C_1$–$C_4$-alkyl, heterocyclyl-$C_1$–$C_4$-alkyl and heterocyclylcarbonyl-$C_1$–$C_4$-alkyl: for example methyl, ethyl, propyl, 1-methylethyl, butyl, 1-methylpropyl, 2-methylpropyl and 1,1-dimethylethyl;

$C_1$–$C_6$-alkyl and the alkyl moieties of $C_1$–$C_6$-alkoxyimino-$C_1$–$C_6$-alkyl, N-$C_3$–$C_6$-alkenyl-N-$C_1$–$C_6$-alkylaminocarbonyl, N-$C_1$–$C_6$-alkynyl-N-$C_1$–$C_6$-alkylaminocarbonyl, N-$C_1$–$C_6$-alkoxy-N-$C_1$–$C_6$-alkylaminocarbonyl, phenyl-$C_1$–$C_6$-alkyl, phenylcarbonyl-$C_1$–$C_6$-alkyl, heterocyclyl-$C_1$–$C_6$-alkyl and heterocyclylcarbonyl-$C_1$–$C_6$-alkyl: $C_1$–$C_4$-alkyl as mentioned above and, for example, pentyl, 1-methylbutyl, 2-methylbutyl, 3-methylbutyl, 2,2-dimethylpropyl, 1-ethylpropyl, hexyl, 1,1- dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1-ethyl-1-methylpropyl and 1-ethyl-3-methylpropyl;

$C_1$–$C_{20}$-alkyl as alkyl moiety of $C_1$–$C_{20}$-alkylcarbonyl: $C_1$–$C_6$-alkyl as mentioned above and heptyl, octyl, pentadecyl or heptadecyl;

$C_1$–$C_4$-haloalkyl and the haloalkyl moieties of $C_1$–$C_4$-haloalkylcarbonyl: a $C_1$–$C_4$-alkyl radical as mentioned above which is partially or fully substituted by fluorine, chlorine, bromine and/or iodine, i.e. e.g. chloromethyl, dichloromethyl, trichloromethyl, fluoromethyl, difluoromethyl, trifluoromethyl, chlorofluoromethyl, dichlorofluoromethyl, chlorodifluoromethyl, bromoethyl, iodomethyl, 1-fluoroethyl, 1-chloroethyl, 1-bromoethyl, 1-iodoethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl and nonafluorobutyl;

$C_1$–$C_6$-haloalkyl: $C_1$–$C_4$-haloalkyl as mentioned above and, for example, 5-fluoropentyl, 5-chloropentyl, 5-bromopentyl, 5-iodopentyl, undecafluoropentyl, 6-fluorohexyl, 6-chlorohexyl, 6-bromohexyl, 6-iodohexyl and dodecafluorohexyl;

$C_1$–$C_4$-cyanoalkyl: for example cyanomethyl, 1-cyanoeth-1-yl, 2-cyanoeth-1-yl, 1-cyanoprop-1-yl, 2-cyanoprop-1-yl, 3-cyanoprop-1-yl, 1-cyanoprop-2-yl, 2-cyanoprop-2-yl, 1-cyanobut-1-yl, 2-cyanobut-1-yl, 3-cyanobut-1-yl, 4-cyanobut-1-yl, 1-cyanobut-2-yl, 2-cyanobut-2-yl, 1-cyanobut-3-yl, 2-cyanobut-3-yl, 1-cyano-2-methylprop-3-yl, 2-cyano-2-methylprop-3-yl, 3-cyano-2-methylprop-3-yl and 2-cyanomethylprop-2-yl;

$C_3$–$C_6$-alkenyl and the alkenyl moieties of $C_3$–$C_6$-alkenylcarbonyl, $C_3$–$C_6$-alkenylaminocarbonyl, N-($C_3$–$C_6$-alkenyl)-N-($C_1$–$C_6$-alkyl)aminocarbonyl: prop-1-en-1-yl, prop-2-en-1-yl, 1-methylethenyl, buten-1-yl, buten-2-yl, buten-3-yl, 1-methylprop-1-en-1-yl, 2-methylprop-1-en-1-yl, 1-methylprop-2-en-1-yl, 2-methylprop-2-en-1-yl, penten-1-yl, penten-2-yl, penten-3-yl, penten-4-yl, 1-methylbut-1-en-1-yl, 2-methylbut-1-en-1-yl, 3-methylbut-1-en-1-yl, 1-methylbut-2-en-1-yl, 2-methylbut-2-en-1-yl, 3-methylbut-2-en-1-yl, 1-methylbut-3-en-1-yl, 2-methylbut-3-en-1-yl, 3-methylbut-3-en-1-yl, 1,1-dimethylprop-2-en-1-yl, 1,2-dimethylprop-1-en-1-yl, 1,2-dimethylprop-2-en-1-yl, 1-ethylprop-1-en-1-yl, 1-ethylprop-2-en-1-yl, hex-1-en-1-yl, hex-2-en-1-yl, hex-3-en-1-yl, hex-4-en-1-yl, hex-5-en-1-yl, 1-methylpent-1-en-1-yl, 2-methylpent-1-en-1-yl, 3-methylpent-1-en-1-yl, 4-methylpent-1-en-1-yl, 1-methylpent-2-en-1-yl, 2-methylpent-2-en-1-yl, 3-methylpent-2-en-1-yl, 4-methylpent-2-en-1-yl, 1-methylpent-3-en-1-yl, 2-methylpent-3-en-1-yl, 3-methylpent-3-en-1-yl, 4-methylpent-3-en-1-yl, 1-methylpent-4-en-1-yl, 2-methylpent-4-en-1-yl, 3-methylpent-4-en-1-yl, 4-methylpent-4-en-1-yl, 1,1-dimethylbut-2-en-1-yl, 1,1-dimethylbut-3-en-1-yl, 1,2-dimethylbut-1-en-1-yl, 1,2-dimethylbut-2-en-1-yl, 1,2-dimethylbut-3-en-1-yl, 1,3-dimethylbut-1-en-1-yl, 1,3-dimethylbut-2-en-1-yl, 1,3-dimethylbut-3-en-1-yl, 2,2-dimethylbut-3-en-1-yl, 2,3-dimethylbut-1-en-1-yl, 2,3-dimethylbut-2-en-1-yl, 2,3-dimethylbut-3-en-1-yl, 3,3-dimethylbut-1-en-1-yl, 3,3-dimethylbut-2-en-1-yl, 1-ethylbut-1-en-1-yl, 1-ethylbut-2-en-1-yl, 1-ethylbut-3-en-1-yl, 2-ethylbut-1-en-1-yl, 2-ethylbut-2-en-1-yl, 2-ethylbut-3-en-1-yl, 1,1,2-trimethylprop-2-en-1-yl, 1-ethyl-1-methylprop-2-en-1-yl, 1-ethyl-2-methylprop-1-en-1-yl and 1-ethyl-2-methylprop-2-en-1-yl;

$C_2$–$C_6$-alkenyl as alkenyl moieties of $C_2$–$C_6$-alkenylcarbonyl: $C_3$–$C_6$-alkenyl as mentioned above, and also ethenyl;

$C_2$–$C_{20}$-alkenyl as alkenyl moieties of $C_2$–$C_{20}$-alkenylcarbonyl: $C_2$–$C_6$-alkenyl as mentioned above, and also 8-pentadecen-1-yl, 8-heptadecen-1-yl and 8,11-heptadecadien-1-yl;

$C_3$–$C_6$-haloalkenyl: a $C_3$–$C_6$-alkenyl radical as mentioned above which is partially or fully substituted by fluorine, chlorine, bromine and/or iodine, i.e. for example 2-chloroallyl, 3-chloroallyl, 2,3-dichloroallyl, 3,3-dichloroallyl, 2,3,3-trichloroallyl, 2,3-dichlorobut-2-enyl, 2-bromoallyl, 3-bromoallyl, 2,3-dibromoallyl, 3,3-dibromoallyl, 2,3,3-tribromoallyl or 2,3-dibromobut-2-enyl;

$C_3$–$C_6$-alkynyl and the alkynyl moieties of $C_3$–$C_6$-alkynylcarbonyl, $C_3$–$C_6$-alkynylaminocarbonyl, N-($C_3$–$C_6$-alkynyl)-N-($C_1$–$C_6$-alkyl)aminocarbonyl: for example propargyl, but-1-yn-3-yl, but-1-yn-4-yl, but-2-yn-1-yl, pent-1-yn-3-yl, pent-1-yn-4-yl, pent-1-yn-5-yl, pent-2-yn-1-yl, pent-2-yn-4-yl, pent-2-yn-5-yl, 3-methylbut-1-yn-3-yl, 3-methylbut-1-yn-4-yl, hex-1-yn-3-yl, hex-1-yn-4-yl, hex-1-yn-5-yl, hex-1-yn-6-yl, hex-2-yn-1-yl, hex-2-yn-4-yl, hex-2-yn-5-yl, hex-2-yn-6-yl, hex-3-yn-1-yl, hex-3-yn-2-yl, 3-methylpent-1-yn-3-yl, 3-methylpent-1-yn-4-yl, 3-methylpent-1-yn-5-yl, 4-methylpent-2-yn-4-yl or 4-methylpent-2-yn-5-yl;

$C_2$–$C_6$-alkynyl as alkynyl moiety of $C_2$–$C_6$-alkynylcarbonyl: $C_3$–$C_6$-alkynyl as mentioned above, and also ethynyl;

$C_1$–$C_4$-alkoxy and the alkoxy moieties of di($C_1$–$C_4$-alkoxy)methyl and di($C_1$–$C_4$-alkoxy)-$C_1$–$C_4$-alkyl: for example methoxy, ethoxy, propoxy, 1-methylethoxy, butoxy, 1-methylpropoxy, 2-methylpropoxy and 1,1-dimethylethoxy;

$C_1$–$C_6$-alkoxy and the alkoxy moieties of $C_1$–$C_6$-alkoxyimino-$C_1$–$C_4$-alkyl, $C_1$–$C_6$-alkoxyimino $C_1$–$C_6$-alkyl, N-$C_1$–$C_6$-alkoxy-N-$C_1$–$C_6$-alkylaminocarbonyl, di($C_1$–$C_6$-alkoxy)methyl and ($C_1$–$C_6$-alkoxy) ($C_1$–$C_6$-alkylthio)methyl: $C_1$–$C_4$-alkoxy as mentioned above, and also for example pentoxy, 1-methylbutoxy, 2-methylbutoxy, 3-methoxybutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2- trimethylpropoxy, 1,2,2-trimethylpropoxy, 1-ethyl-1-methylpropoxy and 1-ethyl-2-methylpropoxy;

$C_1$–$C_4$-haloalkoxy: a $C_1$–$C_4$-alkoxy radical as mentioned above which is partially or fully substituted by fluorine, chlorine, bromine and/or iodine, i.e. for example fluoromethoxy, difluoromethoxy, trifluoromethoxy, chlorodifluoromethoxy, bromodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy, 2-fluoropropoxy, 3-fluoropropoxy, 2-chloropropoxy, 3-chloropropoxy, 2-bromopropoxy, 3-bromopropoxy, 2,2-difluoropropoxy, 2,3-difluoropropoxy, 2,3-dichloropropoxy, 3,3,3-trifluoropropoxy, 3,3,3-trichloropropoxy, 2,2,3,3,3-pentafluoropropoxy, heptafluoropropoxy, 1-(fluoromethyl)-2-fluoroethoxy, 1-(chloromethyl)-2-chloroethoxy, 1-(bromomethyl)-2-bromoethoxy, 4-fluorobutoxy, 4-chlorobutoxy, 4-bromobutoxy and nonafluorobutoxy;

$C_1$–$C_6$-haloalkoxy: $C_1$–$C_4$-haloalkoxy as mentioned above, and also for example 5-fluoropentoxy, 5-chloropentoxy, 5-bromopentoxy, 5-iodopentoxy, undecafluoropentoxy, 6-fluorohexoxy, 6-chlorohexoxy, 6-bromohexoxy, 6-iodohexoxy and dodecafluorohexoxy;

$C_1$–$C_4$-alkylthio: for example methylthio, ethylthio, propylthio, 1-methylethylthio, butylthio, 1-methylpropylthio, 2-methylpropylthio and 1,1-dimethylethylthio;

$C_1$–$C_6$-alkylthio and the alkylthio moieties of ($C_1$–$C_6$-alkoxy) ($C_1$–$C_6$-alkylthio)methyl, di($C_1$–$C_6$-alkylthio)methyl and $C_1$–$C_6$-alkylthiocarbonyl: $C_1$–$C_4$-alkylthio as mentioned above, and also for example pentylthio, 1-methylbutylthio, 2-methylbutylthio, 3-methylbutylthio, 2,2-dimethylpropylthio, 1-ethylpropylthio, hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio and 1-ethyl-2-methylpropylthio;

$C_1$–$C_4$-haloalkylthio: a $C_1$–$C_4$-alkylthio radical as mentioned above which is partially or fully substituted by fluorine, chlorine, bromine and/or iodine, i.e. for example fluoromethylthio, difluoromethylthio, trifluoromethylthio, chlorodifluoromethylthio, bromodifluoromethylthio, 2-fluoroethylthio, 2-chloroethylthio, 2-bromoethylthio, 2-iodoethylthio, 2,2-difluoroethylthio, 2,2,2-trifluoroethylthio, 2,2,2-trichloroethylthio, 2-chloro-2-fluoroethylthio, 2-chloro-2,2-difluoroethylthio, 2,2-dichloro-2-fluoroethylthio, pentafluoroethylthio, 2-fluoropropylthio, 3-fluoropropylthio, 2-chloropropylthio, 3-chloropropylthio, 2-bromopropylthio, 3-bromopropylthio, 2,2-difluoropropylthio, 2,3-difluoropropylthio, 2,3-dichloropropylthio, 3,3,3-trifluoropropylthio, 3,3,3-trichloropropylthio, 2,2,3,3,3-pentafluoropropylthio, heptafluoropropylthio, 1-(fluoromethyl)-2-fluoroethylthio, 1-(chloromethyl)-2-chloroethylthio, 1-(bromomethyl)-2-bromoethylthio, 4-fluorobutylthio, 4-chlorobutylthio, 4-bromobutylthio and nonafluorobutylthio;

$C_1$–$C_6$-haloalkylthio: $C_1$–$C_4$-haloalkylthio as mentioned above, and also for example 5-fluoropentylthio, 5-chloropentylthio, 5-bromopentylthio, 5-iodopentylthio, undecafluoropentylthio, 6-fluorohexylthio, 6-chlorohexylthio, 6-bromohexylthio, 6-iodohexylthio and dodecafluorohexylthio;

$C_1$–$C_6$-alkylsulfinyl ($C_1$–$C_6$-alkyl-S(=O)—): for example methylsulfinyl, ethylsulfinyl, propylsulfinyl, 1-methylethylsulfinyl, butylsulfinyl, 1-methylpropylsulfinyl, 2-methylpropylsulfinyl, 1,1-dimethylethylsulfinyl, pentylsulfinyl, 1-methylbutylsulfinyl, 2-methylbutylsulfinyl, 3-methylbutylsulfinyl, 2,2-dimethylpropylsulfinyl, 1-ethylpropylsulfinyl, 1,1-dimethylpropylsulfinyl, 1,2-dimethylpropylsulfinyl, hexylsulfinyl, 1-methylpentylsulfinyl, 2-methylpentylsulfinyl, 3-methylpentylsulfinyl, 4-methylpentylsulfinyl, 1,1-dimethylbutylsulfinyl, 1,2-dimethylbutylsulfinyl, 1,3-dimethylbutylsulfinyl, 2,2-dimethylbutylsulfinyl, 2,3-dimethylbutylsulfinyl, 3,3-dimethylbutylsulfinyl, 1-ethylbutylsulfinyl, 2-ethylbutylsulfinyl, 1,1,2-trimethylpropylsulfinyl, 1,2,2-trimethylpropylsulfinyl, 1-ethyl-1-methylpropylsulfinyl and 1-ethyl-2-methylpropylsulfinyl;

$C_1$–$C_6$-haloalkylsulfinyl: $C_1$–$C_6$-alkylsulfinyl radical as mentioned above which is partially or fully substituted by fluorine, chlorine, bromine and/or iodine, i.e. for example fluoromethylsulfinyl, difluoromethylsulfinyl, trifluoromethylsulfinyl, chlorodifluoromethylsulfinyl, bromodifluoromethylsulfinyl, 2-fluoroethylsulfinyl, 2-chloroethylsulfinyl, 2-bromoethylsulfinyl, 2-iodoethylsulfinyl, 2,2-difluoroethylsulfinyl, 2,2,2-trifluoroethylsulfinyl, 2,2,2-trichloroethylsulfinyl, 2-chloro-2-fluoroethylsulfinyl, 2-chloro-2,2-difluoroethylsulfinyl, 2,2-dichloro-2-fluoroethylsulfinyl, pentafluoroethylsulfinyl, 2-fluoropropylsulfinyl, 3-fluoropropylsulfinyl, 2-chloropropylsulfinyl, 3-chloropropylsulfinyl, 2-bromopropylsulfinyl, 3-bromopropylsulfinyl, 2,2-difluoropropylsulfinyl, 2,3-difluoropropylsulfinyl, 2,3-dichloropropylsulfinyl, 3,3,3-trifluoropropylsulfinyl, 3,3,3-trichloropropylsulfinyl, 2,2,3,3,3-pentafluoropropylsulfinyl, heptafluoropropylsulfinyl, 1-(fluoromethyl)-2-fluoroethylsulfinyl, 1-(chloromethyl)-2-chloroethylsulfinyl, 1-(bromomethyl)-2-bromoethylsulfinyl, 4-fluorobutylsulfinyl, 4-chlorobutylsulfinyl, 4-bromobutylsulfinyl, nonafluorobutylsulfinyl, 5-fluoropentylsulfinyl, 5-chloropentylsulfinyl, 5-bromopentylsulfinyl, 5-iodopentylsulfinyl, undecafluoropentylsulfinyl, 6-fluorohexylsulfinyl, 6-chlorohexylsulfinyl, 6-bromohexylsulfinyl, 6-iodohexylsulfinyl and dodecafluorohexylsulfinyl;

$C_1$–$C_4$-alkylsulfonyl ($C_1$–$C_6$-alkyl-S(=O)$_2$—): for example methylsulfonyl, ethylsulfonyl, propylsulfonyl, 1-methylethylsulfonyl, butylsulfonyl, 1-methylpropylsulfonyl, 2-methylpropylsulfonyl and 1,1-dimethylethylsulfonyl;

$C_1$–$C_6$-alkylsulfonyl: $C_1$–$C_4$-alkylsulfonyl as mentioned above, and also for example pentylsulfonyl, 1-methylbutylsulfonyl, 2-methylbutylsulfonyl, 3-methylbutylsulfonyl, 1,1-dimethylpropylsulfonyl, 1,2-dimethylpropylsulfonyl, 2,2-dimethylpropylsulfonyl, 1-ethylpropylsulfonyl, hexylsulfonyl, 1-methylpentylsulfonyl, 2-methylpentylsulfonyl, 3-methylpentylsulfonyl, 4-methylpentylsulfonyl, 1,1-dimethylbutylsulfonyl, 1,2-dimethylbutylsulfonyl, 1,3-dimethylbutylsulfonyl, 2,2-dimethylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethylpropylsulfonyl, 1,2,2-trimethylpropylsulfonyl, 1-ethyl-1-methylpropylsulfonyl and 1-ethyl-2-methylpropylsulfonyl;

$C_1$–$C_4$-haloalkylsulfonyl: a $C_1$–$C_6$-alkylsulfonyl radical as mentioned above which is partially or fully substituted by fluorine, chlorine, bromine and/or iodine, i.e. for example fluoromethylsulfonyl, difluoromethylsulfonyl, trifluoromethylsulfonyl, chlorodifluoromethylsulfonyl, bromodifluoromethylsulfonyl, 2-fluoroethylsulfonyl, 2-chloroethylsulfonyl, 2-bromoethylsulfonyl, 2-iodoethylsulfonyl, 2,2-difluoroethylsulfonyl, 2,2,2-trifluoroethylsulfonyl, 2-chloro-2-fluoroethylsulfonyl, 2-chloro-2,2-difluoroethylsulfonyl, 2,2-dichloro-2-fluoroethylsulfonyl, 2,2,2-trichloroethylsulfonyl, pentafluoroethylsulfonyl, 2-fluoropropylsulfonyl, 3-fluoropropylsulfonyl, 2-chloropropylsulfonyl, 3-chloropropylsulfonyl, 2-bromopropylsulfonyl, 3-bromopropylsulfonyl, 2,2-difluoropropylsulfonyl, 2,3-difluoropropylsulfonyl, 2,3-dichloropropylsulfonyl, 3,3,3-trifluoropropylsulfonyl, 3,3,3-trichloropropylsulfonyl, 2,2,3,3,3-pentafluoropropylsulfonyl, heptafluoropropylsulfonyl, 1-(fluoromethyl)-2-fluoroethylsulfonyl, 1-(chloromethyl)-2-chloroethylsulfonyl, 1-(bromomethyl)-2-bromoethylsulfonyl, 4-fluorobutylsulfonyl, 4-chlorobutylsulfonyl, 4-bromobutylsulfonyl and nonafluorobutylsulfonyl;

$C_1$–$C_6$-haloalkylsulfonyl: a $C_1$–$C_4$-haloalkylsulfonyl radical as mentioned above, and also 5-fluoropentylsulfonyl, 5-chloropentylsulfonyl, 5-bromopentylsulfonyl, 5-iodopentylsulfonyl, 6-fluorohexylsulfonyl, 6-bromohexylsulfonyl, 6-iodohexylsulfonyl and dodecafluorohexylsulfonyl;

$C_1$–$C_4$-alkoxycarbonyl: for example methoxycarbonyl, ethoxycarbonyl, propoxycarbonyl, 1-methylethoxycarbonyl, butoxycarbonyl, 1-methylpropoxycarbonyl, 2-methylpropoxycarbonyl and 1,1-dimethoxycarbonyl;

$C_1$–$C_6$-alkoxycarbonyl: a $C_1$–$C_4$-alkoxycarbonyl radical as mentioned above, and also for example: pentoxycarbonyl, 1-methylbutoxycarbonyl, 2-methylbutoxycarbonyl, 3-methylbutoxycarbonyl, 1,1-dimethylpropoxycarbonyl, 1,2-dimethylpropoxycarbonyl, 2,2-dimethylpropoxycarbonyl, 1-ethylpropoxycarbonyl, hexoxycarbonyl, 1-methylpentoxycarbonyl, 2-methylpentoxycarbonyl, 3-methylpentoxycarbonyl, 4-methylpentoxycarbonyl, 1,1-dimethylbutoxycarbonyl, 1,2-dimethylbutoxycarbonyl, 1,3-dimethylbutoxycarbonyl, 2,2-dimethylbutoxycarbonyl, 2,3-dimethylbutoxycarbonyl, 3,3-dimethylbutoxycarbonyl, 1-ethylbutoxycarbonyl, 2-ethylbutoxycarbonyl, 1,2,2-trimethylpropoxycarbonyl, 1,2,2-trimethylpropoxycarbonyl, 1-ethyl-1-methylpropoxycarbonyl and 1-ethyl-2-methylpropoxycarbonyl;

$C_1$–$C_4$-haloalkoxycarbonyl: a $C_1$–$C_4$-alkoxycarbonyl radical as mentioned above which is partially or fully substituted by fluorine, chlorine, bromine and/or iodine, i.e. for example fluoromethoxycarbonyl, difluoromethoxycarbonyl, trifluoromethoxycarbonyl, chlorodifluoromethoxycarbonyl, bromodifluoromethoxycarbonyl, 2-fluoroethoxycarbonyl, 2-chloroethoxycarbonyl, 2-bromoethoxycarbonyl, 2-iodoethoxycarbonyl, 2,2-difluoroethoxycarbonyl, 2,2,2-trifluoroethoxycarbonyl, 2-chloro-2-fluoroethoxycarbonyl, 2-chloro-2,2-difluoroethoxycarbonyl, 2,2-dichloro-2-fluoroethoxycarbonyl, 2,2,2-trichloroethoxycarbonyl, pentafluoroethoxycarbonyl, 2-fluoropropoxycarbonyl, 3-fluoropropoxycarbonyl, 2-chloropropoxycarbonyl, 3-chloropropoxycarbonyl, 2-bromopropoxycarbonyl, 3-bromopropoxycarbonyl, 2,2-difluoropropoxycarbonyl, 2,3-difluoropropoxycarbonyl, 2,3-dichloropropoxycarbonyl, 3,3,3-trifluoropropoxycarbonyl, 3,3,3-trichloropropoxycarbonyl, 2,2,3,3,3-pentafluoropropoxycarbonyl, heptafluoropropoxycarbonyl, 1-(fluoromethyl)-2-fluoroethoxycarbonyl, 1-(chloromethyl)-2-chloroethoxycarbonyl, 1-(bromomethyl)-2-bromoethoxycarbonyl, 4-fluorobutoxycarbonyl, 4-chlorobutoxycarbonyl, 4-bromobutoxycarbonyl and 4-iodobutoxycarbonyl;

$C_1$–$C_6$-haloalkoxycarbonyl: a $C_1$–$C_4$-haloalkoxycarbonyl radical as mentioned above, and also 5-fluoropentoxycarbonyl, 5-chloropentoxycarbonyl, 5-bromopentoxycarbonyl, 5-iodopentoxycarbonyl, 6-fluorohexoxycarbonyl, 6-bromohexoxycarbonyl, 6-iodohexoxycarbonyl and dodecafluorohexoxycarbonyl;

$C_3$–$C_6$-alkenyloxy and the $C_3$–$C_6$-alkenyloxy moieties of $C_3$–$C_6$-Alkenyloxycarbonyl: for example prop-1-en-1-yloxy, prop-2-en-1-yloxy, 1-methylethenyloxy, buten-1-yloxy, buten-2-yloxy, buten-3-yloxy, 1-methylprop-1-en-1-yloxy, 2-methylprop-1-en-1-yloxy, 1-methylprop-2-en-1-yloxy, 2-methylprop-2-en-1-yloxy, penten-1-yloxy, penten-2-yloxy, penten-3-yloxy, penten-4-yloxy, 1-methylbut-1-en-1-yloxy, 2-methylbut-1-en-1-yloxy, 3-methylbut-1-en-1-yloxy, 1-methylbut-2-en-1-yloxy, 2-methylbut-2-en-1-yloxy, 3-methylbut-2-en-1-yloxy, 1-methylbut-3-en-1-yloxy, 2-methylbut-3-en-1-yloxy, 3-methylbut-3-en-1-yloxy, 1,1-dimethylprop-2-en-1-yloxy, 1,2-dimethylprop-1-en-1-yloxy, 1,2-dimethylprop-2-en-1-yloxy, 1-ethylprop-1-en-2-yloxy, 1-ethylprop-2-en-1-yloxy, hex-1-en-1-yloxy, hex-2-en-1-yloxy, hex-3-en-1-yloxy, hex-4-en-1-yloxy, hex-5-en-1-yloxy, 1-methylpent-1-en-1-yloxy, 2-methylpent-1-en-1-yloxy, 3-methylpent-1-en-1-yloxy, 4-methylpent-1-en-1-yloxy, 1-methylpent-2-en-1-yloxy, 2-methylpent-2-en-1-yloxy, 3-methylpent-2-en-1-yloxy, 4-methylpent-2-en-1-yloxy, 1-methylpent-3-en-1-yloxy, 2-methylpent-3-en-1-yloxy, 3-methylpent-3-en-1-yloxy, 4-methylpent-3-en-1-yloxy, 1-methylpent-4-en-1-yloxy, 2-methylpent-4-en-1-yloxy, 3-methylpent-4-en-1-yloxy, 4-methylpent-4-en-1-yloxy, 1,1-dimethylbut-2-en-1-yloxy, 1,1-dimethylbut-3-en-1-yloxy, 1,2-dimethylbut-1-en-1-yloxy, 1,2-dimethylbut-2-en-1-yloxy, 1,2-dimethylbut-3-en-1-yloxy, 1,3-dimethylbut-1-en-1-yloxy, 1,3-dimethylbut-2-en-1-yloxy, 1,3-dimethylbut-3-en-1-yloxy, 2,2-dimethylbut-3-en-1- yloxy, 2,3-dimethylbut-1-en-1-yloxy, 2,3-dimethylbut-2-en-1-yloxy, 2,3-dimethylbut-3-en-1-yloxy, 3,3-dimethylbut-1-en-1-yloxy, 3,3-dimethylbut-2-en-1-yloxy, 1-ethylbut-1-en-1-yloxy, 1-ethylbut-2-en-1-yloxy, 1-ethylbut-3-en-1-yloxy, 2-ethylbut-1-en-1-yloxy, 2-ethylbut-2-en-1-yloxy, 2-ethylbut-3-en-1-yloxy, 1,1,2-trimethylprop-2-en-1-yloxy, 1-ethyl-1-methylprop-2-en-1-yloxy, 1-ethyl-2-methylprop-1-en-1-yloxy and 1-ethyl-2-methylprop-2-en-1-yloxy;

$C_3$–$C_6$-alkynyloxy and the alkynyloxy moieties of $C_3$–$C_6$-alkynyloxycarbonyl: for example prop-1-yn-1-yloxy, prop-2-yn-1-yloxy, but-1-yn-1-yloxy, but-1-yn-3-yloxy, but-1-yn-4-yloxy, but-2-yn-1-yloxy, pent-1-yn-1-yloxy, pent-1-yn-3-yloxy, pent-1-yn-4-yloxy, pent-1-yn-5-yloxy, pent-2-yn-1-yloxy, pent-2-yn-4-yloxy, pent-2-yn-5-yloxy, 3-methylbut-1-yn-3-yloxy, 3-methylbut-1-yn-4-yloxy, hex-1-yn-1-yloxy, hex-1-yn-3-yloxy, hex-1-yn-4-yloxy, hex-1-yn-5-yloxy, hex-1-yn-6-yloxy, hex-2-yn-1-yloxy, hex-2-yn-4-yloxy, hex-2-yn-5-yloxy, hex-2-yn-6-yloxy, hex-3-yn-1-yloxy, hex-3-yn-2-yloxy, 3-methylpent-1-yn-1-yloxy, 3-methylpent-1-yn-3-yloxy, 3-methylpent-1-yn-4-yloxy, 3-methylpent-1-yn-5-yloxy, 4-methylpent-1-yn-1-yloxy, 4-methylpent-2-yn-4-yloxy and 4-methylpent-2-yn-5-yloxy;

$C_1$–$C_6$-alkylamino and the alkylamino moieties of $C_1$–$C_6$-alkylaminocarbonyl: for example methylamino, ethylamino, propylamino, 1-methylethylamino, butylamino, 1-methylpropylamino, 2-methylpropylamino, 1,1-dimethylethylamino, pentylamino, 1-methylbutylamino, 2-methylbutylamino, 3-methylbutylamino, 2,2-dimethylpropylamino, 1-ethylpropylamino, hexylamino, 1,1-dimethylpropylamino, 1,2-dimethylpropylamino, 1-methylpentylamino, 2-methylpentylamino, 3-methylpentylamino, 4-methylpentylamino, 1,1-dimethylbutylamino, 1,2-dimethylbutylamino, 1,3-dimethylbutylamino, 2,2-dimethylbutylamino, 2,3-dimethylbutylamino, 3,3-dimethylbutylamino, 1-ethylbutylamino, 2-ethylbutylamino, 1,1,2-trimethylpropylamino, 1,2,2-trimethylpropylamino, 1-ethyl-1-methylpropylamino or 1-ethyl-2-methylpropylamino;

di($C_1$–$C_4$-alkyl)amino and the dialkylamino moieties of di($C_1$–$C_4$-alkyl)aminoimino-$C_1$–$C_4$-alkyl and di($C_1$–$C_4$-alkyl)aminocarbonyl: for example N,N-dimethylamino, N,N-diethylamino, N,N-dipropylamino, N,N-di(1-methylethyl)amino, N,N-dibutylamino, N,N-di(1-methylpropyl)amino, N,N-di(2-methylpropyl)amino, N,N-di(1,1-dimethylethyl)amino, N-ethyl-N-methylamino, N-methyl-N-propylamino, N-methyl-N-(1-methylethyl)amino, N-butyl-N-methylamino, N-methyl-N-(1-methylpropyl)amino, N-methyl-N-(2-methylpropyl)amino, N-(1,1-dimethylethyl)-N-methylamino, N-ethyl-N-propylamino, N-ethyl-N-(1-methylethyl)amino, N-butyl-N-ethylamino, N-ethyl-N-(1-methylpropyl)amino, N-ethyl-N-(2-methylpropyl)amino, N-ethyl-N-(1,1-dimethylethyl)amino, N-(1-methylethyl)-N-propylamino, N-butyl-N-propylamino, N-(1-methylpropyl)-N-propylamino, N-(2-methylpropyl)-N-propylamino, N-(1,1-dimethylethyl)-N-propylamino, N-butyl-N-(1-methylethyl)amino, N-(1-methylethyl)-N-(1-methylpropyl)amino, N-(1-methylethyl)-N-(2-methylpropyl)amino, N-(1,1-dimethylethyl)-N-(1-methylethyl)amino, N-butyl-N-(1-methylpropyl)amino, N-butyl-N-(2-methylpropyl) amino, N-butyl-N-(1,1-dimethylethyl)amino, N-(1-methylpropyl)-N-(2-methylpropyl)amino, N-(1,1-dimethylethyl)-N-(1-methylpropyl)amino and N-(1,1-dimethylethyl)-N-(2-methylpropyl)amino;

di($C_1$–$C_6$-alkyl)amino and the dialkylamino moieties of di($C_1$–$C_6$-alkyl)aminocarbonyl and di($C_1$–$C_6$-alkyl)aminothiocarbonyl: di($C_1$–$C_4$-alkyl)amino as mentioned above, and also N,N-dipentylamino, N,N-dihexylamino, N-methyl-N-pentylamino, N-ethyl-N-pentylamino, N-methyl-N-hexylamino or N-ethyl-N-hexylamino;

di($C_1$–$C_4$-alkyl)amino-$C_1$–$C_4$-alkyl: $C_1$–$C_4$-alkyl substituted by di($C_1$–$C_4$-alkyl)amino as mentioned above, i.e., for example, N,N-dimethylaminomethyl, N,N-diethylaminomethyl, N,N-dipropylaminomethyl, N,N-di(1-methylethyl)aminomethyl, N,N-dibutylaminomethyl, N,N-di(1-methylpropyl)aminomethyl, N,N-di(2-methylpropyl)aminomethyl, N,N-di(1,1-dimethylethyl)aminomethyl, N-ethyl-N-methylaminomethyl, N-methyl-N-propylaminomethyl, N-methyl-N-(1-methylethyl)aminomethyl, N-butyl-N-methylaminomethyl, N-methyl-N-(1-methylpropyl)aminomethyl, N-methyl-N-(2-methylpropyl)aminomethyl, N-(1,1-dimethylethyl)-N-methylaminomethyl, N-ethyl-N-propylaminomethyl, N-ethyl-N-(1-methylethyl)aminomethyl, N-butyl-N-ethylaminomethyl, N-ethyl-N-(1-methylpropyl)aminomethyl, N-ethyl-N-(2-methylpropyl)aminomethyl, N-ethyl-N-(1,1-dimethylethyl)aminomethyl, N-(1-methylethyl)-N-propylaminomethyl, N-butyl-N-propylaminomethyl, N-(1-methylpropyl)-N-propylaminomethyl, N-(2-methylpropyl)-N-propylaminomethyl, N-(1,1-dimethylethyl)-N-propylaminomethyl, N-butyl-N-(1-methylethyl)aminomethyl, N-(1-methylethyl)-N-(1-methylpropyl)aminomethyl, N-(1-methylethyl)-N-(2-methylpropyl)aminomethyl, N-(1,1-dimethylethyl)-N-(1-methylethyl)aminomethyl, N-butyl-N-(1-methylpropyl)aminomethyl, N-butyl-N-(2-methylpropyl)aminomethyl, N-butyl-N-(1,1-dimethylethyl)aminomethyl, N-(1-methylpropyl)-N-(2-methylpropyl)aminomethyl, N-(1,1-dimethylethyl)-N-(1-methylpropyl)aminomethyl, N-(1,1-dimethylethyl)-N-(2-methylpropyl)aminomethyl, 2-(N,N-dimethylamino)ethyl, 2-(N,N-diethylamino)ethyl, 2-(N,N-dipropylamino)ethyl, 2-[N,N-di-(1-methylethyl)amino]ethyl, 2-[N,N-dibutylamino]ethyl, 2-[N,N-di(1-methylpropyl)amino]ethyl, 2-[N,N-di(2-methylpropyl)amino]ethyl, 2-[N,N-di(1,1-dimethylethyl)amino]ethyl, 2-[N-ethyl-N-methylamino]ethyl, 2-[N-methyl-N-propylamino]ethyl, 2-[N-methyl-N-(1-methylethyl)amino]ethyl, 2-[N-butyl-N-methylamino]ethyl, 2-[N-methyl-N-(1-methylpropyl)amino]ethyl, 2-[N-methyl-N-(2-methylpropyl)amino]ethyl, 2-[N-(1,1-dimethylethyl)-N-methylamino]ethyl, 2-[N-ethyl-N-propylamino]ethyl, 2-[N-ethyl-N-(1-methylethyl)amino]ethyl, 2-[N-butyl-N-ethylamino]ethyl, 2-[N-ethyl-N-(1-methylpropyl)amino]ethyl, 2-[N-ethyl-N-(2-methylpropyl)amino]ethyl, 2-[N-ethyl-N-(1,1-dimethylethylamino]ethyl, 2-[N-(1-methylethyl)-N-propylamino]ethyl, 2-[N-Butyl-N-propylamino]ethyl, 2-[N-(1-methylpropyl)-N-propylamino]ethyl, 2-[N-(2-methylpropyl)-N-propylamino]ethyl, 2-[N-(1,1-dimethylethyl)-N-propylamino]ethyl, 2-[N-butyl-N-(1-methylethyl)amino]ethyl, 2-[N-(1-methylethyl)-N-(1-methylpropyl)amino]ethyl, 2-[N-(1-methylethyl)-N-

(2-methylpropyl)amino]ethyl, 2-[N-(1,1-dimethylethyl)-N-(1-methylethyl)amino]ethyl, 2-[N-butyl-N-(1-methylpropyl)amino]ethyl, 2-[N-butyl-N-(2-methylpropyl)amino]ethyl, 2-[N-butyl-N-(1,1-dimethylethyl)amino]ethyl, 2-[N-(1-methylpropyl)-N-(2-methylpropyl)amino]ethyl, 2-[N-(1,1-dimethylethyl)-N-(1-methylpropyl)amino]ethyl, 2-[N-(1,1-dimethylethyl)-N-(2-methylpropyl)amino]ethyl, 3-(N,N-dimethylamino)propyl, 3-(N,N-diethylamino) propyl, 4-(N,N-dimethylamino)butyl and 4-(N,N-diethylamino)butyl;

$C_1$–$C_4$-alkoxy-$C_1$–$C_4$-alkyl: $C_1$–$C_4$-alkyl substituted by $C_1$–$C_4$-alkoxy as mentioned above, i.e., for example, methoxymethyl, ethoxymethyl, propoxymethyl, (1-methylethoxy)methyl, butoxymethyl, (1-methylpropoxy)methyl, (2-methylpropoxy)methyl, (1,1-dimethylethoxy)methyl, 2-(methoxy)ethyl, 2-(ethoxy)ethyl, 2-(Propoxy)ethyl, 2-(1-methylethoxy) ethyl, 2-(butoxy) ethyl, 2-(1-methylpropoxy) ethyl, 2-(2-methylpropoxy)ethyl, 2-(1,1-dimethylethoxy) ethyl, 2-(methoxy)propyl, 2-(ethoxy)propyl, 2-(propoxy)propyl, 2-(1-methylethoxy)propyl, 2-(butoxy)propyl, 2-(1-methylpropoxy)propyl, 2-(2-methylpropoxy)propyl, 2-(1,1-dimethylethoxy)propyl, 3-(methoxy)propyl, 3-(ethoxy)propyl, 3-(propoxy) propyl, 3-(1-methylethoxy)propyl, 3-(butoxy)propyl, 3-(1-methylpropoxy)propyl, 3-(2-methylpropoxy) propyl, 3-(1,1-dimethylethoxy)propyl, 2-(methoxy) butyl, 2-(ethoxy)butyl, 2-(propoxy)butyl, 2-(1-methylethoxy)butyl, 2-(butoxy)butyl, 2-(1-methylpropoxy)butyl, 2-(2-methylpropoxy)butyl, 2-(1,1-dimethylethoxy)butyl, 3-(methoxy)butyl, 3-(ethoxy) butyl, 3-(propoxy)butyl, 3-(1-methylethoxy)butyl, 3-(butoxy)butyl, 3-(1-methylpropoxy)butyl, 3-(2-methylpropoxy)butyl, 3-(1,1-dimethylethoxy)butyl, 4-(methoxy)butyl, 4-(ethoxy)butyl, 4-(propoxy)butyl, 4-(1-methylethoxy)butyl, 4-(butoxy)butyl, 4-(1-methylpropoxy)butyl, 4-(2-methylpropoxy)butyl and 4-(1,1-dimethylethoxy)butyl;

$C_1$–$C_4$-alkylthio-$C_1$–$C_4$-alkyl: $C_1$–$C_4$-alkyl substituted by $C_1$–$C_4$-alkylthio as mentioned above, i.e., for example, methylthiomethyl, ethylthiomethyl, propylthiomethyl, (1-methylethylthio)methyl, butylthiomethyl, (1-methylpropylthio)methyl, (2-methylpropylthio) methyl, (1,1-dimethylethylthio)methyl, 2-methylthioethyl, 2-ethylthioethyl, 2-(propylthio) ethyl, 2-(1-methylethylthio)ethyl, 2-(butylthio)ethyl, 2-(1-methylpropylthio) ethyl, 2-(2-methylpropylthio) ethyl, 2-(1,1-dimethylethylthio)ethyl, 2-(methylthio) propyl, 3-(methylthio)propyl, 2-(ethylthio)propyl, 3-(ethylthio)propyl, 3-(propylthio)propyl, 3-(butylthio) propyl, 4-(methylthio)butyl, 4-(ethylthio)butyl, 4-(propylthio)butyl and 4-(butylthio)butyl;

$C_1$–$C_4$-alkoxycarbonyl-$C_1$–$C_4$-alkyl: $C_1$–$C_4$-alkyl substituted by $C_1$–$C_4$-alkoxycarbonyl, i.e., for example, methoxycarbonylmethyl, ethoxycarbonylmethyl, propoxycarbonylmethyl, (1-methylethoxycarbonyl) methyl, butoxycarbonylmethyl, (1-methylpropoxycarbonyl)methyl, (2-methylpropoxycarbonyl)methyl, (1,1-dimethylethoxycarbonyl)methyl, 2-(methoxycarbonyl) ethyl, 2-(ethoxycarbonyl)ethyl, 2-(propoxycarbonyl) ethyl, 2-(1-methylethoxycarbonyl)ethyl, 2-(butoxycarbonyl)ethyl, 2-(1-methylpropoxycarbonyl)ethyl, 2-(2-methylpropoxycarbonyl)ethyl, 2-(1,1-dimethylethoxycarbonyl)ethyl, 2-(methoxycarbonyl) propyl, 2-(ethoxycarbonyl)propyl, 2-(propoxycarbonyl)propyl, 2-(1-methylethoxycarbonyl)propyl, 2-(butoxycarbonyl) propyl, 2-(1-methylpropoxycarbonyl)propyl, 2-(2-methylpropoxycarbonyl)propyl, 2-(1,1-dimethylethoxycarbonyl)propyl, 3-(methoxycarbonyl) propyl, 3-(ethoxycarbonyl)propyl, 3-(propoxycarbonyl)propyl, 3-(1-methylethoxycarbonyl)propyl, 3-(butoxycarbonyl) propyl, 3-(1-methylpropoxycarbonyl)propyl, 3-(2-methylpropoxycarbonyl)propyl, 3-(1,1-dimethylethoxycarbonyl)propyl, 2-(methoxycarbonyl) butyl, 2-(ethoxycarbonyl)butyl, 2-(propoxycarbonyl) butyl, 2-(1-methylethoxycarbonyl)butyl, 2-(butoxycarbonyl)butyl, 2-(1-methylpropoxycarbonyl)butyl, 2-(2-methylpropoxycarbonyl)butyl, 2-(1,1-dimethylethoxycarbonyl)butyl, 3-(methoxycarbonyl) butyl, 3-(ethoxycarbonyl)butyl, 3-(propoxycarbonyl) butyl, 3-(1-methylethoxycarbonyl)butyl, 3-(butoxycarbonyl)butyl, 3-(1-methylpropoxycarbonyl)butyl, 3-(2-methylpropoxycarbonyl)butyl, 3-(1,1-dimethylethoxycarbonyl)butyl, 4-(methoxycarbonyl) butyl, 4-(ethoxycarbonyl)butyl, 4-(propoxycarbonyl) butyl, 4-(1-methylethoxycarbonyl)butyl, 4-(butoxycarbonyl)butyl, 4-(1-methylpropoxy)butoxy, 4-(2-methylpropoxy)butoxy and 4-(1,1-dimethylethoxycarbonyl)butyl;

$C_1$–$C_4$-alkoxy-$C_2$–$C_4$-alkoxy: $C_2$–$C_4$-alkoxy substituted by $C_1$–$C_4$-alkoxy as mentioned above, i.e., for example, 2-(methoxy)ethoxy, 2-(ethoxy)ethoxy, 2-(propoxy)ethoxy, 2-(1-methylethoxy)ethoxy, 2-(butoxy)ethoxy, 2-(1-methylpropoxy)ethoxy, 2-(2-methylpropoxy)ethoxy, 2-(1,1-dimethylethoxy)ethoxy, 2-(methoxy)propoxy, 2-(ethoxy)propoxy, 2-(propoxy) propoxy, 2-(1-methylethoxy)propoxy, 2-(butoxy) propoxy, 2-(1-methylpropoxy)propoxy, 2-(2-methylpropoxy)propoxy, 2-(1,1-dimethylethoxy) propoxy, 3-(methoxy)propoxy, 3-(ethoxy)propoxy, 3-(propoxy)propoxy, 3-(1-methylethoxy)propoxy, 3-(butoxy)propoxy, 3-(1-methylpropoxy)propoxy, 3-(2-methylpropoxy)propoxy, 3-(1,1-dimethylethoxy) propoxy, 2-(methoxy)butoxy, 2-(ethoxy)butoxy, 2-(propoxy)butoxy, 2-(i-methylethoxy)butoxy, 2-(butoxy)butoxy, 2-(1-methylpropoxy)butoxy, 2-(2-methylpropoxy)butoxy, 2-(1,1-dimethylethoxy)butoxy, 3-(methoxy)butoxy, 3-(ethoxy)butoxy, 3-(propoxy) butoxy, 3-(1-methylethoxy)butoxy, 3-(butoxy)butoxy, 3-(1-methylpropoxy)butoxy, 3-(2-methylpropoxy) butoxy, 3-(1,1-dimethylethoxy)butoxy, 4-(methoxy) butoxy, 4-(ethoxy)butoxy, 4-(propoxy)butoxy, 4-(1-methylethoxy)butoxy, 4-(butoxy)butoxy, 4-(1-methylpropoxy)butoxy, 4-(2-methylpropoxy)butoxy and 4-(1,1-dimethylethoxy)butoxy;

$C_2$–$C_5$-alkanediyl: for example ethane-1,2-diyl, propane-1,3-diyl, butane-1,4-diyl and pentane-1,5-diyl;

$C_1$–$C_5$-alkanediyl: $C_2$–$C_5$-alkanediyl as mentioned above, and also methanediyl;

$C_2$–$C_6$-alkanediyl: $C_2$–$C_5$-alkanediyl as mentioned above, and also hexane-1,6-diyl;

$C_3$–$C_6$-cycloalkyl: for example cyclopropyl, cyclobutyl, cyclopentyl and cyclohexyl;

$C_3$–$C_8$-cycloalkyl: $C_3$–$C_6$-cycloalkyl as mentioned above, and also cycloheptyl and cyclooctyl;

heterocyclyl and heterocyclyl moieties of heterocyclylcarbonyl, heterocyclyl-$C_1$–$C_6$-alkyl, heterocyclylcarbonyl-$C_1$–$C_6$-alkyl: a saturated, partially saturated or unsaturated 5- or 6-membered heterocyclic ring which contains one to four identical or different hetero atoms selected from the following group: oxygen, sulfur or nitrogen, i.e., for example, 5-membered saturated rings such as:

tetrahydrofuran-2-yl, tetrahydrofuran-3-yl, tetrahydrothien-2-yl, tetrahydrothien-3-yl, tetrahydropyrrol-2-yl, tetrahydropyrrol-3-yl, tetrahydropyrazol-3-yl, tetrahydropyrazol-4-yl, tetrahydroisoxazol-3-yl, tetrahydroisoxazol-4-yl, tetrahydroisoxazol-5-yl, 1,2-oxathiolan-3-yl, 1,2-oxathiolan-4-yl, 1,2-oxathiolan-5-yl, tetrahydroisothiazol-3-yl, tetrahydroisothiazol-4-yl, tetrahydroisothiazol-5-yl, 1,2-dithiolan-3-yl, 1,2-dithiolan-4-yl, tetrahydroimidazol-2-yl, tetrahydroimidazol-4-yl, tetrahydrooxazol-2-yl, tetrahydrooxazol-4-yl, tetrahydrooxazol-5-yl, tetrahydrothiazol-2-yl, tetrahydrothiazol-4-yl, tetrahydrothiazol-5-yl, 1,3-dioxolan-2-yl, 1,3-dioxolan-4-yl, 1,3-oxathiolan-2-yl, 1,3-oxathiolan-4-yl, 1,3-oxathiolan-5-yl, 1,3-dithiolan-2-yl, 1,3-dithiolan-4-yl, 1,3,2-dioxathiolan-4-yl;

5-membered partially saturated rings such as: 2,3-dihydrofuran-2-yl, 2,3-dihydrofuran-3-yl, 2,5-dihydrofuran-2-yl, 2,5-dihydrofuran-3-yl, 4,5-dihydrofuran-2-yl, 4,5-dihydrofuran-3-yl, 2,3-dihydrothien-2-yl, 2,3-dihydrothien-3-yl, 2,5-dihydrothien-2-yl, 2,5-dihydrothien-3-yl, 4,5-dihydrothien-2-yl, 4,5-dihydrothien-3-yl, 2,3-dihydro-1H-pyrrol-2-yl, 2,3-dihydro-1H-pyrrol-3-yl, 2,5-dihydro-1H-pyrrol-2-yl, 2,5-dihydro-1H-pyrrol-3-yl, 4,5-dihydro-1H-pyrrol-2-yl, 4,5-dihydro-1H-pyrrol-3-yl, 3,4-dihydro-2H-pyrrol-2-yl, 3,4-dihydro-2H-pyrrol-3-yl, 3,4-dihydro-5H-pyrrol-2-yl, 3,4-dihydro-5H-pyrrol-3-yl, 4,5-dihydro-1H-pyrazol-3-yl, 4,5-dihydro-1H-pyrazol-4-yl, 4,5-dihydro-1H-pyrazol-5-yl, 2,5-dihydro-1H-pyrazol-3-yl, 2,5-dihydro-1H-pyrazol-4-yl, 2,5-dihydro-1H-pyrazol-5-yl, 4,5-dihydroisoxazol-3-yl, 4,5-dihydroisoxazol-4-yl, 4,5-dihydroisoxazol-5-yl, 2,5-dihydroisoxazol-3-yl, 2,5-dihydroisoxazol-4-yl, 2,5-dihydroisoxazol-5-yl, 2,3-dihydroisoxazol-3-yl, 2,3-dihydroisoxazol-4-yl, 2,3-dihydroisoxazol-5-yl, 4,5-dihydroisothiazol-3-yl, 4,5-dihydroisothiazol-4-yl, 4,5-dihydroisothiazol-5-yl, 2,5-dihydroisothiazol-3-yl, 2,5-dihydroisothiazol-4-yl, 2,5-dihydroisothiazol-5-yl, 2,3-dihydroisothiazol-3-yl, 2,3-dihydroisothiazol-4-yl, 2,3-dihydroisothiazol-5-yl, $\Delta^3$-1,2-dithiol-3-yl, $\Delta^3$-1,2-dithiol-4-yl, $\Delta^3$-1,2-dithiol-5-yl, 4,5-dihydro-1H-imidazol-2-yl, 4,5-dihydro-1H-imidazol-4-yl, 4,5-dihydro-1H-imidazol-5-yl, 2,5-dihydro-1H-imidazol-2-yl, 2,5-dihydro-1H-imidazol-4-yl, 2,5-dihydro-1H-imidazol-5-yl, 2,3-dihydro-1H-imidazol-2-yl, 2,3-dihydro-1H-imidazol-4-yl, 4,5-dihydrooxazol-2-yl, 4,5-dihydrooxazol-4-yl, 4,5-dihydrooxazol-5-yl, 2,5-dihydrooxazol-2-yl, 2,5-dihydrooxazol-4-yl, 2,5-dihydrooxazol-5-yl, 2,3-dihydrooxazol-2-yl, 2,3-dihydrooxazol-4-yl, 2,3-dihydrooxazol-5-yl, 4,5-dihydrothiazol-2-yl, 4,5-dihydrothiazol-4-yl, 4,5-dihydrothiazol-5-yl, 2,5-dihydrothiazol-2-yl, 2,5-dihydrothiazol-4-yl, 2,5-dihydrothiazol-5-yl, 2,3-dihydrothiazol-2-yl, 2,3-dihydrothiazol-4-yl, 2,3-dihydrothiazol-5-yl, 1,3-dioxol-2-yl, 1,3-dioxol-4-yl, 1,3-dithiol-2-yl, 1,3-dithiol-4-yl, 1,3-oxathiol-2-yl, 1,3-oxathiol-4-yl, 1,3-oxathiol-5-yl, 1,2,3-$\Delta^2$-oxadiazolin-4-yl, 1,2,3-$\Delta^2$-oxadiazolin-5-yl, 1,2,4-$\Delta^4$-oxadiazolin-3-yl, 1,2,4-$\Delta^4$-oxadiazolin-5-yl, 1,2,4-$\Delta^2$-oxadiazolin-3-yl, 1,2,4-$\Delta^2$-oxadiazolin-5-yl, 1,2,4-$\Delta^3$-oxadiazolin-3-yl, 1,2,4-$\Delta^3$-oxadiazolin-5-yl, 1,3,4-$\Delta^2$-oxadiazolin-2-yl, 1,3,4-$\Delta^2$-oxadiazolin-5-yl, 1,3,4-$\Delta^3$-oxadiazolin-2-yl, 1,3,4-oxadiazolin-2-yl, 1,2,4-$\Delta^4$-thiadiazolin-3-yl, 1,2,4-$\Delta^4$-thiadiazolin-5-yl, 1,2,4-$\Delta^3$-thiadiazolin-3-yl, 1,2,4-$\Delta^3$-thiadiazolin-5-yl, 1,2,4-$\Delta^2$-thiadiazolin-3-yl, 1,2,4-$\Delta^2$-thiadiazolin-5-yl, 1,3,4-$\Delta^2$-thiadiazolin-2-yl, 1,3,4-$\Delta^2$-thiadiazolin-5-yl, 1,3,4-$\Delta^3$-thiadiazolin-2-yl, 1,3,4-thiadiazolin-2-yl, 1,2,3-$\Delta^2$-triazolin-4-yl, 1,2,3-$\Delta^2$-triazolin-5-yl, 1,2,4-$\Delta^2$-triazolin-3-yl, 1,2,4-$\Delta^2$-triazolin-5-yl, 1,2,4-$\Delta^3$-triazolin-3-yl, 1,2,4-$\Delta^3$-triazolin-5-yl, 1,2,4-$\Delta^1$-triazolin-2-yl, 1,2,4-triazolin-3-yl, 3H-1,2,4-dithiazol-5-yl, 2H-1,3,4-dithiazol-5-yl, 2H-1,3,4-oxathiazol-5-yl;

5-membered, unsaturated rings such as: 2-furyl, 3-furyl, 2-thienyl, 3-thienyl, pyrrol-2-yl, pyrrol-3-yl, pyrazol-3-yl, pyrazol-4-yl, isoxazol-3-yl, isoxazol-4-yl, isoxazol-5-yl, isothiazol-3-yl, isothiazol-4-yl, isothiazol-5-yl, imidazol-2-yl, imidazol-4-yl, oxazol-2-yl, oxazol-4-yl, oxazol-5-yl, thiazol-2-yl, thiazol-4-yl, thiazol-5-yl, 1,2,3-oxadiazol-4-yl, 1,2,3-oxadiazol-5-yl, 1,2,4-oxadiazol-3-yl, 1,2,4,-oxadiazol-5-yl, 1,3,4-oxadiazol-2-yl, 1,2,3-thiadiazol-4-yl, 1,2,3-thiadiazol-5-yl, 1,2,4-thiadiazol-3-yl, 1,2,4-thiadiazol-5-yl, 1,3,4-thiadiazolyl-2-yl, 1,2,3-triazol-4-yl, 1,2,4-triazol-3-yl, tetrazol-5-yl;

6-membered saturated rings such as: tetrahydropyran-2-yl, tetrahydropyran-3-yl, tetrahydropyran-4-yl, piperidin-2-yl, piperidin-3-yl, piperidin-4-yl, tetrahydrothiopyran-2-yl, tetrahydrothiopyran-3-yl, tetrahydrothiopyran-4-yl, 1,3-dioxan-2-yl, 1,3-dioxan-4-yl, 1,3-dioxan-5-yl, 1,4-dioxan-2-yl, 1,3-dithian-2-yl, 1,3-dithian-4-yl, 1,3-dithian-5-yl, 1,4-dithian-2-yl, 1,3-oxathian-2-yl, 1,3-oxathian-4-yl, 1,3-oxathian-5-yl, 1,3-oxathian-6-yl, 1,4-oxathian-2-yl, 1,4-oxathian-3-yl, 1,2-dithian-3-yl, 1,2-dithian-4-yl, hexahydropyrimidin-2-yl, hexahydropyrimidin-4-yl, hexahydropyrimidin-5-yl, hexahydropyrazin-2-yl, hexahydropyridazin-3-yl, hexahydropyridazin-4-yl, tetrahydro-1,3-oxazin-2-yl, tetrahydro-1,3-oxazin-4-yl, tetrahydro-1,3-oxazin-5-yl, tetrahydro-1,3-oxazin-6-yl, tetrahydro-1,3-thiazin-2-yl, tetrahydro-1,3-thiazin-4-yl, tetrahydro-1,3-thiazin-5-yl, tetrahydro-1,3-thiazin-6-yl, tetrahydro-1,4-thiazin-2-yl, tetrahydro-1,4-thiazin-3-yl, tetrahydro-1,4-oxazin-2-yl, tetrahydro-1,4-oxazin-3-yl, tetrahydro-1,2-oxazin-3-yl, tetrahydro-1,2-oxazin-4-yl, tetrahydro-1,2-oxazin-5-yl, tetrahydro-1,2-oxazin-6-yl;

6-membered partially saturated rings such as: 2H-3,4-dihydropyran-6-yl, 2H-3,4-dihydropyran-5-yl, 2H-3,4-dihydropyran-4-yl, 2H-3,4-dihydropyran-3-yl, 2H-3,4-dihydropyran-2-yl, 2H-3,4-dihydropyran-6-yl, 2H-3,4-dihydrothiopyran-5-yl, 2H-3,4-dihydrothiopyran-4-yl, 2H-3,4-dihydrothiopyran-3-yl, 2H-3,4-dihydropyran-2-yl, 1,2,3,4-tetrahydropyridin-6-yl, 1,2,3,4-tetrahydropyridin-5-yl, 1,2,3,4-tetrahydropyridin-4-yl, 1,2,3,4-tetrahydropyridin-3-yl, 1,2,3,4-tetrahydropyridin-2-yl, 2H-5,6-dihydropyran-2-yl, 2H-5,6-dihydropyran-3-yl, 2H-5,6-dihydropyran-4-yl, 2H-5,6-dihydropyran-5-yl, 2H-5,6-dihydropyran-6- yl, 2H-5,6-dihydrothiopyran-2-yl, 2H-5,6-dihydrothiopyran-3-yl, 2H-5,6-dihydrothiopyran-4-yl, 2H-5,6-dihydrothiopyran-5-yl, 2H-5,6-dihydrothiopyran-6-yl, 1,2,5,6-tetrahydropyridin-2-yl, 1,2,5,6-tetrahydropyridin-3-yl, 1,2,5,6-tetrahydropyridin-4-yl, 1,2,5,6-tetrahydropyridin-5-yl, 1,2,5,6-tetrahydropyridin-6-yl, 2,3,4,5-tetrahydropyridin-2-yl, 2,3,4,5-tetrahydropyridin-3-yl, 2,3,4,5-tetrahydropyridin-4-yl, 2,3,4,5-tetrahydropyridin-5-yl, 2,3,4,5-tetrahydropyridin-6-yl, 4H-pyran-2-yl, 4H-pyran-3-yl, 4H-pyran-4-yl, 4H-thiopyran-2-yl, 4H-thiopyran-3-yl, 4H-thiopyran-4-yl, 1,4-dihydropyridin-2-yl, 1,4-dihydropyridin-3-yl, 1,4-dihydropyridin-4-yl, 2H-pyran-2-yl, 2H-pyran-3-yl, 2H-pyran-4-yl, 2H-pyran-5-yl, 2H-pyran-6-yl, 2H-thiopyran-2-yl, 2H-thiopyran-3-yl, 2H-thiopyran-4-yl, 2H-thiopyran-5-yl, 2H-thiopyran-6-yl, 1,2-dihydropyridin-2-yl, 1,2-dihydropyridin-3-yl, 1,2-dihydropyridin-4-yl, 1,2-dihydropyridin-5-yl, 1,2-dihydropyridin-6-yl, 3,4-dihydropyridin-2-yl, 3,4-dihydropyridin-3-yl, 3,4-dihydropyridin-4-yl, 3,4-dihydropyridin-5-yl, 3,4-dihydropyridin-6-yl, 2,5-dihydropyridin-2-yl, 2,5-dihydropyridin-3-yl, 2,5-dihydropyridin-4-yl, 2,5-dihydropyridin-5-yl, 2,5-dihydropyridin-6-yl, 2,3-dihydropyridin-2-yl, 2,3-dihydropyridin-3-yl, 2,3-dihydropyridin-4-yl, 2,3-dihydropyridin-5-yl, 2,3-dihydropyridin-6-yl, 2H-5,6-dihydro-1,2-oxazin-3-yl, 2H-5,6-dihydro-1,2-oxazin-4-yl, 2H-5,6-dihydro-1,2-oxazin-5-yl, 2H-5,6-dihydro-1,2-oxazin-6-yl, 2H-5,6-dihydro-1,2-thiazin-3-yl, 2H-5,6-dihydro-1,2-thiazin-4-yl, 2H-5,6-dihydro-1,2-thiazin-5-yl, 2H-5,6-dihydro-1,2-thiazin-6-yl, 4H-5,6-dihydro-1,2-oxazin-3-yl, 4H-5,6-dihydro-1,2-oxazin-4-yl, 4H-5,6-dihydro-1,2-oxazin-5-yl, 4H-5,6-dihydro-1,2-oxazin-6-yl, 4H-5,6-dihydro-1,2-thiazin-3-yl, 4H-5,6-dihydro-1,2-thiazin-4-yl, 4H-5,6-dihydro-1,2-thiazin-5-yl, 4H-5,6-dihydro-1,2-thiazin-6-yl, 2H-3,6-dihydro-1,2-oxazin-3-yl, 2H-3,6-dihydro-1,2-oxazin-4-yl, 2H-3,6-dihydro-1,2-oxazin-5-yl, 2H-3,6-dihydro-1,2-oxazin-6-yl, 2H-3,6-dihydro-1,2-thiazin-3-yl, 2H-3,6-dihydro-1,2-thiazin-4-yl, 2H-3,6-dihydro-1,2-thiazin-5-yl, 2H-3,6-dihydro-1,2-thiazin-6-yl, 2H-3,4-dihydro-1,2-oxazin-3-yl, 2H-3,4-dihydro-1,2-oxazin-4-yl, 2H-3,4-dihydro-1,2-oxazin-5-yl, 2H-3,4-dihydro-1,2-oxazin-6-yl, 2H-3,4-dihydro-1,2-thiazin-3-yl, 2H-3,4-dihydro-1,2-thiazin-4-yl, 2H-3,4-dihydro-1,2-thiazin-5-yl, 2H-3,4-dihydro-1,2-thiazin-6-yl, 2,3,4,5-tetrahydropyridazin-3-yl, 2,3,4,5-tetrahydropyridazin-4-yl, 2,3,4,5-tetrahydropyridazin-5-yl, 2,3,4,5-tetrahydropyridazin-6-yl, 3,4,5,6-tetrahydropyridazin-3-yl, 3,4,5,6-tetrahydropyridazin-4-yl, 1,2,5,6-tetrahydropyridazin-3-yl, 1,2,5,6-tetrahydropyridazin-4-yl, 1,2,5,6-tetrahydropyridazin-5-yl, 1,2,5,6-tetrahydropyridazin-6-yl, 1,2,3,6-tetrahydropyridazin-3-yl, 1,2,3,6-tetrahydropyridazin-4-yl, 4H-5,6-dihydro-1,3-oxazin-2-yl, 4H-5,6-dihydro-1,3-oxazin-4-yl, 4H-5,6-dihydro-1,3-oxazin-5-yl, 4H-5,6-dihydro-1,3-oxazin-6-yl, 4H-5,6-dihydro-1,3-thiazin-2-yl, 4H-5,6-dihydro-1,3-thiazin-4-yl, 4H-5,6-dihydro-1,3-thiazin-5-yl, 4H-5,6-dihydro-1,3-thiazin-6-yl, 3,4,5,6-tetrahydropyrimidin-2-yl, 3,4,5,6-tetrahydropyrimidin-4-yl, 3,4,5,6-tetrahydropyrimidin-5-yl, 3,4,5,6-tetrahydropyrimidin-6-yl, 1,2,3,4-tetrahydropyrazin-2-yl, 1,2,3,4-tetrahydropyrazin-5-yl, 1,2,3,4-tetrahydropyrimidin-2-yl, 1,2,3,4-tetrahydropyrimidin-4-yl, 1,2,3,4-tetrahydropyrimidin-5-yl, 1,2,3,4-tetrahydropyrimidin-6-yl, 2,3-dihydro-1,4-thiazin-2-yl, 2,3-dihydro-1,4-thiazin-3-yl, 2,3-dihydro-1,4-thiazin-5-yl, 2,3-dihydro-1,4-thiazin-6-yl, 2H-1,2-oxazin-3-yl, 2H-1,2-oxazin-4-yl, 2H-1,2-oxazin-5-yl, 2H-1,2-oxazin-6-yl, 2H-1,2-thiazin-3-yl, 2H-1,2-thiazin-4-yl, 2H-1,2-thiazin-5-yl, 2H-1,2-thiazin-6-yl, 4H-1,2-oxazin-3-yl, 4H-1,2-oxazin-4-yl, 4H-1,2-oxazin-5-yl, 4H-1,2-oxazin-6-yl, 4H-1,2-thiazin-3-yl, 4H-1,2-thiazin-4-yl, 4H-1,2-thiazin-5-yl, 4H-1,2-thiazin-6-yl, 6H-1,2-oxazin-3-yl, 6H-1,2-oxazin-4-yl, 6H-1,2-oxazin-5-yl, 6H-1,2-oxazin-6-yl, 6H-1,2-thiazin-3-yl, 6H-1,2-thiazin-4-yl, 6H-1,2-thiazin-5-yl, 6H-1,2-thiazin-6-yl, 2H-1,3-oxazin-2-yl, 2H-1,3-oxazin-4-yl, 2H-1,3-oxazin-5-yl, 2H-1,3-oxazin-6-yl, 2H-1,3-thiazin-2-yl, 2H-1,3-thiazin-4-yl, 2H-1,3-thiazin-5-yl, 2H-1,3-thiazin-6-yl, 4H-1,3-oxazin-2-yl, 4H-1,3-oxazin-4-yl, 4H-1,3-oxazin-5-yl, 4H-1,3-oxazin-6-yl, 4H-1,3-thiazin-2-yl, 4H-1,3-thiazin-4-yl, 4H-1,3-thiazin-5-yl, 4H-1,3-thiazin-6-yl, 6H-1,3-oxazin-2-yl, 6H-1,3-oxazin-4-yl, 6H-1,3-oxazin-5-yl, 6H-1,3-oxazin-6-yl, 6H-1,3-thiazin-2-yl, 6H-1,3-oxazin-4-yl, 6H-1,3-oxazin-5-yl, 6H-1,3-thiazin-6-yl, 2H-1,4-oxazin-2-yl, 2H-1,4-oxazin-3-yl, 2H-1,4-oxazin-5-yl, 2H-1,4-oxazin-6-yl, 2H-1,4-thiazin-2-yl, 2H-1,4-thiazin-3-yl, 2H-1,4-thiazin-5-yl, 2H-1,4-thiazin-6-yl, 4H-1,4-oxazin-2-yl, 4H-1,4-oxazin-3-yl, 4H-1,4-thiazin-2-yl, 4H-1,4-thiazin-3-yl, 1,4-dihydropyridazin-3-yl, 1,4-dihydropyridazin-4-yl, 1,4-dihydropyridazin-5-yl, 1,4-dihydropyridazin-6-yl, 1,4-dihydropyrazin-2-yl, 1,2-dihydropyrazin-2-yl, 1,2-dihydropyrazin-3-yl, 1,2-dihydropyrazin-5-yl, 1,2-dihydropyrazin-6-yl, 1,4-dihydropyrimidin-2-yl, 1,4-dihydropyrimidin-4-yl, 1,4-dihydropyrimidin-5-yl, 1,4-dihydropyrimidin-6-yl, 3,4-dihydropyrimidin-2-yl, 3,4-dihydropyrimidin-4-yl, 3,4-dihydropyrimidin-5-yl or 3,4-dihydropyrimidin-6-yl;

6-membered unsaturated rings such as: pyridin-2-yl, pyridin-3-yl, pyridin-4-yl, pyridazin-3-yl, pyridazin-4-yl, pyrimidin-2-yl, pyrimidin-4-yl, pyrimidin-5-yl, pyrazin-2-yl, 1,3,5-triazin-2-yl, 1,2,4-triazin-3-yl, 1,2,4-triazin-5-yl, 1,2,4-triazin-6-yl, 1,2,4,5-tetrazin-3-yl;

it optionally being possible for the sulfur of the abovementioned heterocycles to be oxidized to S=O or S(=O)$_2$ and it being possible for a bicyclic ring system to be formed with a fused phenyl ring or with a $C_3$–$C_6$-carbocycle or with a further 5- to 6-membered heterocycle.

The following heterocyclyl radicals are preferably used:

5-membered unsaturated rings as mentioned above, in particular 2-furyl, 3-furyl, 2-thienyl, 3-thienyl, pyrrol-2-yl, pyrrol-3-yl, pyrazol-3-yl, pyrazol-4-yl, isoxazol-3-yl, isoxazol-4-yl, isoxazol-5-yl, imidazol-2-yl, imidazol-4-yl, oxazol-2-yl, oxazol-4-yl, oxazol-5-yl, thiazol-2-yl, thiazol-4-yl, thiazol-5-yl or 1,2,4-triazol-3-yl;

6-membered unsaturated rings as mentioned above, in particular pyridin-2-yl, pyridin-3-yl, pyridin-4-yl, pyrimidin-2-yl, pyrimidin-4-yl, pyrimidin-5-yl, pyrazin-2-yl or 1,3,5-triazin-2-yl;

all phenyl or heterocyclyl rings are preferably unsubstituted or have attached to them one to three halogen atoms and/or one nitro group, one cyano radical and/or one or two methyl, trifluoromethyl, methoxy or trifluoromethoxy substituents.

In view of the use of the compounds of the formula I according to the invention as herbicides, the variables preferably have the following meanings, in each case alone or in combination:

$R^1$, $R^2$ are nitro, halogen, cyano, $C_1$–$C_6$-alkyl, $C_1$–$C_6$-haloalkyl, $C_1$–$C_6$-alkoxy, $C_1$–$C_6$-haloalkoxy, $C_1$–$C_6$-alkylthio, $C_1$–$C_6$-haloalkylthio, $C_1$–$C_6$-alkylsulfinyl, $C_1$–$C_6$-haloalkylsulfinyl, $C_1$–$C_6$-alkylsulfonyl or $C_1$–$C_6$-haloalkylsulfonyl; especially preferably nitro, halogen such as, for example, chlorine and bromine, $C_1$–$C_6$-alkyl such as, for example, methyl and ethyl, $C_1$–$C_6$-alkoxy such as, for example, methoxy and ethoxy, $C_1$–$C_6$-haloalkyl such as, for example, difluoromethyl and trifluoromethyl, $C_1$–$C_6$-alkylthio such as, for example, methylthio and ethylthio, $C_1$–$C_6$-alkylsulfinyl such as, for example, methylsulfinyl and ethylsulfinyl, $C_1$–$C_6$-alkylsulfonyl such as, for example, methylsulfonyl, ethylsulfonyl and propylsulfonyl or $C_1$–$C_6$-haloalkylsulfonyl such as, for example, trifluoromethylsulfonyl and pentafluoroethylsulfonyl;

$R^3$ is hydrogen;

$R^4$ is hydrogen;

$R^5$, $R^6$ are hydrogen, halogen, cyano, nitro, $C_1$–$C_4$-alkyl, $C_1$–$C_4$-alkoxy-$C_1$–$C_4$-alkyl, $C_1$–$C_4$-alkoxycarbonyl-$C_1$–$C_4$-alkyl, $C_1$–$C_4$-alkylthio-$C_1$–$C_4$-alkyl, $C_1$–$C_4$-haloalkyl, $C_1$–$C_4$-cyanoalkyl, $C_3$–$C_8$-cycloalkyl, $C_1$–$C_4$-alkoxy, $C_1$–$C_4$-alkoxy-$C_2$–$C_4$-alkoxy, $C_1$–$C_4$-haloalkoxy, $C_1$–$C_4$-alkylthio, $C_1$–$C_4$-haloalkylthio, di($C_1$–$C_4$-alkyl)amino, $COR^8$, phenyl or benzyl, it being possible for the two last-mentioned substituents to be partially or fully halogenated and/or to have attached to them one to three of the following groups: nitro, cyano, $C_1$–$C_4$-alkyl, $C_1$–$C_4$-haloalkyl, $C_1$–$C_4$-alkoxy or $C_1$–$C_4$-haloalkoxy; or $R^5$ and $R^6$ together form a $C_2$–$C_6$-alkanediyl chain which can be mono- to tetrasubstituted by $C_1$–$C_4$-alkyl and/or can be interrupted by oxygen or an unsubstituted or $C_1$–$C_4$-alkyl-substituted nitrogen; $R^5$ is especially preferably hydrogen, halogen, cyano, nitro, $C_1$–$C_4$-alkyl, $C_1$–$C_4$-alkoxy-$C_1$–$C_4$-alkyl, $C_1$–$C_4$-alkoxycarbonyl-$C_1$–$C_4$-alkyl, $C_1$–$C_4$-alkylthio-$C_1$–$C_4$-alkyl, $C_1$–$C_4$-haloalkyl, $C_1$–$C_4$-cyanoalkyl, $C_3$–$C_8$-cycloalkyl, $C_1$–$C_4$-alkoxy, $C_1$–$C_4$-alkoxy-$C_2$–$C_4$-alkoxy, $C_1$–$C_4$-haloalkoxy, $C_1$–$C_4$-alkylthio, $C_1$–$C_4$-haloalkylthio, di($C_1$–$C_4$-alkyl)amino, $COR^8$, phenyl or benzyl, it being possible for the two last-mentioned substituents to be partially or fully halogenated and/or to have attached to them one to three of the following groups: nitro, cyano, $C_1$–$C_4$-alkyl, $C_1$–$C_4$-haloalkyl, $C_1$–$C_4$-alkoxy or $C_1$–$C_4$-haloalkoxy; $R^6$ is especially preferably hydrogen or $C_1$–$C_4$-alkyl; particularly preferably $R^5$ is hydrogen, $C_1$–$C_4$-alkyl, $C_1$–$C_4$-haloalkyl, $C_1$–$C_4$-alkoxycarbonyl or $CONR^9R^{10}$; particularly preferably $R^6$ is hydrogen or $C_1$–$C_4$-alkyl; very especially preferably $R^5$ is hydrogen or $C_1$–$C_4$-alkyl, particularly hydrogen; very especially preferably $R^6$ is hydrogen;

$R^7$ is halogen, $C_1$–$C_6$-alkyl, $C_1$–$C_6$-haloalkyl, $C_1$–$C_6$-alkoxy, $C_1$–$C_6$-alkylthio, $C_1$–$C_6$-alkylsulfinyl, $C_1$–$C_6$-alkylsulfonyl, amino, $C_1$–$C_6$-alkylamino, di($C_1$–$C_6$-alkyl)amino, di($C_1$–$C_4$-alkoxy)methyl or $COR^8$; especially preferably $C_1$–$C_4$-alkyl such as, for example, methyl, ethyl, 1-methylethyl or 1,1-dimethylethyl, $C_1$–$C_4$-alkylcarbonyl such as, for example, methylcarbonyl or ethylcarbonyl, hydroxycarbonyl or $C_1$–$C_4$-alkoxycarbonyl such as, for example, methoxycarbonyl or ethoxycarbonyl; particularly preferably $C_1$–$C_4$-alkyl such as, for example, methyl, ethyl, 1-methylethyl or 1,1-dimethylethyl, hydroxycarbonyl or $C_1$–$C_4$-alkoxycarbonyl; very especially preferably $C_1$–$C_4$-alkyl such as, for example, methyl, ethyl, 1-methylethyl or 1,1-dimethylethyl;

$R^8$ is $C_1$–$C_4$-alkyl, hydroxyl, $C_1$–$C_4$-alkoxy or $NR^9R^{10}$;

$R^9$ is hydrogen or $C_1$–$C_4$-alkyl;

$R^{10}$ is $C_1$–$C_4$-alkyl;

$R^{12}$ is hydroxyl, $OR^{19}$, $SR^{19}$, $SOR^{20}$ or $SO_2R^{20}$; particularly hydroxyl, $OR^{19}$ or $SR^{19}$; especially preferably hydroxyl;

$R^{13}$, $R^{17}$ are hydrogen, $C_1$–$C_4$-alkyl or $C_1$–$C_4$-alkylthio; particularly hydrogen, methyl or methylthio; especially preferably hydrogen or methyl, particularly preferably hydrogen;

$R^{14}$, $R^{16}$, $R^{18}$ are hydrogen or methyl;

$R^{15}$ is hydrogen, hydroxyl, $C_1$–$C_6$-alkyl or di($C_1$–$C_6$-alkoxy)methyl; particularly hydrogen or $C_1$–$C_4$-alkyl; or $R^{13}$ and $R^{14}$ or $R^{14}$ and $R^{15}$ or $R^{15}$ and $R^{18}$ or $R^{14}$ and $R^{18}$ or $R^{17}$ and $R^{18}$ together are $C_1$–$C_5$-alkanediyl which can have attached to it one, two or three substituents selected from among halogen, cyano, $C_1$–$C_4$-alkyl, $C_1$–$C_4$-haloalkyl or $C_1$–$C_4$-alkoxycarbonyl; or $R^{15}$ and $R^{16}$ together are an oxygen atom;

$R^{19}$ is $C_1$–$C_6$-alkyl, $C_1$–$C_{20}$-alkylcarbonyl, preferably $C_1$–$C_6$-alkylcarbonyl, $C_1$–$C_6$-alkoxycarbonyl, $C_1$–$C_6$-alkylthiocarbonyl, it being possible for the abovementioned alkyl and alkoxy radicals to be partially or fully halogenated and/or to have attached to them one, two or three substituents selected from among cyano, $C_1$–$C_4$-alkoxy, $C_1$–$C_4$-alkylthio, $C_1$–$C_4$-alkylcarbonyl, $C_1$–$C_4$-alkoxycarbonyl or $C_3$–$C_6$-cycloalkyl; phenyl, phenyl-$C_1$–$C_4$-alkyl, phenylcarbonyl-$C_1$–$C_4$-alkyl, phenylcarbonyl, phenoxycarbonyl, heterocyclyl, heterocyclyl-$C_1$–$C_4$-alkyl, heterocyclylcarbonyl-$C_1$–$C_4$-alkyl, heterocyclyloxycarbonyl, it being possible for the phenyl or heterocyclyl radical of the abovementioned radicals to be partially or fully halogenated and/or to have attached to it one, two or three substituents selected from among nitro, cyano, $C_1$–$C_4$-alkyl, $C_1$–$C_4$-haloalkyl, $C_1$–$C_4$-alkoxy or $C_1$–$C_4$-haloalkoxy;

$R^{20}$ is $C_1$–$C_6$-alkyl which can be partially or fully halogenated and/or can have attached to it one, two or three substituents selected from among cyano, $C_1$–$C_4$-alkoxy, $C_1$–$C_4$-alkylthio, $C_1$–$C_4$-alkylcarbonyl, $C_1$–$C_4$-alkoxycarbonyl or $C_3$–$C_6$-cycloalkyl; phenyl, phenyl-$C_1$–$C_4$-alkyl, phenylcarbonyl-$C_1$–$C_4$-alkyl, heterocyclyl, heterocyclyl-$C_1$–$C_4$-alkyl or heterocyclylcarbonyl-$C_1$–$C_4$-alkyl, it being possible for the phenyl or heterocyclyl radical of the abovementioned radicals to be partially or fully halogenated and/or to have attached to it one, two or three substituents selected from among nitro, cyano, $C_1$–$C_4$-alkyl, $C_1$–$C_4$-haloalkyl, $C_1$–$C_4$-alkoxy or $C_1$–$C_4$-haloalkoxy.

The following embodiments of the 3-(4,5-dihydroisoxazol-5-yl)benzoylcyclohexenones of the formula I must be emphasized:

1. In a preferred embodiment of the 3-(4,5-dihydroisoxazol-5-yl)benzoylcyclohexenones of the formula I,
   $R^1$ is nitro, halogen, $C_1$–$C_6$-alkyl, $C_1$–$C_6$-haloalkyl, $C_1$–$C_6$-alkoxy or $C_1$–$C_6$-haloalkoxy; especially preferably nitro, halogen such as 30 chlorine or bromine, $C_1$–$C_4$-alkyl such as methyl or ethyl, $C_1$–$C_4$-haloalkyl such as difluoromethyl or trifluoromethyl, $C_1$–$C_4$-alkoxy such as methoxy or ethoxy, or $C_1$–$C_4$-haloalkoxy such as difluoromethoxy or trifluoromethoxy; particularly preferably halogen such as chlorine or bromine, $C_1$–$C_4$-alkyl such as methyl or ethyl or $C_1$–$C_4$-alkoxy such as methoxy or ethoxy; very especially preferably halogen, such as chlorine or bromine or $C_1$–$C_4$-alkyl such as methyl or ethyl;
   $R^2$ is halogen, $C_1$–$C_6$-haloalkyl, $C_1$–$C_6$-alkylthio, $C_1$–$C_6$-haloalkylthio, $C_1$–$C_6$-alkylsulfinyl, $C_1$–$C_6$-haloalkylsulfinyl, $C_1$–$C_6$-alkylsulfonyl or $C_1$–$C_6$-haloalkylsulfonyl; especially preferably halogen such as fluorine or chlorine, $C_1$–$C_4$-haloalkyl such as difluoromethyl or trifluoromethyl, or $C_1$–$C_4$-alkylsulfonyl such as methylsulfonyl or ethylsulfonyl; particularly preferably halogen such as fluorine or chlorine, or $C_1$–$C_4$-alkylsulfonyl such as methylsulfonyl or ethylsulfonyl; very especially preferably $C_1$–$C_4$-alkylsulfonyl such as methylsulfonyl or ethylsulfonyl;
2. In a further preferred embodiment of the 3-(4,5-dihydroisoxazol-5-yl)benzoylcyclohexenones of the formula I,
   $R^3$ is hydrogen.
3. In a further preferred embodiment of the 3-(4,5-dihydroisoxazol-5-yl)benzoylcyclohexenones of the formula I,
   $R^3$ is halogen or $C_1$–$C_4$-alkyl; particularly preferably chlorine or methyl.
4. In a further embodiment of the 3-(4,5-dihydroisoxazol-5-yl)benzoylcyclohexenones of the formula I,
   $R^4$ is hydrogen.
5. In a further embodiment of the 3-(4,5-dihydroisoxazol-5-yl)benzoylcyclohexenones of the formula I,
   $R^4$ is hydrogen;
   $R^5$ is hydrogen, halogen, cyano, nitro, $C_1$–$C_4$-alkyl, $C_1$–$C_4$-alkoxy-$C_1$–$C_4$-alkyl, $C_1$–$C_4$-alkoxycarbonyl-$C_1$–$C_4$-alkyl, $C_1$–$C_4$-alkylthio-$C_1$–$C_4$-alkyl, $C_1$–$C_4$-haloalkyl, $C_1$–$C_4$-cyanoalkyl, $C_3$–$C_8$-cycloalkyl, $C_1$–$C_4$-alkoxy, $C_1$–$C_4$-alkoxy-$C_2$–$C_4$-alkoxy, $C_1$–$C_4$-haloalkoxy, $C_1$–$C_4$-alkylthio, $C_1$–$C_4$-haloalkylthio, di($C_1$–$C_4$-alkyl)amino, $C_1$–$C_4$-alkylcarbonyl, $C_1$–$C_4$-alkoxycarbonyl, $CONR^9R^{10}$, phenyl or benzyl, it being possible for the two last-mentioned substituents to be partially or fully halogenated and/or to have attached to them one to three of the following groups: nitro, cyano, $C_1$–$C_4$-alkyl, $C_1$–$C_4$-haloalkyl, $C_1$–$C_4$-alkoxy or $C_1$–$C_4$-haloalkoxy; especially preferably hydrogen, $C_1$–$C_4$-alkyl, $C_1$–$C_4$-haloalkyl, $C_1$–$C_4$-alkoxycarbonyl or $CONR^9R^{10}$; particularly preferably hydrogen or $C_1$–$C_4$-alkyl such as methyl or ethyl; very especially preferably hydrogen;
   $R^6$ is hydrogen or $C_1$–$C_4$-alkyl such as methyl or ethyl; especially preferably hydrogen.
6. In a further preferred embodiment of the 3-(4,5-dihydroisoxazol-5-yl)benzoylcyclohexenones of the formula I,
   $R^7$ is halogen, $C_1$–$C_6$-alkyl, $C_1$–$C_6$-haloalkyl, $C_1$–$C_6$-alkoxy, $C_1$–$C_6$-alkylthio, $C_1$–$C_6$-alkylsulfinyl, $C_1$–$C_6$-alkylsulfonyl, amino, $C_1$–$C_6$-alkylamino, di($C_1$–$C_6$-alkyl)amino, di($C_1$–$C_6$-alkoxy)methyl, formyl, $C_1$–$C_4$-alkylcarbonyl, $C_1$–$C_4$-haloalkylcarbonyl, hydroxycarbonyl, $C_1$–$C_4$-alkoxycarbonyl, $C_1$–$C_4$-haloalkoxycarbonyl or $CONR^9R^{10}$;
   especially preferably halogen such as chlorine or bromine, $C_1$–$C_4$-alkyl such as methyl, ethyl, 1-methylethyl or 1,1-dimethylethyl, $C_1$–$C_4$-alkoxy, such as methoxy or ethoxy, $C_1$–$C_4$-alkylthio such as methylthio or ethylthio, $C_1$–$C_4$-alkylsulfinyl such as methylsulfinyl or ethylsulfinyl, $C_1$–$C_4$-alkylsulfonyl such as methylsulfonyl or ethylsulfonyl, amino, $C_1$–$C_4$-alkylamino such as methylamino or ethylamino, di($C_1$–$C_4$-alkyl)amino such as dimethylamino or diethylamino, di($C_1$–$C_4$-alkoxy)methyl such as dimethoxymethyl or diethoxymethyl, $C_1$–$C_4$-alkylcarbonyl such as methylcarbonyl or ethylcarbonyl, hydroxycarbonyl, $C_1$–$C_4$-alkoxycarbonyl such as methoxycarbonyl or ethoxycarbonyl or $CONR^9R^{10}$;
   particularly preferably $C_1$–$C_4$-alkyl such as methyl, ethyl, 1-methylethyl or 1,1-dimethylethyl, $C_1$–$C_4$-alkylcarbonyl such as methylcarbonyl or ethylcarbonyl, hydroxycarbonyl or $C_1$–$C_4$-alkoxycarbonyl such as methoxycarbonyl or ethoxycarbonyl;
   very especially preferably $C_1$–$C_4$-alkyl such as methyl, ethyl, 1-methylethyl or 1,1-dimethylethyl, hydroxycarbonyl or $C_1$–$C_4$-alkoxycarbonyl or ethoxycarbonyl;
   very particularly preferably $C_1$–$C_4$-alkyl such as methyl, ethyl, 1-methylethyl or 1,1-dimethylethyl.
7. In a further preferred embodiment of the 3-(4,5-dihydroisoxazol-5-yl)benzoylcyclohexenones of the formula I,
   $R^{12}$ is hydroxyl, $OR^{19}$ or $SR^{19}$; and
   $R^{19}$ is $C_1$–$C_6$-alkyl, $C_1$–$C_{20}$-alkylcarbonyl, $C_1$–$C_6$-alkoxycarbonyl, $C_1$–$C_6$-alkylthiocarbonyl, it being possible for the alkyl and alkoxy radicals to be partially or fully halogenated and/or to have attached to them one, two or three substituents selected from among cyano, $C_1$–$C_4$-alkoxy, $C_1$–$C_4$-alkylthio, $C_1$–$C_4$-alkylcarbonyl, $C_1$–$C_4$-alkoxycarbonyl or $C_3$–$C_6$-cycloalkyl;
   phenyl, phenyl-$C_1$–$C_4$-alkyl, phenylcarbonyl-$C_1$–$C_4$-alkyl, phenylcarbonyl, phenoxycarbonyl, heterocyclyl, heterocyclyl-$C_1$–$C_4$-alkyl, heterocyclylcarbonyl-$C_1$–$C_4$-alkyl, heterocyclyloxycarbonyl, it being possible for the phenyl or heterocyclyl radical of the abovementioned radicals to be partially or fully halogenated and/or to have attached to it one, two or three substituents selected from among nitro, cyano, $C_1$–$C_4$-alkyl, $C_1$–$C_4$-haloalkyl, $C_1$–$C_4$-alkoxy or $C_1$–$C_4$-haloalkoxy.
   Heterocyclyl (alone or in combination) is preferably a 5-membered unsaturated ring or a 6-membered unsaturated ring, in particular pyridin-2-yl or pyridin-3-yl.
   Especially preferably heterocyclyl (alone or in combination) is 5-membered unsaturated rings wth a hetero atom such as
   2-furyl, 3-furyl, 2-thienyl, 3-thienyl, pyrrol-2-yl or pyrrol-3-yl;
   very especially preferably heterocyclyl is 2-thienyl or 3-thienyl.
8. In a further preferred embodiment of the 3-(4,5-dihydroisoxazol-5-yl)benzoylcyclohexenones of the formula I, $R^{12}$ is hydroxyl.
9. In a further preferred embodiment of the 3-(4,5-dihydroisoxazol-5-yl)benzoylcyclohexenones of the formula I, $R^{13}$ and $R^{17}$ are hydrogen, $C_1$–$C_4$-alkyl or $C_1$–$C_4$-alkylthio;

$R^{14}$, $R^{16}$, $R^{18}$ are hydrogen or methyl;

$R^{15}$ is hydrogen, hydroxyl, $C_1$–$C_6$-alkyl or di($C_1$–$C_6$-alkoxy)methyl; or $R^{13}$ and $R^{14}$ or $R^{14}$ and $R^{15}$ or $R^{15}$ and $R^{16}$ or $R^{14}$ and $R^{18}$ or $R^{17}$ and $R^{18}$ together are $C_1$–$C_5$-alkanediyl which can have attached to it one, two or three substituents selected from among halogen, cyano, $C_1$–$C_4$-alkyl, $C_1$–$C_4$-haloalkyl or $C_1$–$C_4$-alkoxycarbonyl; or $R^{15}$ and $R^{16}$ together are an oxygen atom.

Particularly preferably, $R^{13}$, $R^{17}$ are hydrogen or $C_1$–$C_4$-alkyl;

$R^{14}$, $R^{16}$, $R^{18}$ are hydrogen or methyl;

$R^{15}$ is hydrogen, $C_1$–$C_6$-alkyl or di($C_1$–$C_6$-alkoxy)methyl; very especially preferably hydrogen or $C_1$–$C_6$-alkyl; or $R^{14}$ and $R^{18}$ together are $C_1$–$C_5$-alkanediyl which can have attached to it one, two or three substituents selected from among halogen, cyano, $C_1$–$C_4$-alkyl, $C_1$–$C_4$-haloalkyl or $C_1$–$C_4$-alkoxycarbonyl; or $R^{15}$ and $R^{16}$ together are an oxygen atom.

Very particularly especially preferred are the 3-(4,5-dihydroisoxazol-5-yl)benzoylcyclohexenones of the formula Ia1 ($\equiv$ I where $R^1$=Cl; $R^2$=SO$_2$CH$_3$; $R^3$, $R^4$, $R^{15}$ to $R^{18}$=H; $R^{12}$=OH), in particular the compounds Ia1.1 to Ia1.64, the definitions of radicals $R^1$ to $R^{14}$ having a special meaning for the compounds according to the invention, not only in combination with each other, but also in each case by themselves.

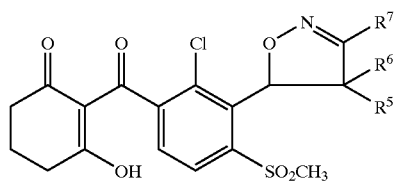

Ia1

TABLE 1

| No. | $R^5$ | $R^6$ | $R^7$ |
|---|---|---|---|
| Ia1.1 | H | H | CH$_3$ |
| Ia1.2 | Cl | H | CH$_3$ |
| Ia1.3 | Br | H | CH$_3$ |
| Ia1.4 | CN | H | CH$_3$ |
| Ia1.5 | NO$_2$ | H | CH$_3$ |
| Ia1.6 | CH$_3$ | H | CH$_3$ |
| Ia1.7 | CH$_2$CH$_3$ | H | CH$_3$ |
| Ia1.8 | CH(CH$_3$)$_2$ | H | CH$_3$ |
| Ia1.9 | C(CH$_3$)$_3$ | H | CH$_3$ |
| Ia1.10 | CHO | H | CH$_3$ |
| Ia1.11 | CH=NOH | H | CH$_3$ |
| Ia1.12 | CH=NOCH$_3$ | H | CH$_3$ |
| Ia1.13 | CH=NOCH$_2$CH$_3$ | H | CH$_3$ |
| Ia1.14 | COCH$_3$ | H | CH$_3$ |
| Ia1.15 | C(=NOH)CH$_3$ | H | CH$_3$ |
| Ia1.16 | C(=NOCH$_3$)CH$_3$ | H | CH$_3$ |
| Ia1.17 | C(=NOCH$_2$CH$_3$)CH$_3$ | H | CH$_3$ |
| Ia1.18 | CH=NN(CH$_3$)$_2$ | H | CH$_3$ |
| Ia1.19 | C[=NN(CH$_3$)$_2$]CH$_3$ | H | CH$_3$ |
| Ia1.20 | COOH | H | CH$_3$ |
| Ia1.21 | COOCH$_3$ | H | CH$_3$ |
| Ia1.22 | COOCH$_2$CH$_3$ | H | CH$_3$ |
| Ia1.23 | OCH$_3$ | H | CH$_3$ |
| Ia1.24 | OCH$_2$CH$_3$ | H | CH$_3$ |

TABLE 1-continued

| No. | $R^5$ | $R^6$ | $R^7$ |
|---|---|---|---|
| Ia1.25 | SCH$_3$ | H | CH$_3$ |
| Ia1.26 | CH$_2$F | H | CH$_3$ |
| Ia1.27 | CHF$_2$ | H | CH$_3$ |
| Ia1.28 | CF$_3$ | H | CH$_3$ |
| Ia1.29 | CF$_2$CF$_3$ | H | CH$_3$ |
| Ia1.30 | CH$_2$Cl | H | CH$_3$ |
| Ia1.31 | CH$_2$CN | H | CH$_3$ |
| Ia1.32 | CH$_2$—CH$_2$ | | CH$_3$ |
| Ia1.33 | CH$_2$—CH$_2$—CH$_2$ | | CH$_3$ |
| Ia1.34 | CH$_2$—CH$_2$—CH$_2$—CH$_2$ | | CH$_3$ |
| Ia1.35 | CH$_2$—CH$_2$—CH$_2$—CH$_2$—CH$_2$ | | CH$_3$ |
| Ia1.36 | CH$_3$ | CH$_3$ | CH$_3$ |
| Ia1.37 | CH$_3$ | CH$_2$CH$_3$ | CH$_3$ |
| Ia1.38 | CF$_3$ | COCH$_3$ | CH$_3$ |
| Ia1.39 | CF$_3$ | COOCH$_3$ | CH$_3$ |
| Ia1.40 | CN | COCH$_3$ | CH$_3$ |
| Ia1.41 | CN | COOCH$_3$ | CH$_3$ |
| Ia1.42 | CN | CN | CH$_3$ |
| Ia1.43 | COCH$_3$ | COCH$_3$ | CH$_3$ |
| Ia1.44 | COCH$_3$ | COOCH$_3$ | CH$_3$ |
| Ia1.45 | H | H | CH$_2$CH$_3$ |
| Ia1.46 | H | H | CH(CH$_3$)$_2$ |
| Ia1.47 | H | H | C(CH$_3$)$_3$ |
| Ia1.48 | H | H | Cl |
| Ia1.49 | H | H | OCH$_3$ |
| Ia1.50 | H | H | SCH$_3$ |
| Ia1.51 | H | H | SOCH$_3$ |
| Ia1.52 | H | H | SO$_2$CH$_3$ |
| Ia1.53 | H | H | CN |
| Ia1.54 | H | H | CHO |
| Ia1.55 | H | H | CH=NOH |
| Ia1.56 | H | H | CH=NOCH$_3$ |
| Ia1.57 | H | H | CH=NOCH$_2$CH$_3$ |
| Ia1.58 | H | H | COCH$_3$ |
| Ia1.59 | H | H | C(=NOH)CH$_3$ |
| Ia1.60 | H | H | C(=NOCH$_3$)CH$_3$ |
| Ia1.61 | H | H | COOH |
| Ia1.62 | H | H | COOCH$_3$ |
| Ia1.63 | H | H | COOCH$_2$CH$_3$ |
| Ia1.64 | H | H | CH(OCH$_2$CH$_3$)$_2$ |

Equally particularly preferred are the compounds Ia2., especially the compounds Ia2.1–Ia2.64, which differ from the compounds Ia1.1–Ia1.64 by the fact that $R^{15}$ is methyl.

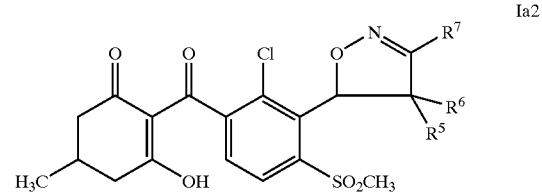

Ia2

Equally particularly preferred are the compounds Ia3., especially 10 the compounds Ia3.1–Ia3.64, which differ from the compounds Ia1.1–Ia1.64 by the fact that $R^{15}$ and $R^{16}$ are methyl.

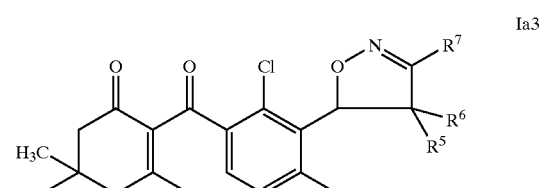

Ia3

Equally particularly preferred are the compounds Ia4., especially the compounds Ia4.1–Ia4.64, which differ from the compounds Ia1.1–Ia1.64 by the fact that $R^{13}$ and $R^{17}$ are methyl.

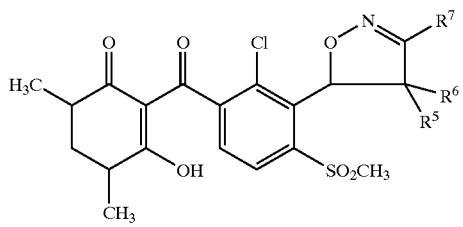

Ia4

Equally particularly preferred are the compounds Ia5., especially the compounds Ia5.1–Ia5.64, which differ from the compounds Ia1.1–Ia1.64 by the fact that $R^{13}$ is methylthio and $R^{14}$ is methyl.

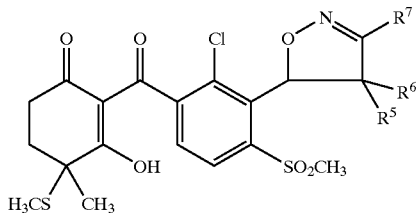

Ia5

Equally particularly preferred are the compounds Ia6., especially the compounds Ia6.1–Ia6.64, which differ from the compounds Ia1.1–Ia1.64 by the fact that $R^{14}$ and $R^{18}$ together are ethane-1,2-diyl.

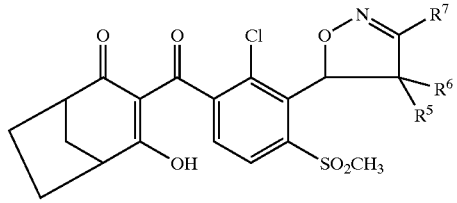

Ia6

Equally particularly preferred are the compounds Ia7., especially the compounds Ia7.1–Ia7.64, which differ from the compounds Ia1.1–Ia1.64 by the fact that $R^{13}$, $R^{14}$, $R^{17}$ and $R^{18}$ are methyl and $R^{15}$ and $R^{16}$ are oxygen.

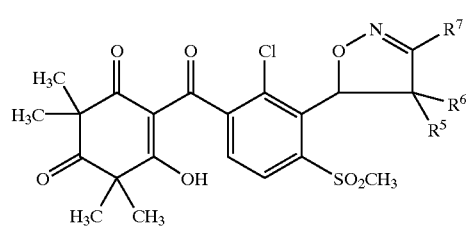

Ia7

Equally particularly preferred are the compounds Ia8., especially the compounds Ia8.1–Ia8.64, which differ from the compounds Ia1.1–Ia1.64 by the fact that $R^{15}$ is hydroxyl.

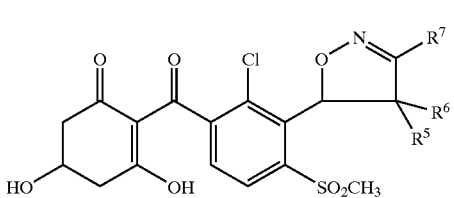

Ia8

Equally particularly preferred are the compounds Ia9., especially the compounds Ia9.1–Ia9.64, which differ from the compounds Ia1.1–Ia1.64 by the fact that $R^1$ is methyl.

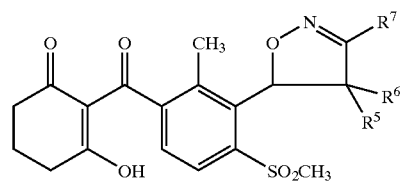

Ia9

Equally particularly preferred are the compounds Ia10., especially the compounds Ia10.1–Ia10.64, which differ from the compounds Ia1.1–Ia1.64 by the fact that $R^1$ and $R^{15}$ are methyl.

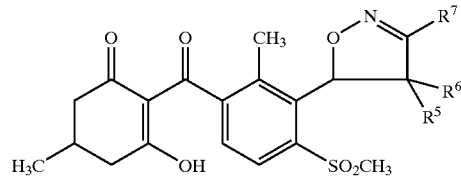

Ia10

Equally particularly preferred are the compounds Ia11., especially the compounds Ia11.1–Ia11.64, which differ from the compounds Ia1.1–Ia1.64 by the fact that $R^1$, $R^{15}$ and $R^{16}$ are methyl.

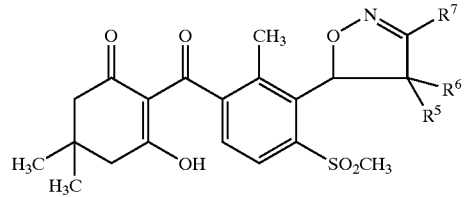

Ia11

Equally particularly preferred are the compounds Ia12., especially the compounds Ia12.1–Ia12.64, which differ from the compounds Ia1.1–Ia1.64 by the fact that $R^1$, $R^{13}$ and $R^{17}$ are methyl.

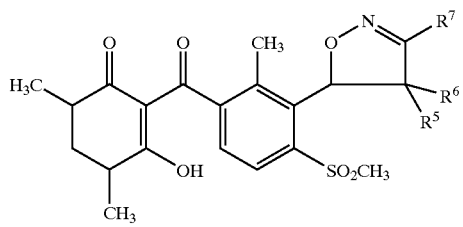

Ia12

Equally particularly preferred are the compounds Ia13., especially the compounds Ia13.1–Ia13.64, which differ from the compounds Ia1.1–Ia1.64 by the fact that $R^1$ and $R^{14}$ are methyl and $R^{13}$ is methylthio.

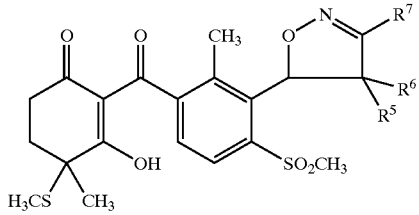

Ia13

Equally particularly preferred are the compounds Ia14., especially the compounds Ia14.1–Ia14.64, which differ from the compounds Ia1.1–Ia1.64 by the fact that $R^1$ is methyl and $R^{14}$ and $R^{18}$ together are ethane-1,2-diyl.

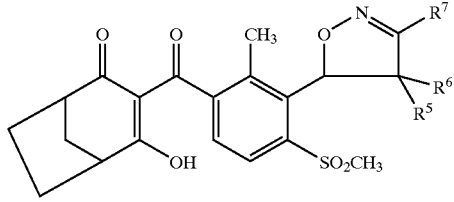

Ia14

Equally particularly preferred are the compounds Ia15., especially the compounds Ia15.1–Ia15.64, which differ from the compounds Ia1.1–Ia1.64 by the fact that $R^1$, $R^{13}$, $R^{14}$, $R^{17}$ and $R^{18}$ are methyl and $R^{15}$ and $R^{16}$ are oxygen.

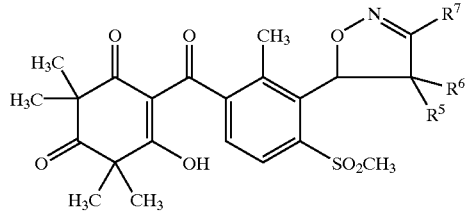

Ia15

Equally particularly preferred are the compounds Ia16., especially the compounds Ia16.1–Ia16.64, which differ from the compounds Ia1.1–Ia1.64 by the fact that $R^1$ is methyl and $R^{15}$ is hydroxyl.

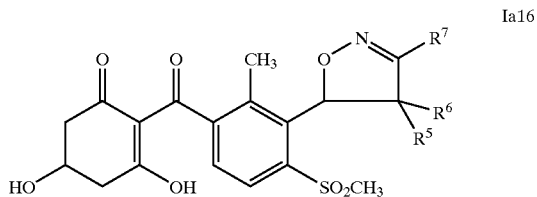

Ia16

Equally particularly preferred are the compounds Ia17., especially the compounds Ia17.1–Ia17.64, which differ from the compounds Ia1.1–Ia1.64 by the fact that $R^1$ is trifluoromethyl.

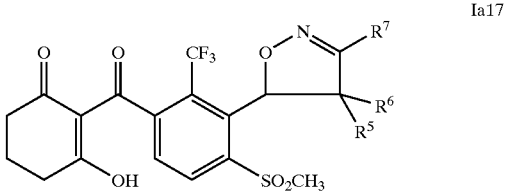

Ia17

Equally particularly preferred are the compounds Ia18., especially the compounds Ia18.1–Ia18.64, which differ from the compounds Ia1.1–Ia1.64 by the fact that $R^1$ is trifluoromethyl and $R^{15}$ is methyl.

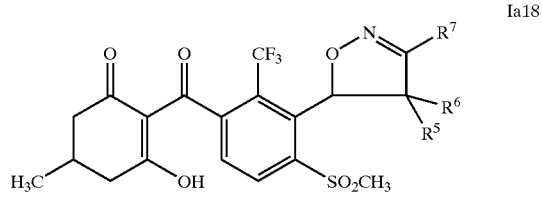

Ia18

Equally particularly preferred are the compounds Ia19., especially the compounds Ia19.1–Ia19.64, which differ from the compounds Ia1.1–Ia1.64 by the fact that $R^1$ is trifluoromethyl and $R^{15}$ and $R^{16}$ are methyl.

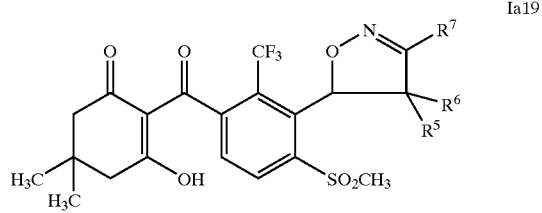

Ia19

Equally particularly preferred are the compounds Ia20., especially the compounds Ia20.1–Ia20.64, which differ from the compounds Ia1.1–Ia1.64 by the fact that $R^1$ is trifluoromethyl and $R^{13}$ and $R^{17}$ are methyl.

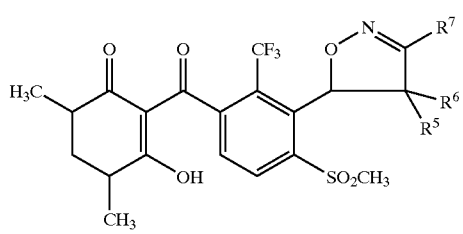

Ia20

Equally particularly preferred are the compounds Ia21., especially the compounds Ia21.1–Ia21.64, which differ from the compounds Ia1.1–Ia1.64 by the fact that $R^1$ is trifluoromethyl, $R^{13}$ is methylthio and $R^{14}$ is methyl.

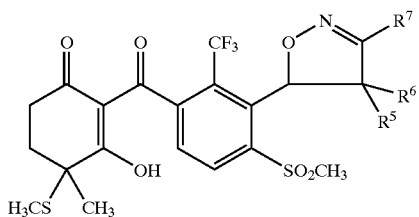

Ia21

Equally particularly preferred are the compounds Ia22., especially the compounds Ia22.1–Ia22.64, which differ from the compounds Ia1.1–Ia1.64 by the fact that $R^1$ is trifluoromethyl, $R^{14}$ and $R^{18}$ together are ethane-1,2-diyl.

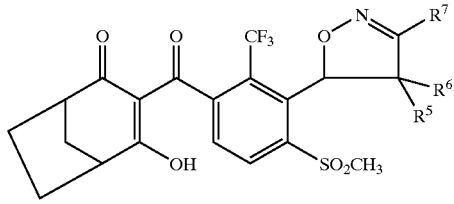

Ia22

Equally particularly preferred are the compounds Ia23., especially the compounds Ia23.1–Ia23.64, which differ from the compounds Ia1.1–Ia1.64 by the fact that $R^1$ is trifluoromethyl, $R^{13}$, $R^{14}$, $R^{17}$ and $R^{18}$ are methyl and $R^{16}$ is oxygen.

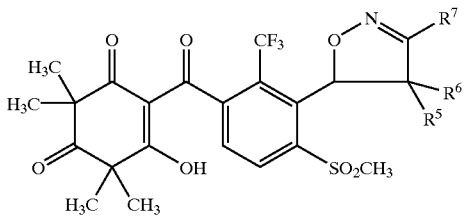

Ia23

Equally particularly preferred are the compounds Ia24., especially the compounds Ia24.1–Ia24.64, which differ from the compounds Ia1.1–Ia1.64 by the fact that $R^1$ is trifluoromethyl and $R^{15}$ is hydroxyl.

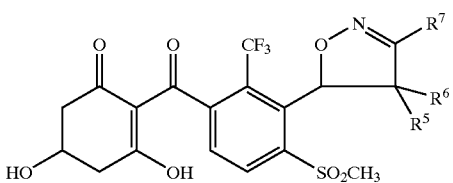

Ia24

Equally particularly preferred are the compounds Ia25., especially the compounds Ia25.1–Ia25.64, which differ from the compounds Ia1.1–Ia1.64 by the fact that $R^1$ is methoxy.

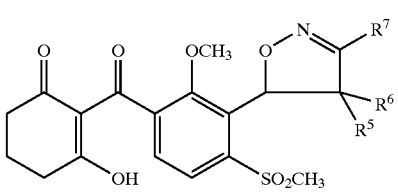

Ia25

Equally particularly preferred are the compounds Ia26., especially the compounds Ia26.1–Ia26.64, which differ from the compounds Ia1.1–Ia1.64 by the fact that $R^1$ is methoxy and $R^{15}$ is methyl.

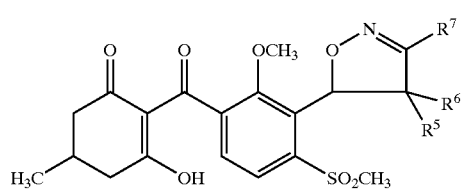

Ia26

Equally particularly preferred are the compounds Ia27., especially the compounds Ia27.1–Ia27.64, which differ from the compounds Ia1.1–Ia1.64 by the fact that $R^1$ is methoxy and $R^{15}$ and $R^{16}$ are methyl.

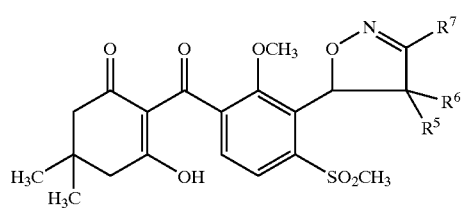

Ia27

Equally particularly preferred are the compounds Ia28., especially the compounds Ia28.1–Ia28.64, which differ from the compounds Ia1.1–Ia1.64 by the fact that $R^1$ is methoxy and $R^{13}$ and $R^{17}$ are methyl.

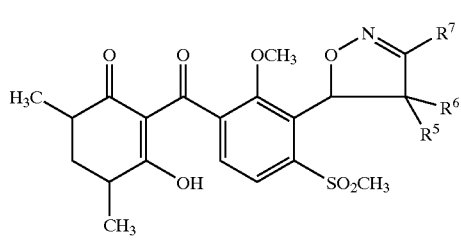

Ia28

Equally particularly preferred are the compounds Ia29., especially the compounds Ia29.1–Ia29.64, which differ from the compounds Ia1.1–Ia1.64 by the fact that $R^1$ is methoxy, $R^{13}$ is methylthio and $R^{14}$ is methyl.

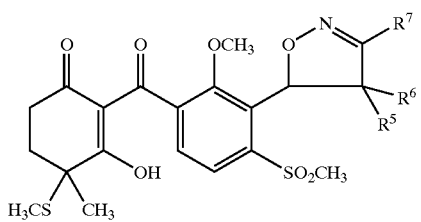

Ia29

Equally particularly preferred are the compounds Ia30., especially the compounds Ia30.1–Ia30.64, which differ from the compounds Ia1.1–Ia1.64 by the fact that $R^1$ is methoxy, $R^{14}$ and $R^{18}$ together are ethane-1,2-diyl.

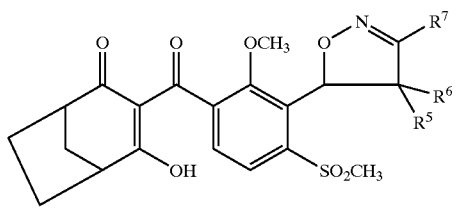

Ia30

Equally particularly preferred are the compounds Ia31., especially the compounds Ia31.1–Ia31.64, which differ from the compounds Ia1.1–Ia1.64 by the fact that $R^1$ is methoxy: $R^{13}$, $R^{14}$, $R^{17}$ and $R^{18}$ are methyl and $R^{15}$ and $R^{16}$ together are oxygen.

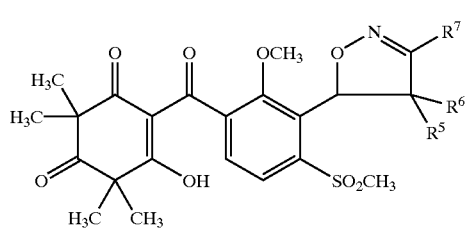

Ia31

Equally particularly preferred are the compounds Ia32., especially the compounds Ia32.1–Ia32.64, which differ from the compounds Ia1.1–Ia1.64 by the fact that $R^1$ is methoxy and $R^{15}$ is hydroxyl.

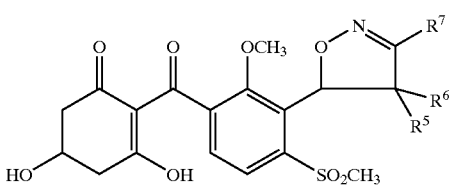

Ia32

Equally particularly preferred are the compounds Ia33., especially the compounds Ia33.1–Ia33.64, which differ from the compounds Ia1.1–Ia1.64 by the fact that $R^2$ is ethylsulfonyl.

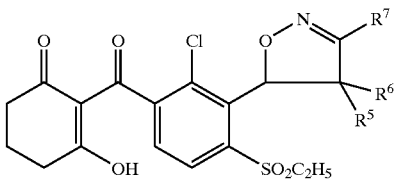

Ia33

Equally particularly preferred are the compounds Ia34., especially the compounds Ia34.1–Ia34.64, which differ from the compounds Ia1.1–Ia1.64 by the fact that $R^2$ is ethylsulfonyl and $R^{15}$ is methyl.

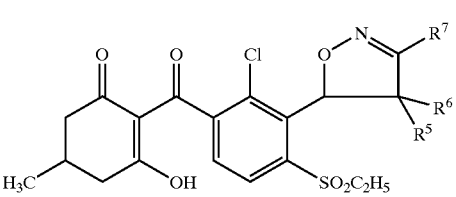

Ia34

Equally particularly preferred are the compounds Ia35., especially the compounds Ia35.1–Ia35.64, which differ from the compounds Ia1.1–Ia1.64 by the fact that $R^2$ is ethylsulfonyl and $R^{15}$ and $R^{16}$ are methyl.

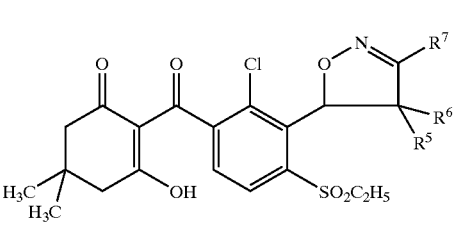

Ia35

Equally particularly preferred are the compounds Ia36., especially the compounds Ia36.1–Ia36.64, which differ from the compounds Ia1.1–Ia1.64 by the fact that $R^2$ is ethylsulfonyl and $R^{13}$ and $R^{17}$ are methyl.

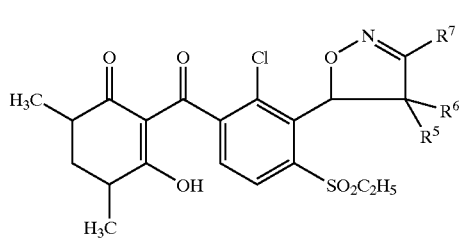

Ia36

Equally particularly preferred are the compounds Ia37., especially the compounds Ia37.1–Ia37.64, which differ from the compounds Ia1.1–Ia1.64 by the fact that $R^2$ is ethylsulfonyl, $R^{13}$ is methylthio and $R^{14}$ is methyl.

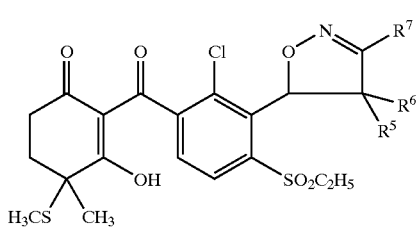

Ia37

Equally particularly preferred are the compounds Ia38., especially the compounds Ia38.1–Ia38.64, which differ from the compounds Ia1.1–Ia1.64 by the fact that $R^2$ is ethylsulfonyl, $R^{14}$ and $R^{18}$ together are ethane-1,2-diyl.

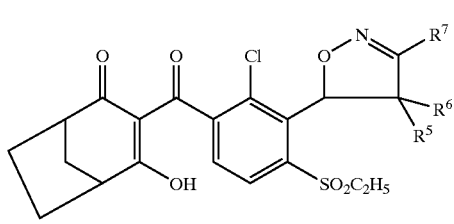

Ia38

Equally particularly preferred are the compounds Ia39., especially the compounds Ia39.1–Ia39.64, which differ from the compounds Ia1.1–Ia1.64 by the fact that $R^2$ is ethylsulfonyl, $R^{13}$, $R^{14}$, $R^{17}$ and $R^{18}$ are methyl and $R^{15}$ and $R^{16}$ together are oxygen.

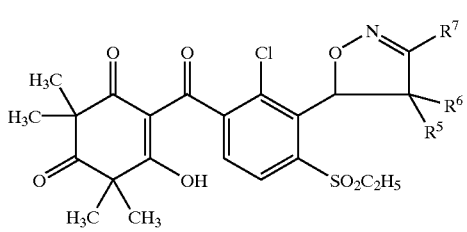

Ia39

Equally particularly preferred are the compounds Ia40., especially the compounds Ia40.1–Ia40.64, which differ from the compounds Ia1.1–Ia1.64 by the fact that $R^2$ is ethylsulfonyl and $R^{15}$ is hydroxyl.

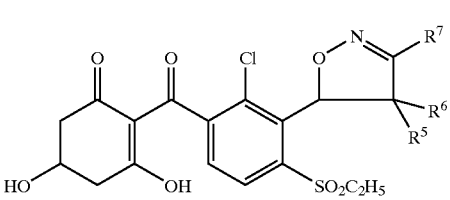

Ia40

Equally particularly preferred are the compounds Ia41., especially the compounds Ia41.1–Ia41.64, which differ from the compounds Ia1.1–Ia1.64 by the fact that $R^1$ is methyl and $R^2$ is ethylsulfonyl.

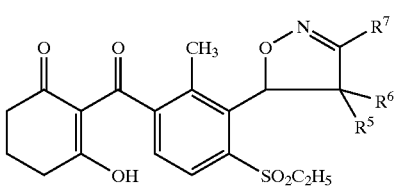

Ia41

Equally particularly preferred are the compounds Ia42., especially the compounds Ia42.1–Ia42.64, which differ from the compounds Ia1.1–Ia1.64 by the fact that $R^1$ and $R^{15}$ are methyl and $R^2$ is ethylsulfonyl.

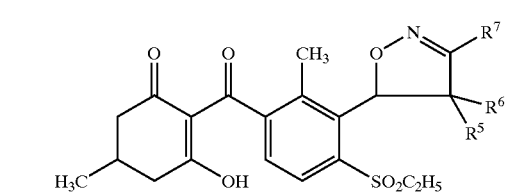

Ia42

Equally particularly preferred are the compounds Ia43., especially the compounds Ia43.1–Ia43.64, which differ from the compounds Ia1.1–Ia1.64 by the fact that $R^1$, $R^{15}$ and $R^{16}$ are methyl and $R^2$ is ethylsulfonyl.

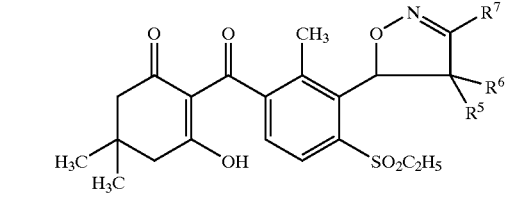

Ia43

Equally particularly preferred are the compounds Ia44., especially the compounds Ia44.1–Ia44.64, which differ from the compounds Ia1.1–Ia1.64 by the fact that $R^1$, $R^{13}$ and $R^{17}$ are methyl and $R^2$ is ethylsulfonyl.

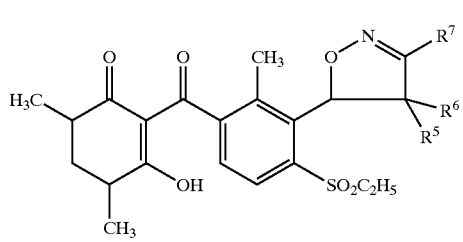

Ia44

Equally particularly preferred are the compounds Ia45., especially the compounds Ia45.1–Ia45.64, which differ from the compounds Ia1.1–Ia1.64 by the fact that $R^1$ and $R^{14}$ are methyl and $R^{13}$ is methylthio.

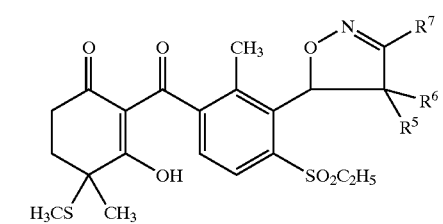

Ia45

Equally particularly preferred are the compounds Ia46., especially the compounds Ia46.1–Ia46.64, which differ from the compounds Ia1.1–Ia1.64 by the fact that $R^1$ is methyl, $R^2$ is ethylsulfonyl and $R^{14}$ and $R^{18}$ together are ethane-1,2-diyl.

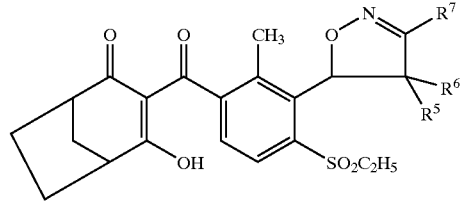

Ia46

Equally particularly preferred are the compounds Ia47., especially the compounds Ia47.1–Ia47.64, which differ from the compounds Ia1.1–Ia1.64 by the fact that $R^1$, $R^{13}$, $R^{14}$, $R^{17}$ and $R^{18}$ are methyl, $R^2$ is ethylsulfonyl and $R^{15}$ and $R^{16}$ together are oxygen.

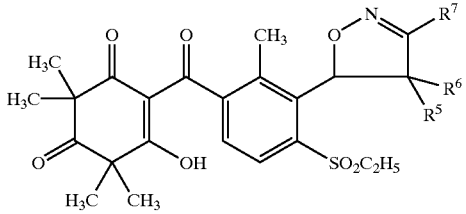

Ia47

Equally particularly preferred are the compounds Ia48., especially the compounds Ia48.1–Ia48.64, which differ from the compounds Ia1.1–Ia1.64 by the fact that $R^1$ is methyl, $R^2$ is ethylsulfonyl and $R^{15}$ is hydroxyl.

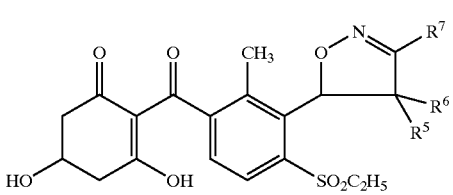

Ia48

Equally particularly preferred are the compounds Ia49., especially the compounds Ia49.1–Ia49.64, which differ from the compounds Ia1.1–Ia1.64 by the fact that $R^1$ is trifluoromethyl and $R^2$ is ethylsulfonyl.

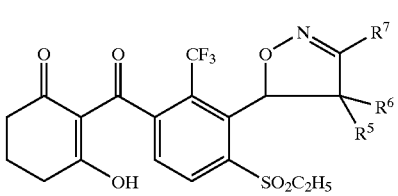

Ia49

Equally particularly preferred are the compounds Ia50., especially the compounds Ia50.1–Ia50.64, which differ from the compounds Ia1.1–Ia1.64 by the fact that $R^1$ is trifluoromethyl, $R^2$ is ethylsulfonyl and $R^{15}$ is methyl.

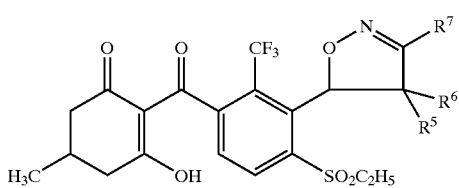

Ia50

Equally particularly preferred are the compounds Ia51., especially the compounds Ia51.1–Ia51.64, which differ from the compounds Ia1.1–Ia1.64 by the fact that $R^1$ is trifluoromethyl, $R^2$ is ethylsulfonyl and $R^{15}$ and $R^{16}$ are methyl.

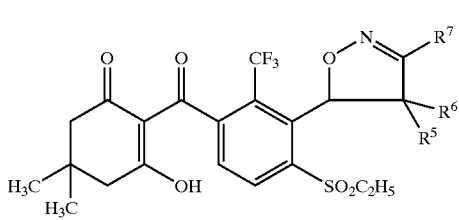

Ia51

Equally particularly preferred are the compounds Ia52., especially the compounds Ia52.1–Ia52.64, which differ from the compounds Ia1.1–Ia1.64 by the fact that $R^1$ is trifluoromethyl, $R^2$ is ethylsulfonyl and $R^{13}$ and $R^{17}$ are methyl.

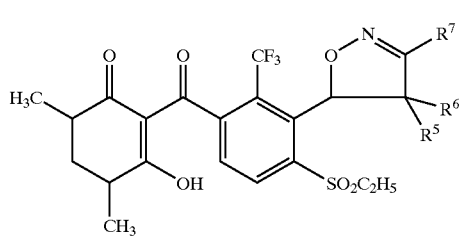

Ia52

Equally particularly preferred are the compounds Ia53., especially the compounds Ia53.1–Ia53.64, which differ from the compounds Ia1.1–Ia1.64 by the fact that $R^1$ is trifluoromethyl, $R^2$ is ethylsulfonyl, $R^{13}$ is methylthio and $R^{14}$ is methyl.

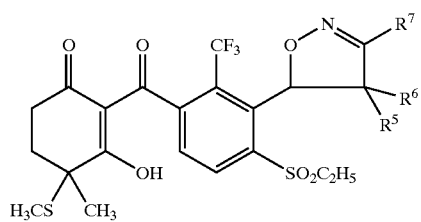

Ia53

Equally particularly preferred are the compounds Ia54., especially the compounds Ia54.1–Ia54.64, which differ from the compounds Ia1.1–Ia1.64 by the fact that $R^1$ is trifluoromethyl, $R^2$ is ethylsulfonyl and $R^{14}$ and $R^{18}$ together are ethane-1,2-diyl.

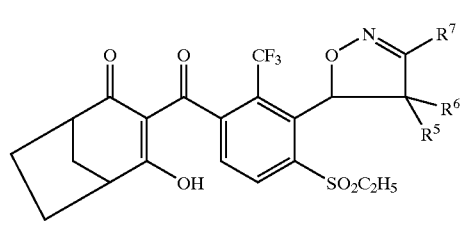

Ia54

Equally particularly preferred are the compounds Ia55., especially the compounds Ia55.1–Ia55.64, which differ from the compounds Ia1.1–Ia1.64 by the fact that $R^1$ is trifluoromethyl, $R^2$ is ethylsulfonyl, $R^{13}$, $R^{14}$, $R^{17}$ and $R^{18}$ are methyl and $R^{15}$ and $R^{16}$ together are oxygen.

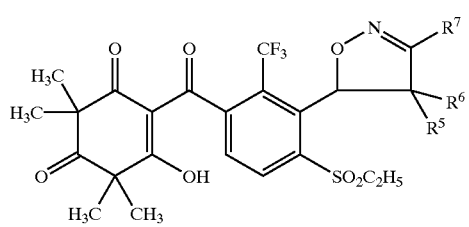

Ia55

Equally particularly preferred are the compounds Ia56., especially the compounds Ia56.1–Ia56.64, which differ from the compounds Ia1.1–Ia1.64 by the fact that $R^1$ is trifluoromethyl, $R^2$ is ethylsulfonyl and $R^{15}$ is hydroxyl.

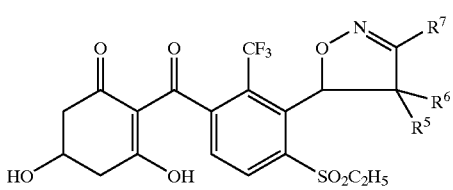

Ia56

Equally particularly preferred are the compounds Ia57., especially the compounds Ia57.1–Ia57.64, which differ from the compounds Ia1.1–Ia1.64 by the fact that $R^1$ is methoxy and $R^2$ is ethylsulfonyl.

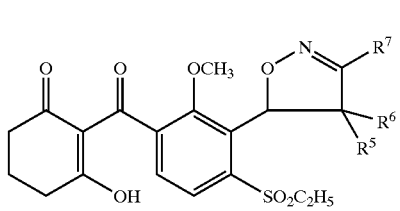

Ia57

Equally particularly preferred are the compounds Ia58., especially the compounds Ia58.1–Ia58.64, which differ from the compounds Ia1.1–Ia1.64 by the fact that $R^1$ is methoxy, $R^2$ is ethylsulfonyl and $R^{15}$ is methyl.

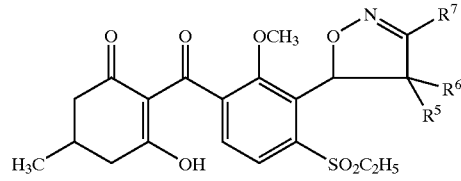

Ia58

Equally particularly preferred are the compounds Ia59., especially the compounds Ia59.1–Ia59.64, which differ from the compounds Ia1.1–Ia1.64 by the fact that $R^1$ is methoxy, $R^2$ is ethylsulfonyl and $R^{15}$ and $R^{16}$ are methyl.

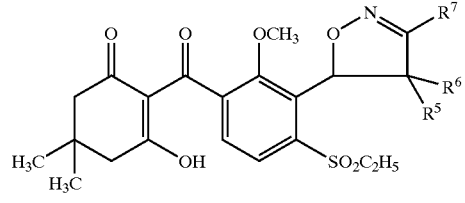

Ia59

Equally particularly preferred are the compounds Ia60., especially the compounds Ia60.1–Ia60.64, which differ from the compounds Ia1.1–Ia1.64 by the fact that $R^1$ is methoxy, $R^2$ is ethylsulfonyl and $R^{13}$ and $R^{17}$ are methyl.

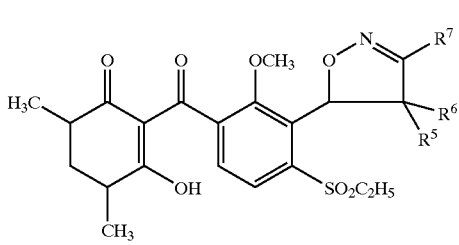

Ia60

Equally particularly preferred are the compounds Ia61., especially the compounds Ia61.1–Ia61.64, which differ from the compounds Ia1.1–Ia1.64 by the fact that $R^1$ is methoxy, $R^2$ is ethylsulfonyl, $R^{13}$ is methylthio and $R^{14}$ is methyl.

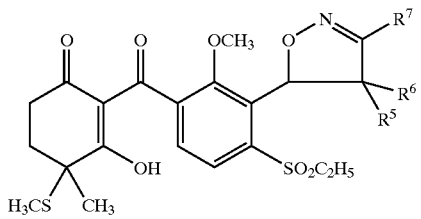

Ia61

Equally particularly preferred are the compounds Ia62., especially the compounds Ia62.1–Ia62.64, which differ from the compounds Ia1.1–Ia1.64 by the fact that $R^1$ is methoxy, $R^2$ is ethylsulfonyl and $R^{14}$ and $R^{18}$ together are ethane-1,2-diyl.

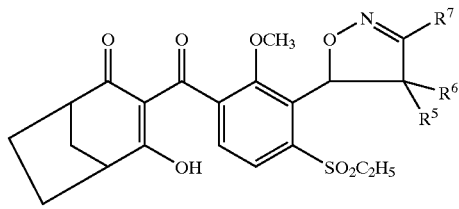

Ia62

Equally particularly preferred are the compounds Ia63., especially the compounds Ia63.1–Ia63.64, which differ from the compounds Ia1.1–Ia1.64 by the fact that $R^1$ is methoxy, $R^2$ is ethylsulfonyl, $R^{13}$, $R^{14}$, $R^{17}$ and $R^{18}$ are methyl and $R^{15}$ and $R^{16}$ together are oxygen.

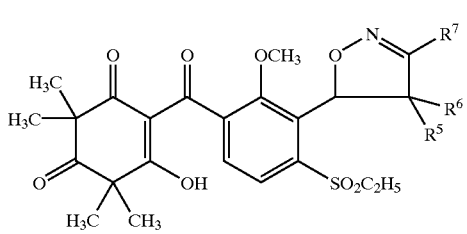

Ia63

Equally particularly preferred are the compounds Ia64., especially the compounds Ia64.1–Ia64.64, which differ from the compounds Ia1.1–Ia1.64 by the fact that $R^1$ is methoxy, $R^2$ is ethylsulfonyl and $R^{15}$ is hydroxyl.

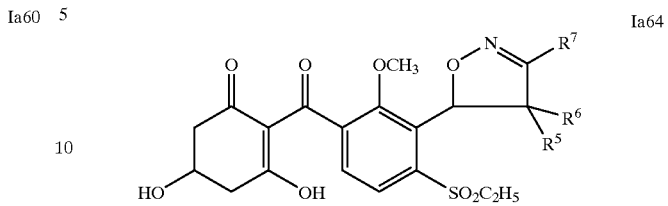

Ia64

Equally particularly preferred are the compounds Ia65., especially the compounds Ia65.1–Ia65.64, which differ from the compounds Ia1.1–Ia1.64 by the fact that $R^2$ is chlorine.

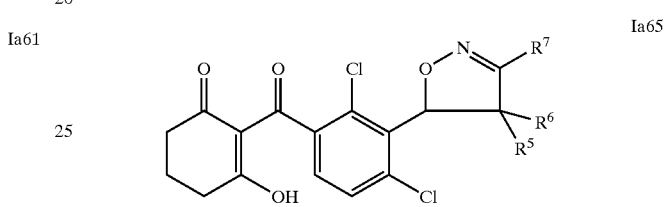

Ia65

Equally particularly preferred are the compounds Ia66., especially the compounds Ia66.1–Ia66.64, which differ from the compounds Ia1.1–Ia1.64 by the fact that $R^2$ is chlorine and $R^{15}$ is methyl.

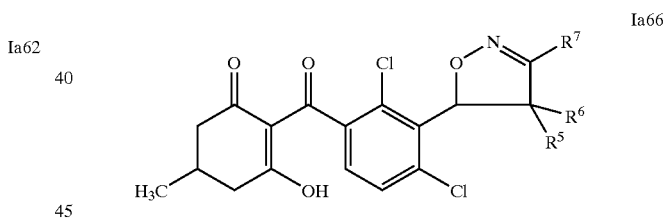

Ia66

Equally particularly preferred are the compounds Ia67., especially the compounds Ia67.1–Ia67.64, which differ from the compounds Ia1.1–Ia1.64 by the fact that $R^2$ is chlorine and $R^{15}$ and $R^{16}$ are methyl.

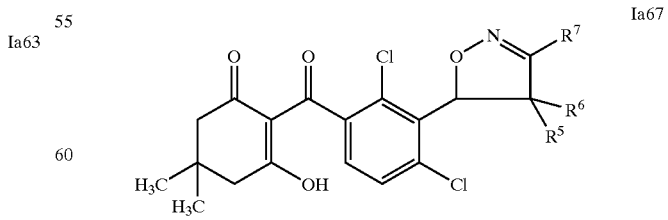

Ia67

Equally particularly preferred are the compounds Ia68., especially the compounds Ia68.1–Ia68.64, which differ from the compounds Ia1.1–Ia1.64 by the fact that $R^2$ is chlorine and $R^{13}$ and $R^{17}$ are methyl.

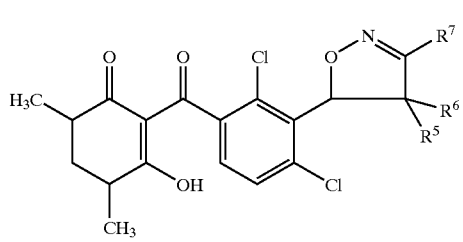

Ia68

Equally particularly preferred are the compounds Ia69., especially the compounds Ia69.1–Ia69.64, which differ from the compounds Ia1.1–Ia1.64 by the fact that $R^2$ is chlorine, $R^{13}$ is methylthio and $R^{14}$ is methyl.

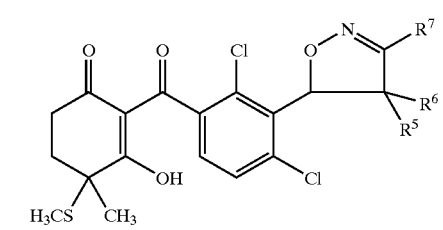

Ia69

Equally particularly preferred are the compounds Ia70., especially the compounds Ia70.1–Ia70.64, which differ from the compounds Ia1.1–Ia1.64 by the fact that $R^2$ is chlorine and $R^{14}$ and $R^{18}$ together are ethane-1,2-diyl.

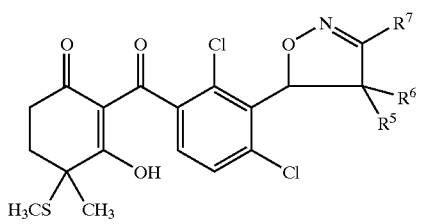

Ia70

Equally particularly preferred are the compounds Ia71., especially the compounds Ia71.1–Ia71.64, which differ from the compounds Ia1.1–Ia1.64 by the fact that $R^2$ is chlorine, $R^{13}$, $R^{14}$, $R^{17}$ and $R^{18}$ are methyl and $R^{15}$ and $R^{16}$ together are oxygen.

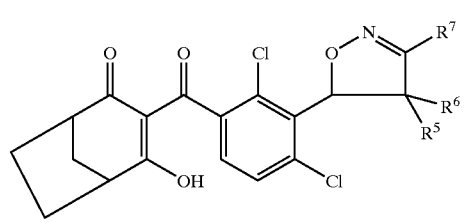

Ia71

Equally particularly preferred are the compounds Ia72., especially the compounds Ia72.1–Ia72.64, which differ from the compounds Ia1.1–Ia1.64 by the fact that $R^2$ is chlorine and $R^{15}$ is hydroxyl.

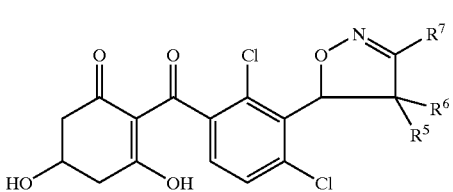

Ia72

Equally particularly preferred are the compounds Ia73., especially the compounds Ia73.1–Ia73.64, which differ from the compounds Ia1.1–Ia1.64 by the fact that $R^1$ is methyl and $R^2$ is chlorine.

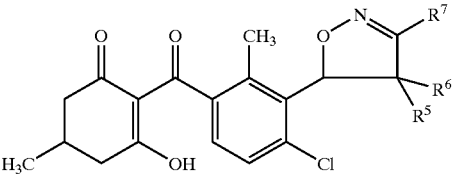

Ia73

Equally particularly preferred are the compounds Ia74., especially the compounds Ia74.1–Ia74.64, which differ from the compounds Ia1.1–Ia1.64 by the fact that $R^1$ and $R^{15}$ are methyl and $R^2$ is chlorine.

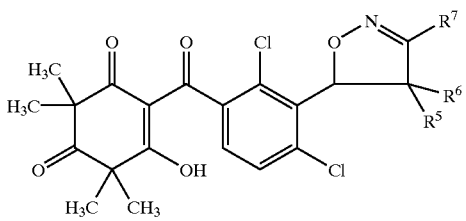

Ia74

Equally particularly preferred are the compounds Ia75., especially the compounds Ia75.1–Ia75.64, which differ from the compounds Ia1.1–Ia1.64 by the fact that $R^1$, $R^{15}$ and $R^{18}$ are methyl and $R^2$ is chlorine.

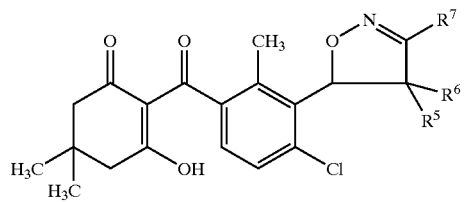

Ia75

Equally particularly preferred are the compounds Ia76., especially the compounds Ia76.1–Ia76.64, which differ from the compounds Ia1.1–Ia1.64 by the fact that $R^1$, $R^{13}$ and $R^{17}$ are methyl and $R^2$ is chlorine.

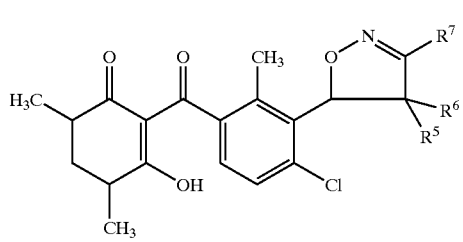
Ia76

Equally particularly preferred are the compounds Ia77., especially the compounds Ia77.1–Ia77.64, which differ from the compounds Ia1.1–Ia1.64 by the fact that $R^1$ and $R^{14}$ are methyl, $R^2$ is chlorine and $R^{13}$ is methylthio.

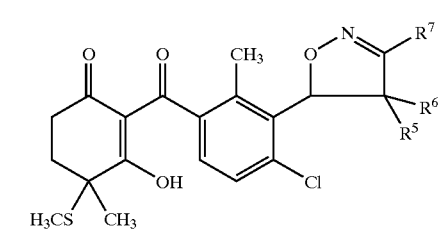
Ia77

Equally particularly preferred are the compounds Ia78., especially the compounds Ia78.1–Ia78.64, which differ from the compounds Ia1.1–Ia1.64 by the fact that $R^1$ is methyl, $R^2$ is chlorine and $R^{14}$ and $R^{18}$ together are ethane-1,2-diyl.

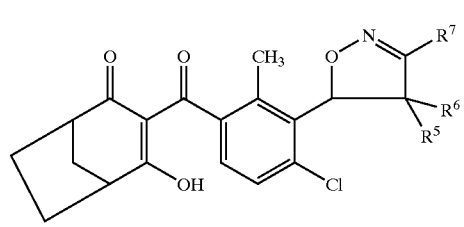
Ia78

Equally particularly preferred are the compounds Ia79., especially the compounds Ia79.1–Ia79.64, which differ from the compounds Ia1.1–Ia1.64 by the fact that $R^1$, $R^{13}$, $R^{14}$, $R^{17}$ and $R^{18}$ are methyl, $R^2$ is chlorine and $R^{15}$ and $R^{16}$ together are oxygen.

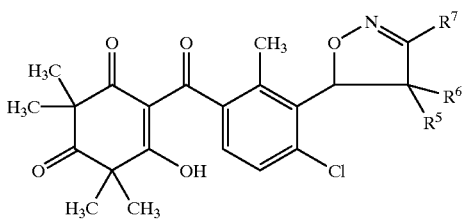
Ia79

Equally particularly preferred are the compounds Ia80., especially the compounds Ia80.1–Ia80.64, which differ from the compounds Ia1.1–Ia1.64 by the fact that $R^1$ is methyl, $R^2$ is chlorine and $R^{15}$ is hydroxyl.

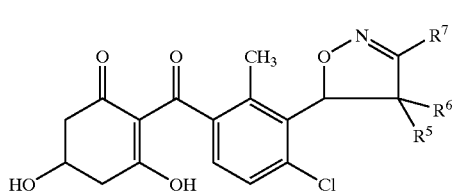
Ia80

Equally particularly preferred are the compounds Ia81., especially the compounds Ia81.1–Ia81.64, which differ from the compounds Ia1.1–Ia1.64 by the fact that $R^1$ is trifluoromethyl and $R^2$ is chlorine.

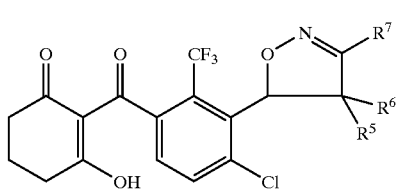
Ia81

Equally particularly preferred are the compounds Ia82., especially the compounds Ia82.1–Ia82.64, which differ from the compounds Ia1.1–Ia1.64 by the fact that $R^1$ is trifluoromethyl, $R^2$ is chlorine and $R^{15}$ is methyl.

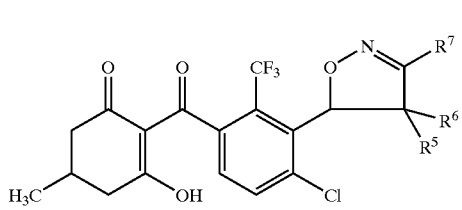
Ia82

Equally particularly preferred are the compounds Ia83., especially the compounds Ia83.1–Ia83.64, which differ from the compounds Ia1.1–Ia1.64 by the fact that $R^1$ is trifluoromethyl, $R^2$ is chlorine and $R^{15}$ and $R^{16}$ are methyl.

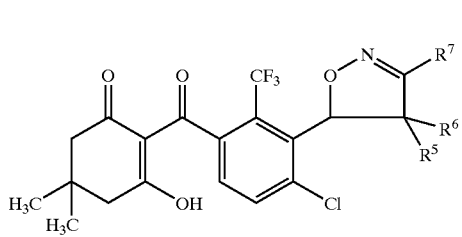
Ia83

Equally particularly preferred are the compounds Ia84., especially the compounds Ia84.1–Ia84.64, which differ from the compounds Ia1.1–Ia1.64 by the fact that $R^1$ is trifluoromethyl, $R^2$ is chlorine and $R^{13}$ and $R^{17}$ are methyl.

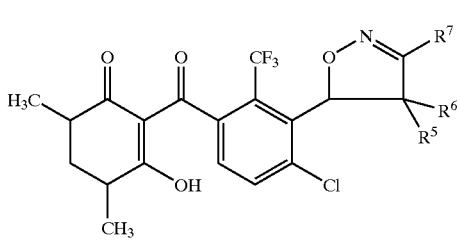

Ia84

Equally particularly preferred are the compounds Ia85., especially the compounds Ia85.1–Ia85.64, which differ from the compounds Ia1.1–Ia1.64 by the fact that $R^1$ is trifluoromethyl, $R^2$ is chlorine, $R^{13}$ is methylthio and $R^{14}$ is methyl.

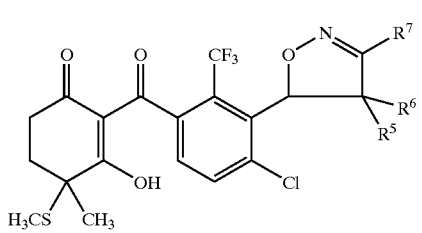

Ia85

Equally particularly preferred are the compounds Ia86., especially the compounds Ia86.1–Ia86.64, which differ from the compounds Ia1.1–Ia1.64 by the fact that $R^1$ is trifluoromethyl, $R^2$ is chlorine and $R^{14}$ and $R^{18}$ together are ethane-1,2-diyl.

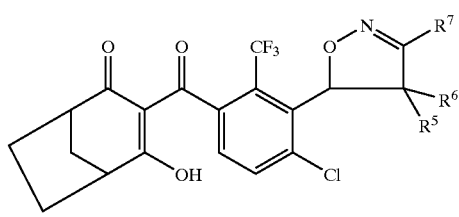

Ia86

Equally particularly preferred are the compounds Ia87., especially the compounds Ia87.1–Ia87.64, which differ from the compounds Ia1.1–Ia1.64 by the fact that $R^1$ is trifluoromethyl, $R^2$ is chlorine, $R^{13}$, $R^{14}$, $R^{17}$ and $R^{18}$ are methyl and $R^{15}$ and $R^{16}$ together are oxygen.

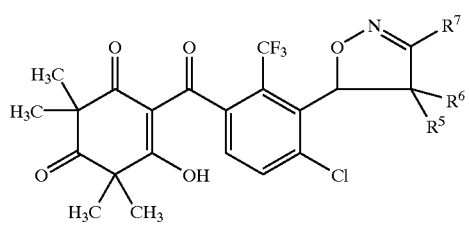

Ia87

Equally particularly preferred are the compounds Ia88., especially the compounds Ia88.1–Ia88.64, which differ from the compounds Ia1.1–Ia1.64 by the fact that $R^1$ is trifluoromethyl, $R^2$ is chlorine and $R^{15}$ is hydroxyl.

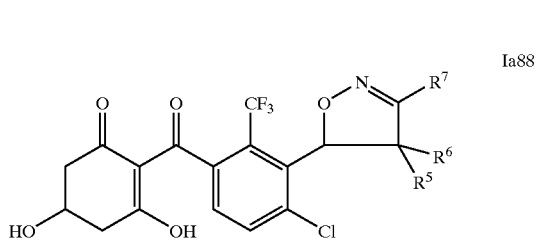

Ia88

Equally particularly preferred are the compounds Ia89., especially the compounds Ia89.1–Ia89.64, which differ from the compounds Ia1.1–Ia1.64 by the fact that $R^1$ is methoxy and $R^2$ is chlorine.

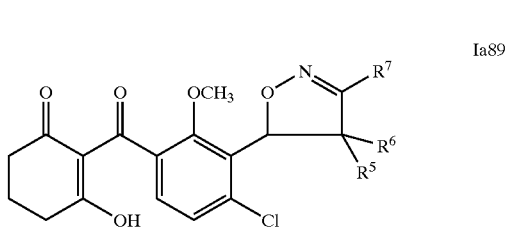

Ia89

Equally particularly preferred are the compounds Ia90., especially the compounds Ia90.1–Ia90.64, which differ from the compounds Ia1.1–Ia1.64 by the fact that $R^1$ is methoxy, $R^2$ is chlorine and $R^{15}$ is methyl.

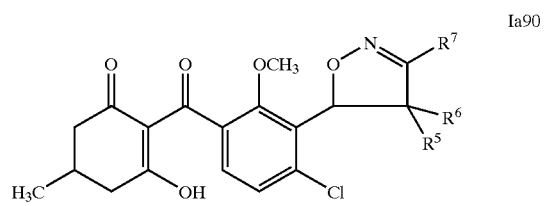

Ia90

Equally particularly preferred are the compounds Ia91., especially the compounds Ia91.1–Ia91.64, which differ from the compounds Ia1.1–Ia1.64 by the fact that $R^1$ is methoxy, $R^2$ is chlorine and $R^{15}$ and $R^{16}$ are methyl.

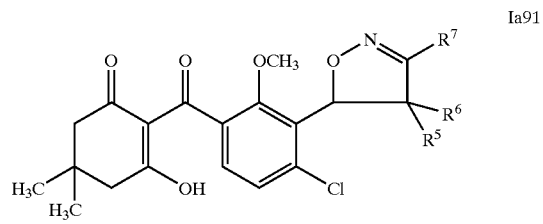

Ia91

Equally particularly preferred are the compounds Ia92., especially the compounds Ia92.1–Ia92.64, which differ from the compounds Ia1.1–Ia1.64 by the fact that $R^1$ is methoxy, $R^2$ is chlorine and $R^{13}$ and $R^{17}$ are methyl.

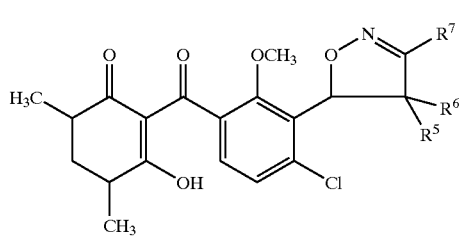

Ia92

Equally particularly preferred are the compounds Ia93., especially the compounds Ia93.1–Ia93.64, which differ from the compounds Ia1.1–Ia1.64 by the fact that $R^1$ is methoxy, $R^2$ is chlorine, $R^{13}$ is methylthio and $R^{14}$ is methyl.

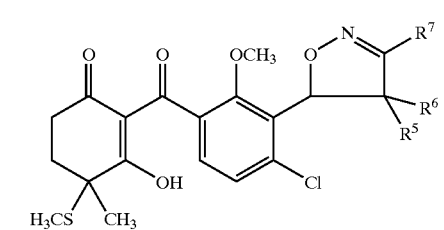

Ia93

Equally particularly preferred are the compounds Ia94., especially the compounds Ia94.1–Ia94.64, which differ from the compounds Ia1.1–Ia1.64 by the fact that $R^1$ is methoxy, $R^2$ is chlorine and $R^{14}$ and $R^{18}$ together are ethane-1,2-diyl.

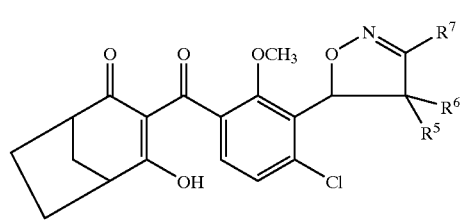

Ia94

Equally particularly preferred are the compounds Ia95., especially the compounds Ia95.1–Ia95.64, which differ from the compounds Ia1.1–Ia1.64 by the fact that $R^1$ is methoxy, $R^2$ is chlorine, $R^{13}$, $R^{14}$, $R^{12}$ and $R^{18}$ are methyl and $R^{15}$ and $R^{16}$ together are oxygen.

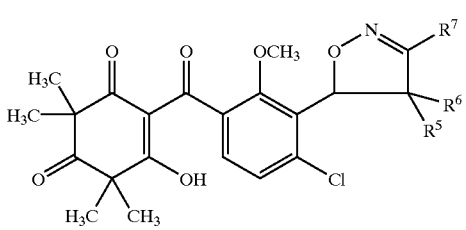

Ia95

Equally particularly preferred are the compounds Ia96., especially the compounds Ia96.1–Ia96.64, which differ from the compounds Ia1.1–Ia1.64 by the fact that $R^1$ is methoxy, $R^2$ is chlorine and $R^{15}$ is hydroxyl.

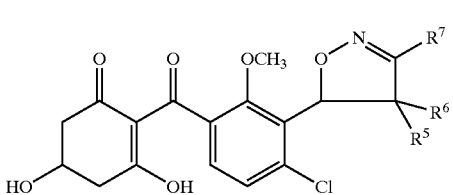

Ia96

Equally particularly preferred are the compounds Ia97., especially the compounds Ia97.1–Ia97.64, which differ from the compounds Ia1.1–Ia1.64 by the fact that $R^2$ is trifluoromethyl.

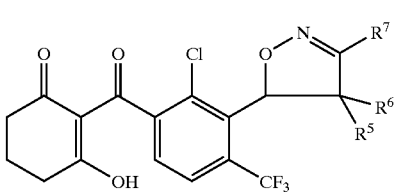

Ia97

Equally particularly preferred are the compounds Ia98., especially the compounds Ia98.1–Ia98.64, which differ from the compounds Ia1.1–Ia1.64 by the fact that $R^2$ is trifluoromethyl and $R^{15}$ is methyl.

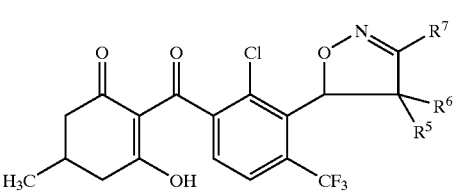

Ia98

Equally particularly preferred are the compounds Ia99., especially the compounds Ia99.1–Ia99.64, which differ from the compounds Ia1.1–Ia1.64 by the fact that $R^2$ is trifluoromethyl and $R^{15}$ and $R^{16}$ are methyl.

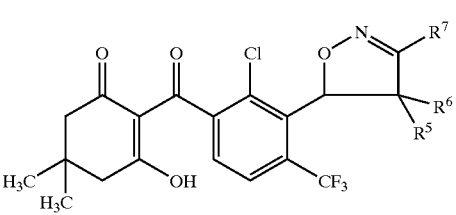

Ia99

Equally particularly preferred are the compounds Ia100., especially the compounds Ia100.1–Ia100.64, which differ from the compounds Ia1.1–Ia1.64 by the fact that $R^2$ is trifluoromethyl and $R^{13}$ and $R^{17}$ are methyl.

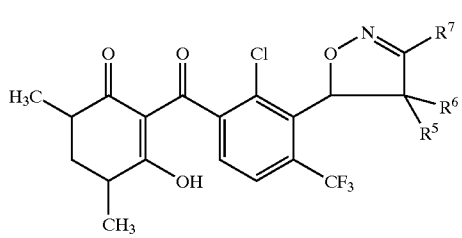
Ia100

Equally particularly preferred are the compounds Ia101., especially the compounds Ia101.1–Ia101.64, which differ from the compounds Ia1.1–Ia1.64 by the fact that $R^2$ is trifluoromethyl, $R^{13}$ is methylthio and $R^{14}$ is methyl.

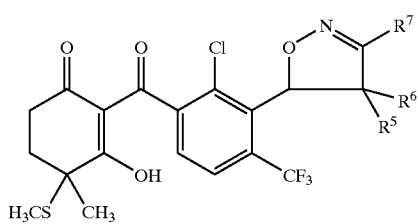
Ia101

Equally particularly preferred are the compounds Ia102., especially the compounds Ia102.1–Ia102.64, which differ from the compounds Ia1.1–Ia1.64 by the fact that $R^2$ is trifluoromethyl and $R^{14}$ and $R^{18}$ together are ethane-1,2-diyl.

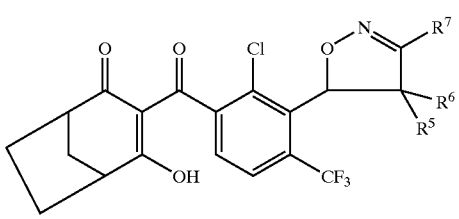
Ia102

Equally particularly preferred are the compounds Ia103., especially the compounds Ia103.1–Ia103.64, which differ from the compounds Ia1.1–Ia1.64 by the fact that $R^2$ is trifluoromethyl, $R^{13}$, $R^{14}$, $R^{17}$ and $R^{18}$ are methyl and $R^{15}$ and $R^{16}$ together are oxygen.

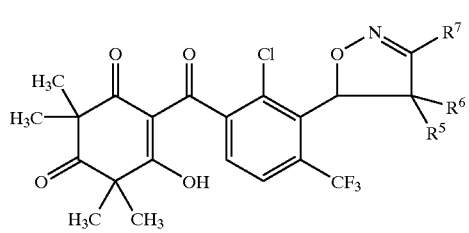
Ia103

Equally particularly preferred are the compounds Ia104., especially the compounds Ia104.1–Ia104.64, which differ from the compounds Ia1.1–Ia1.64 by the fact that $R^2$ is trifluoromethyl and $R^{15}$ is hydroxyl.

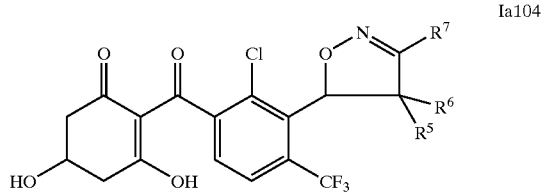
Ia104

Equally particularly preferred are the compounds Ia105., especially the compounds Ia105.1–Ia105.64, which differ from the compounds Ia1.1–Ia1.64 by the fact that $R^1$ is methyl and $R^2$ is trifluoromethyl.

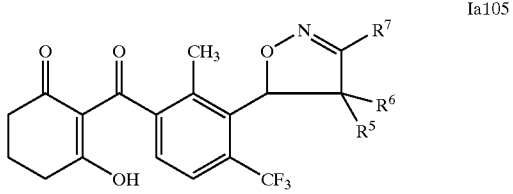
Ia105

Equally particularly preferred are the compounds Ia106., especially the compounds Ia106.1–Ia106.64, which differ from the compounds Ia1.1–Ia1.64 by the fact that $R^1$ and $R^{15}$ are methyl and $R^2$ is trifluoromethyl.

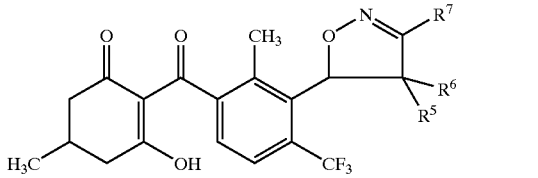
Ia106

Equally particularly preferred are the compounds Ia107., especially the compounds Ia107.1–Ia107.64, which differ from the compounds Ia1.1–Ia1.64 by the fact that $R^1$, $R^{15}$ and $R^{16}$ are methyl and $R^2$ is trifluoromethyl.

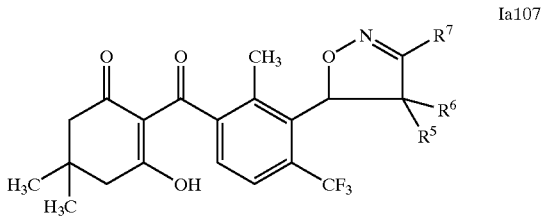
Ia107

Equally particularly preferred are the compounds Ia108., especially the compounds Ia108.1–Ia108.64, which differ from the compounds Ia1.1–Ia1.64 by the fact that $R^1$, $R^{13}$ and $R^{17}$ are methyl and $R^2$ is trifluoromethyl.

from the compounds Ia1.1–Ia1.64 by the fact that $R^1$ is methyl, $R^2$ is trifluoromethyl and $R^{15}$ is hydroxyl.

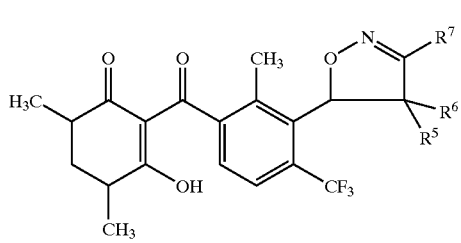

Ia108

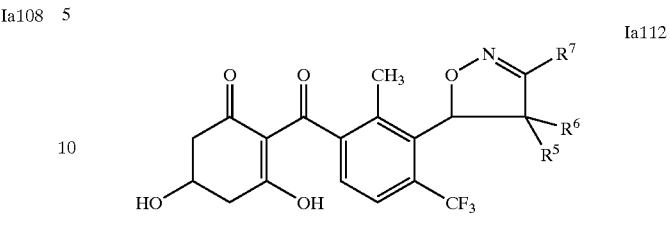

Ia112

Equally particularly preferred are the compounds Ia109., especially the compounds Ia109.1–Ia109.64, which differ from the compounds Ia1.1–Ia1.64 by the fact that $R^1$ and $R^{14}$ are methyl, $R^2$ is trifluoromethyl and $R^{13}$ is methylthio.

Equally particularly preferred are the compounds Ia113., especially the compounds Ia113.1–Ia113.64, which differ from the compounds Ia1.1–Ia1.64 by the fact that $R^1$ and $R^2$ are trifluoromethyl.

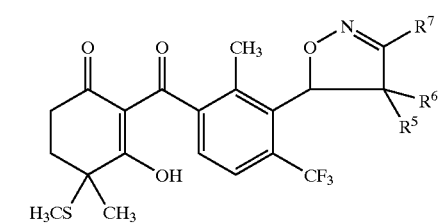

Ia109

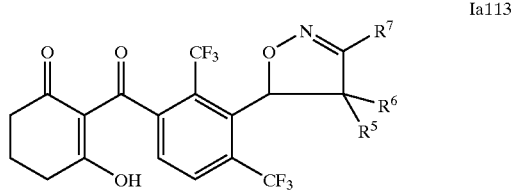

Ia113

Equally particularly preferred are the compounds Ia110., especially the compounds Ia110.1–Ia110.64, which differ from the compounds Ia1.1–Ia1.64 by the fact that $R^1$ is methyl, $R^2$ is trifluoromethyl and $R^{14}$ and $R^{18}$ together are ethane-1,2-diyl.

Equally particularly preferred are the compounds Ia114., especially the compounds Ia114.1–Ia114.64, which differ from the compounds Ia1.1–Ia1.64 by the fact that $R^1$ and $R^2$ are trifluoromethyl and $R^{15}$ is methyl.

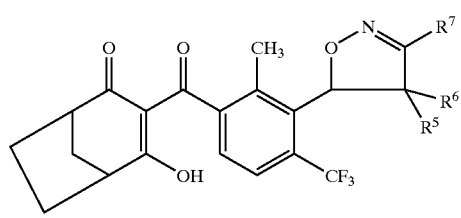

Ia110

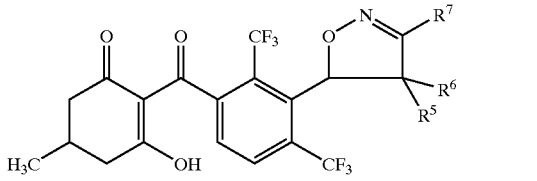

Ia114

Equally particularly preferred are the compounds Ia111., especially the compounds Ia111.1–Ia111.64, which differ from the compounds Ia1.1–Ia1.64 by the fact that $R^1$, $R^{13}$, $R^{14}$, $R^{17}$ and $R^{18}$ are methyl, $R^2$ is trifluoromethyl and $R^{15}$ and $R^{16}$ together are oxygen.

Equally particularly preferred are the compounds Ia115., especially the compounds Ia115.1–Ia115.64, which differ from the compounds Ia1.1–Ia1.64 by the fact that $R^1$ and $R^2$ are trifluoromethyl and $R^{15}$ and $R^{16}$ are methyl.

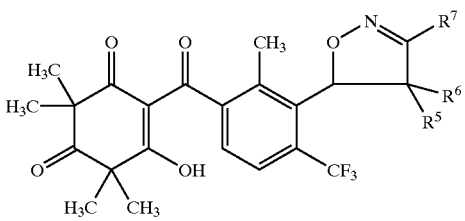

Ia111

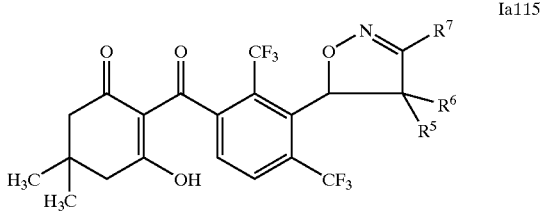

Ia115

Equally particularly preferred are the compounds Ia112., especially the compounds Ia112.1–Ia112.64, which differ Equally particularly preferred are the compounds Ia116., especially the compounds Ia116.1–Ia116.64, which differ from the compounds Ia1.1–Ia1.64 by the fact that $R^1$ and $R^2$ are trifluoromethyl and $R^{13}$ and $R^{17}$ are methyl.

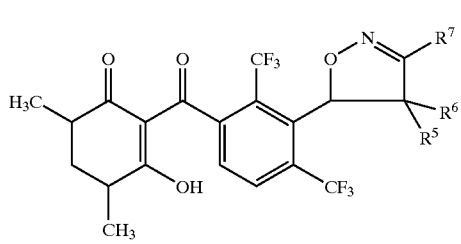
Ia116

Equally particularly preferred are the compounds Ia117., especially the compounds Ia117.1–Ia117.64, which differ from the compounds Ia1.1–Ia1.64 by the fact that $R^1$ and $R^2$ are trifluoromethyl, $R^{13}$ is methylthio and $R^{14}$ is methyl.

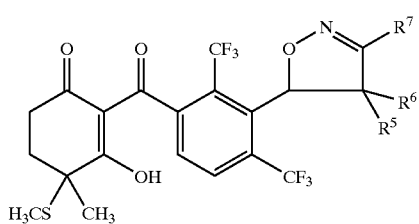
Ia117

Equally particularly preferred are the compounds Ia118., especially the compounds Ia118.1–Ia118.64, which differ from the compounds Ia1.1–Ia1.64 by the fact that $R^1$ and $R^2$ are trifluoromethyl and $R^{14}$ and $R^{18}$ together are ethane-1,2-diyl.

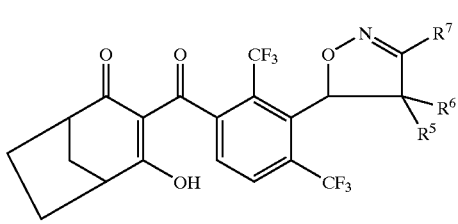
Ia118

Equally particularly preferred are the compounds Ia119., especially the compounds Ia119.1–Ia119.64, which differ from the compounds Ia1.1–Ia1.64 by the fact that $R^1$ and $R^2$ are trifluoromethyl, $R^{13}$, $R^{14}$, $R^{17}$ and $R^{18}$ are methyl and $R^{15}$ and $R^{16}$ together are oxygen.

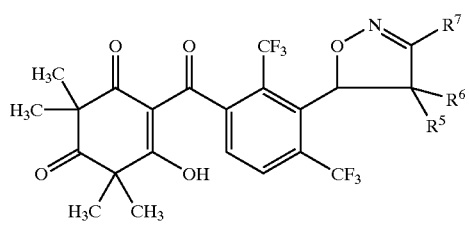
Ia119

Equally particularly preferred are the compounds Ia120., especially the compounds Ia120.1–Ia120.64, which differ from the compounds Ia1.1–Ia1.64 by the fact that $R^1$ and $R^2$ are trifluoromethyl and $R^{15}$ is hydroxyl.

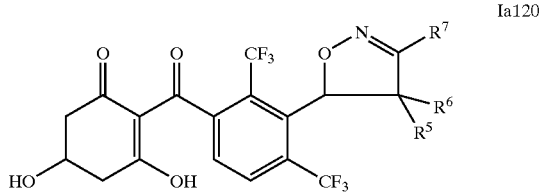
Ia120

Equally particularly preferred are the compounds Ia121., especially the compounds Ia121.1–Ia121.64, which differ from the compounds Ia1.1–Ia1.64 by the fact that $R^1$ is methoxy and $R^2$ is trifluoromethyl.

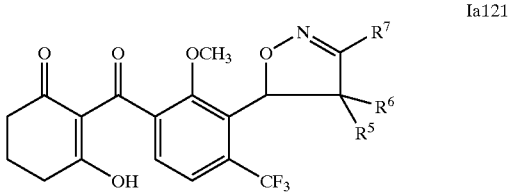
Ia121

Equally particularly preferred are the compounds Ia122., especially the compounds Ia122.1–Ia122.64, which differ from the compounds Ia1.1–Ia1.64 by the fact that $R^1$ is methoxy, $R^2$ is trifluoromethyl and $R^{15}$ is methyl.

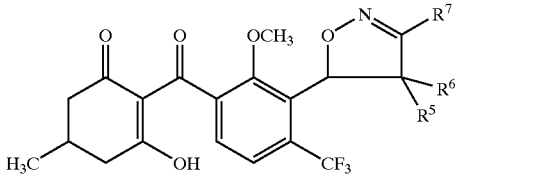
Ia122

Equally particularly preferred are the compounds Ia123., especially the compounds Ia123.1–Ia123.64, which differ from the compounds Ia1.1–Ia1.64 by the fact that $R^1$ is methoxy, $R^2$ is trifluoromethyl and $R^{15}$ and $R^{16}$ are methyl.

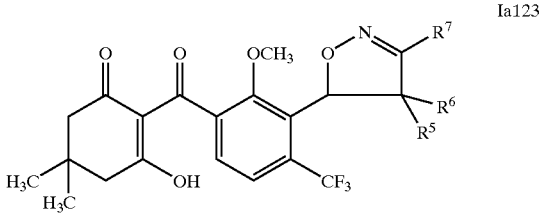
Ia123

Equally particularly preferred are the compounds Ia124., especially the compounds Ia124.1–Ia124.64, which differ from the compounds Ia1.1–Ia1.64 by the fact that $R^1$ is methoxy, $R^2$ is trifluoromethyl and $R^{13}$ and $R^{17}$ are methyl.

from the compounds Ia1.1–Ia1.64 by the fact that $R^1$ is methoxy, $R^2$ is trifluoromethyl and $R^{15}$ is hydroxyl.

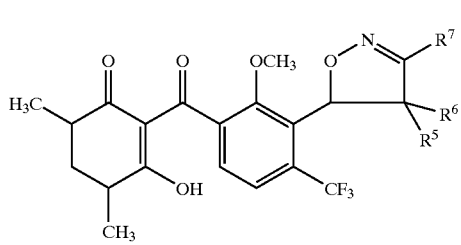

Ia124

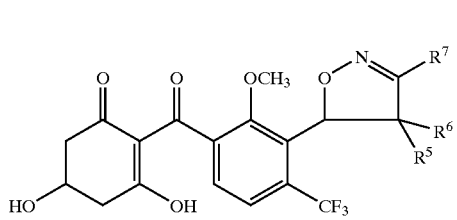

Ia128

Equally particularly preferred are the compounds Ia125., especially the compounds Ia125.1–Ia125.64, which differ from the compounds Ia1.1–Ia1.64 by the fact that $R^1$ is methoxy, $R^2$ is trifluoromethyl, $R^{13}$ is methylthio and $R^{14}$ is methyl.

Equally particularly preferred are the compounds Ia129., especially the compounds Ia129.1–Ia129.64, which differ from the compounds Ia1.1–Ia1.64 by the fact that $R^3$ is chlorine.

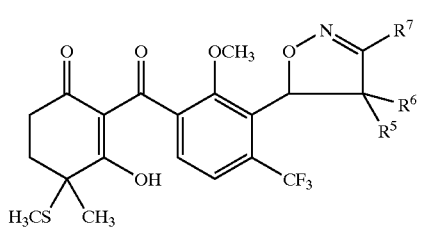

Ia125

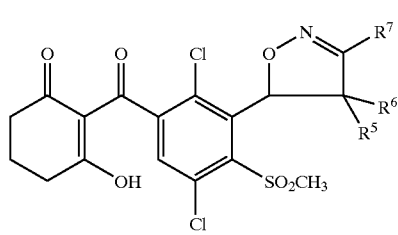

Ia129

Equally particularly preferred are the compounds Ia126., especially the compounds Ia126.1–Ia126.64, which differ from the compounds Ia1.1–Ia1.64 by the fact that $R^1$ is methoxy, $R^2$ is trifluoromethyl and $R^{14}$ and $R^{18}$ together are ethane-1,2-diyl.

Equally particularly preferred are the compounds Ia130., especially the compounds Ia130.1–Ia130.64, which differ from the compounds Ia1.1–Ia1.64 by the fact that $R^3$ is chlorine and $R^{15}$ is methyl.

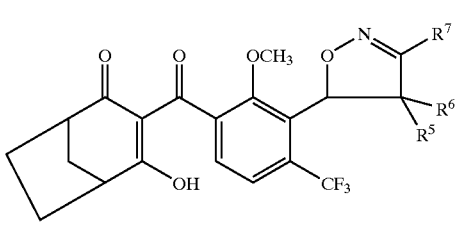

Ia126

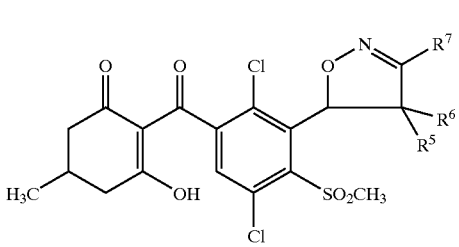

Ia130

Equally particularly preferred are the compounds Ia127., especially the compounds Ia127.1–Ia127.64, which differ from the compounds Ia1.1–Ia1.64 by the fact that $R^1$ is methoxy, $R^2$ is trifluoromethyl, $R^{13}$, $R^{14}$, $R^{17}$ and $R^{18}$ are methyl and $R^{15}$ and $R^{16}$ together are oxygen.

Equally particularly preferred are the compounds Ia131., especially the compounds Ia131.1–Ia131.64, which differ from the compounds Ia1.1–Ia1.64 by the fact that $R^3$ is chlorine and $R^{15}$ and $R^{16}$ are methyl.

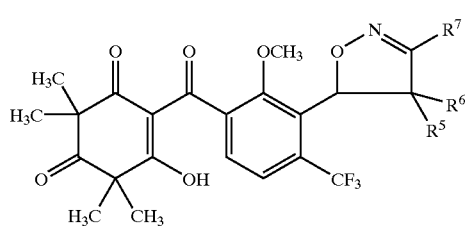

Ia127

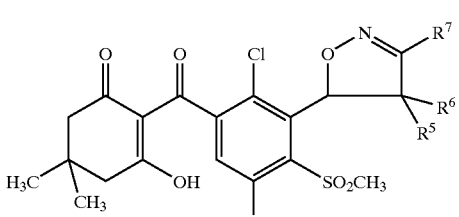

Ia131

Equally particularly preferred are the compounds Ia128., especially the compounds Ia128.1–Ia128.64, which differ Equally particularly preferred are the compounds Ia132., especially the compounds Ia132.1–Ia132.64, which differ from the compounds Ia1.1–Ia1.64 by the fact that $R^3$ is chlorine and $R^{13}$ and $R^{17}$ are methyl.

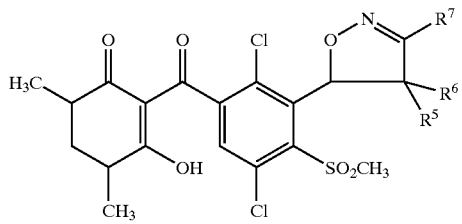

Ia132

Equally particularly preferred are the compounds Ia133., especially the compounds Ia133.1–Ia133.64, which differ from the compounds Ia1.1–Ia1.64 by the fact that $R^3$ is chlorine, $R^{13}$ is methylthio and $R^{14}$ is methyl.

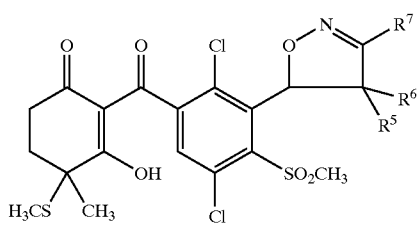

Ia133

Equally particularly preferred are the compounds Ia134., especially the compounds Ia134.1–Ia134.64, which differ from the compounds Ia1.1–Ia1.64 by the fact that $R^3$ is chlorine and $R^{14}$ and $R^{18}$ together are ethane-1,2-diyl.

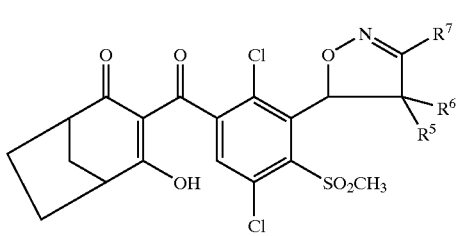

Ia134

Equally particularly preferred are the compounds Ia135., especially the compounds Ia135.1–Ia135.64, which differ from the compounds Ia1.1–Ia1.64 by the fact that $R^3$ is chlorine, $R^{13}$, $R^{14}$, $R^{17}$ and $R^{18}$ are methyl and $R^{15}$ and $R^{16}$ together are oxygen.

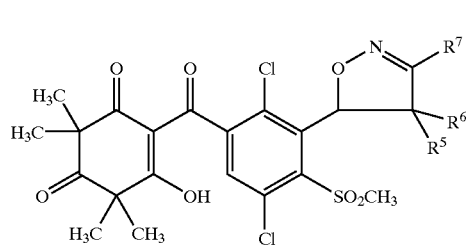

Ia135

Equally particularly preferred are the compounds Ia136., especially the compounds Ia136.1–Ia136.64, which differ from the compounds Ia1.1–Ia1.64 by the fact that $R^3$ is chlorine and $R^{15}$ is hydroxyl.

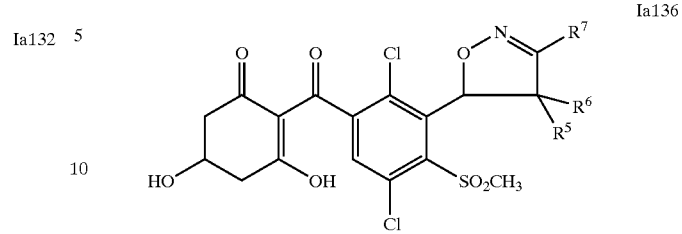

Ia136

Equally particularly preferred are the compounds Ia137., especially the compounds Ia137.1–Ia137.64, which differ from the compounds Ia1.1–Ia1.64 by the fact that $R^2$ is ethylsulfonyl and $R^3$ is chlorine.

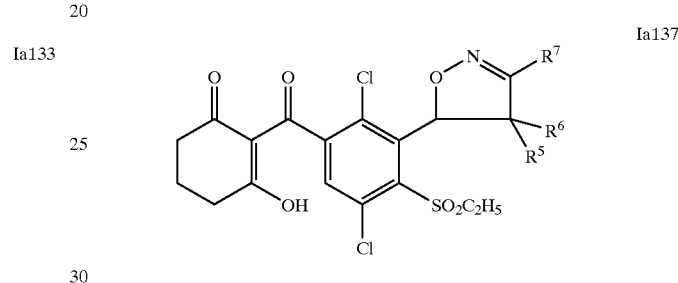

Ia137

Equally particularly preferred are the compounds Ia138., especially the compounds Ia138.1–Ia138.64, which differ from the compounds Ia1.1–Ia1.64 by the fact that $R^2$ is ethylsulfonyl, $R^3$ is chlorine and $R^{15}$ is methyl.

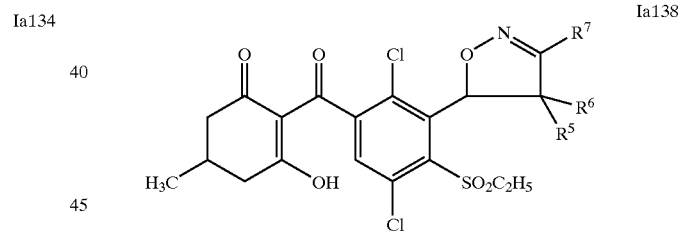

Ia138

Equally particularly preferred are the compounds Ia139., especially the compounds Ia139.1–Ia139.64, which differ from the compounds Ia1.1–Ia1.64 by the fact that $R^2$ is ethylsulfonyl, $R^3$ is chlorine and $R^{15}$ and $R^{16}$ are methyl.

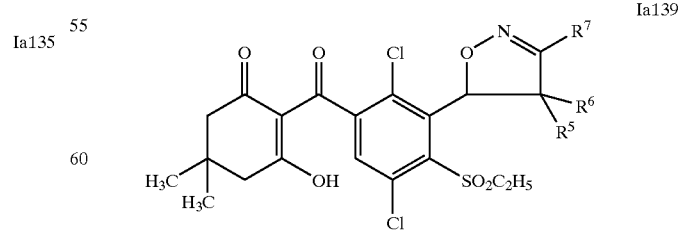

Ia139

Equally particularly preferred are the compounds Ia140., especially the compounds Ia140.1–Ia140.64, which differ from the compounds Ia1.1–Ia1.64 by the fact that $R^2$ is ethylsulfonyl, $R^3$ is chlorine and $R^{13}$ and $R^{17}$ are methyl.

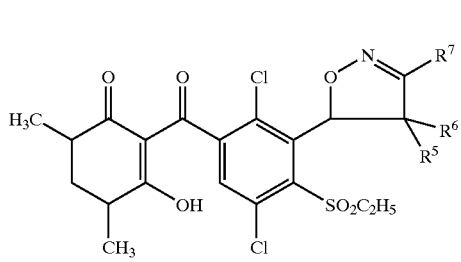

Ia140

Equally particularly preferred are the compounds Ia141., especially the compounds Ia141.1–Ia141.64, which differ from the compounds Ia1.1–Ia1.64 by the fact that $R^2$ is ethylsulfonyl, $R^3$ is chlorine, $R^{13}$ is methylthio and $R^{14}$ is methyl.

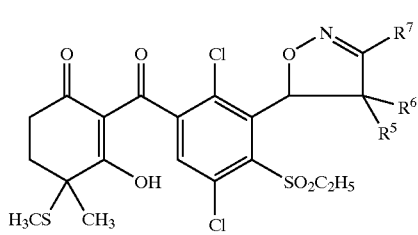

Ia141

Equally particularly preferred are the compounds Ia142., especially the compounds Ia142.1–Ia142.64, which differ from the compounds Ia1.1–Ia1.64 by the fact that $R^2$ is ethylsulfonyl, $R^3$ is chlorine and $R^{14}$ and $R^{18}$ together are ethane-1,2-diyl.

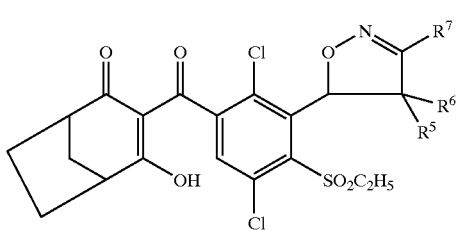

Ia142

Equally particularly preferred are the compounds Ia143., especially the compounds Ia143.1–Ia143.64, which differ from the compounds Ia1.1–Ia1.64 by the fact that $R^2$ is ethylsulfonyl, $R^3$ is chlorine, $R^{13}$, $R^{14}$, $R^{17}$ and $R^{18}$ are methyl and $R^{15}$ and $R^{16}$ together are oxygen.

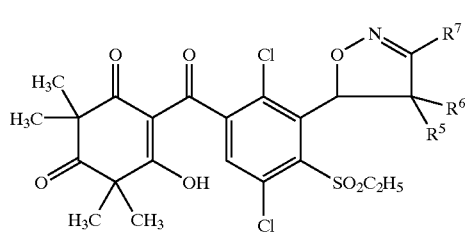

Ia143

Equally particularly preferred are the compounds Ia144., especially the compounds Ia144.1–Ia144.64, which differ from the compounds Ia1.1–Ia1.64 by the fact that $R^2$ is ethylsulfonyl, $R^3$ is chlorine and $R^{15}$ is hydroxyl.

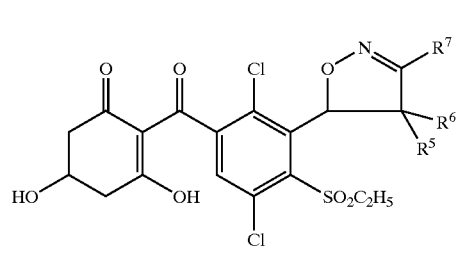

Ia144

Equally particularly preferred are the compounds Ia145., especially the compounds Ia145.1–Ia145.64, which differ from the compounds Ia1.1–Ia1.64 by the fact that $R^1$ and $R^3$ are methyl.

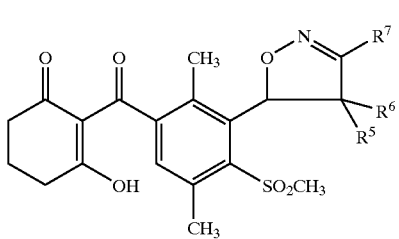

Ia145

Equally particularly preferred are the compounds Ia146., especially the compounds Ia146.1–Ia146.64, which differ from the compounds Ia1.1–Ia1.64 by the fact that $R^1$, $R^3$ and $R^{15}$ are methyl.

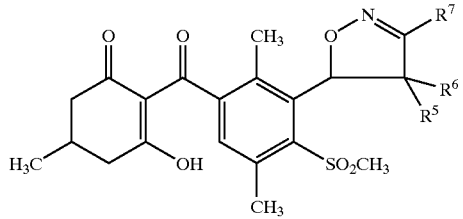

Ia146

Equally particularly preferred are the compounds Ia147., especially the compounds Ia147.1–Ia147.64, which differ from the compounds Ia1.1–Ia1.64 by the fact that $R^1$, $R^3$, $R^{15}$ and $R^{16}$ are methyl.

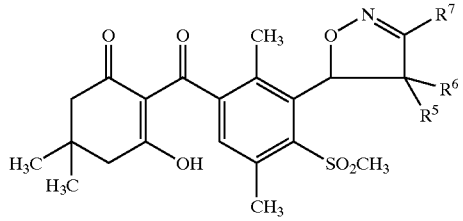

Ia147

Equally particularly preferred are the compounds Ia148., especially the compounds Ia148.1–Ia148.64, which differ from the compounds Ia1.1–Ia1.64 by the fact that $R^1$, $R^3$, $R^{13}$ and $R^{17}$ are methyl.

from the compounds Ia1.1–Ia1.64 by the fact that $R^1$ and $R^3$ are methyl and $R^{15}$ is hydroxyl.

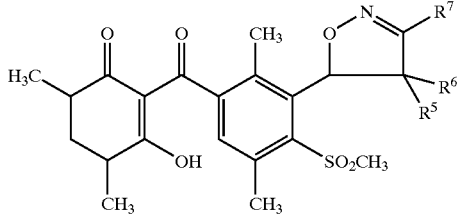

Ia148

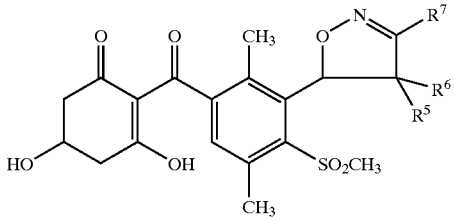

Ia152

Equally particularly preferred are the compounds Ia149., especially the compounds Ia149.1–Ia149.64, which differ from the compounds Ia1.1–Ia1.64 by the fact that $R^1$, $R^3$ and $R^{14}$ are methyl and $R^{13}$ is methylthio.

Equally particularly preferred are the compounds Ia153., especially the compounds Ia153.1–Ia153.64, which differ from the compounds Ia1.1–Ia1.64 by the fact that $R^1$ and $R^3$ are methyl and $R^2$ is ethylsulfonyl.

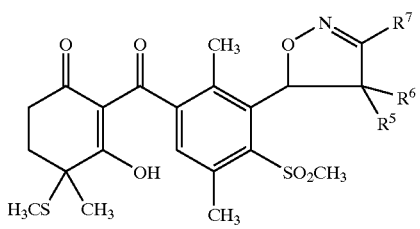

Ia149

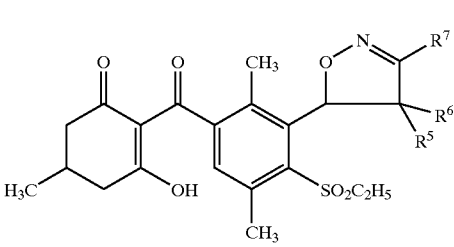

Ia153

Equally particularly preferred are the compounds Ia150., especially the compounds Ia150.1–Ia150.64, which differ from the compounds Ia1.1–Ia1.64 by the fact that $R^1$ and $R^3$ are methyl and $R^{14}$ and $R^{18}$ together are ethane-1,2-diyl.

Equally particularly preferred are the compounds Ia154., especially the compounds Ia154.1–Ia154.64, which differ from the compounds Ia1.1–Ia1.64 by the fact that $R^1$, $R^3$ and $R^{15}$ are methyl and $R^2$ is ethylsulfonyl.

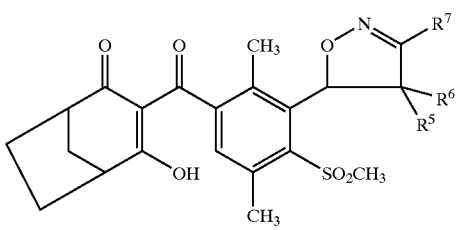

Ia150

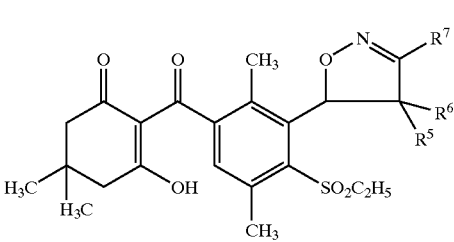

Ia154

Equally particularly preferred are the compounds Ia151., especially the compounds Ia151.1–Ia11.64, which differ from the compounds Ia1.1–Ia1.64 by the fact that $R^1$, $R^3$, $R^{13}$, $R^{14}$, $R^{17}$ and $R^{18}$ are methyl and $R^{15}$ and $R^{16}$ together are oxygen.

Equally particularly preferred are the compounds Ia155., especially the compounds Ia155.1–Ia155.64, which differ from the compounds Ia1.1–Ia1.64 by the fact that $R^1$, $R^3$, $R^{15}$ and $R^{16}$ are methyl and $R^2$ is ethylsulfonyl.

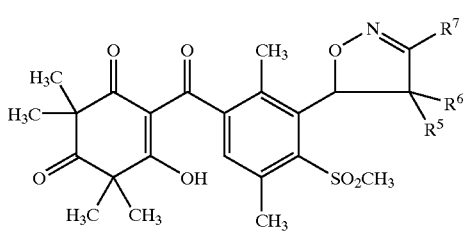

Ia151

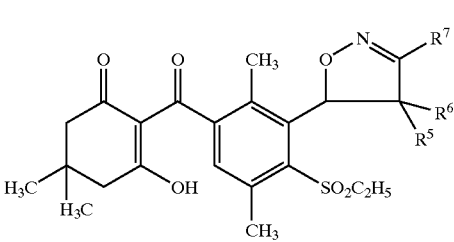

Ia155

Equally particularly preferred are the compounds Ia152., especially the compounds Ia152.1–Ia152.64, which differ Equally particularly preferred are the compounds Ia156., especially the compounds Ia156.1–Ia156.64, which differ from the compounds Ia1.1–Ia1.64 by the fact that $R^1$, $R^3$, $R^{13}$ and $R^{17}$ are methyl and $R^2$ is ethylsulfonyl.

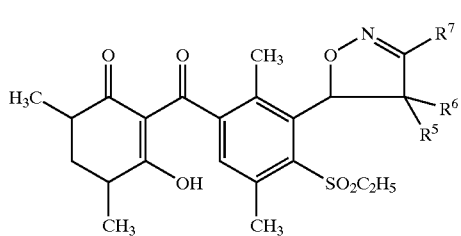

Ia156

Equally particularly preferred are the compounds Ia157., especially the compounds Ia157.1–Ia157.64, which differ from the compounds Ia1.1–Ia1.64 by the fact that $R^1$, $R^3$ and $R^{14}$ are methyl, $R^2$ is ethylsulfonyl and $R^{13}$ is methylthio.

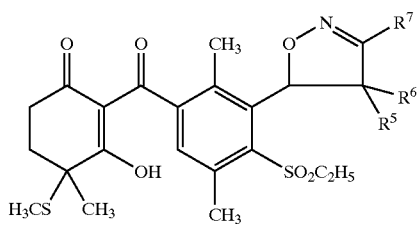

Ia157

Equally particularly preferred are the compounds Ia158., especially the compounds Ia158.1–Ia158.64, which differ from the compounds Ia1.1–Ia1.64 by the fact that $R^1$ and $R^3$ are methyl, $R^2$ is ethylsulfonyl and $R^{14}$ and $R^{18}$ together are ethane-1,2-diyl.

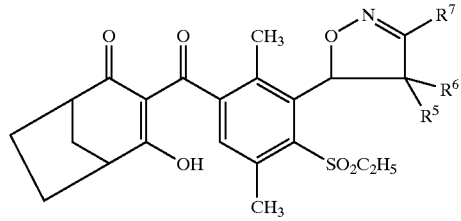

Ia158

Equally particularly preferred are the compounds Ia159., especially the compounds Ia159.1–Ia159.64, which differ from the compounds Ia1.1–Ia1.64 by the fact that $R^1$, $R^3$, $R^{13}$, $R^{14}$, $R^{17}$ and $R^{18}$ are methyl, $R^2$ is ethylsulfonyl and $R^{15}$ and $R^{16}$ together are oxygen.

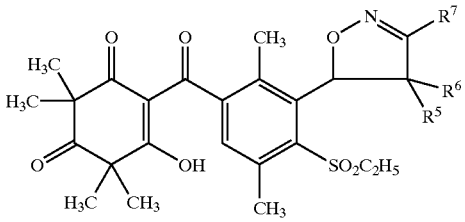

Ia159

Equally particularly preferred are the compounds Ia160., especially the compounds Ia160.1–Ia160.64, which differ from the compounds Ia1.1–Ia1.64 by the fact that $R^1$ and $R^3$ are methyl, $R^2$ is ethylsulfonyl and $R^{15}$ is hydroxyl.

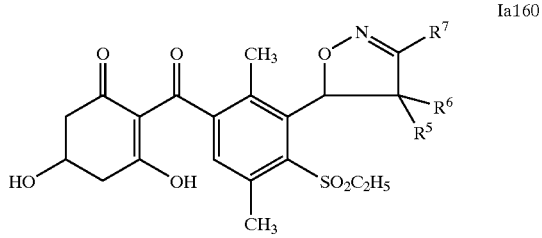

Ia160

Equally particularly preferred are the compounds Ia161., especially the compounds Ia161.1–Ia161.64, which differ from the compounds Ia1.1–Ia1.64 by the fact that $R^1$ and $R^3$ are methyl and $R^2$ is chlorine.

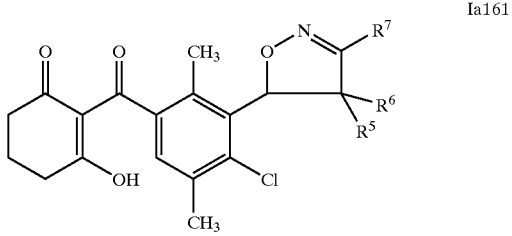

Ia161

Equally particularly preferred are the compounds Ia162., especially the compounds Ia162.1–Ia162.64, which differ from the compounds Ia1.1–Ia1.64 by the fact that $R^1$, $R^3$ and $R^{15}$ are methyl and $R^2$ is chlorine.

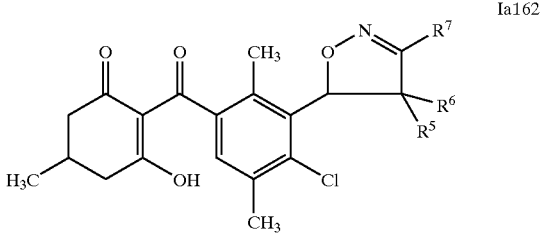

Ia162

Equally particularly preferred are the compounds Ia163., especially the compounds Ia163.1–Ia163.64, which differ from the compounds Ia1.1–Ia1.64 by the fact that $R^1$, $R^3$, $R^{15}$ and $R^{16}$ are methyl and $R^2$ is chlorine.

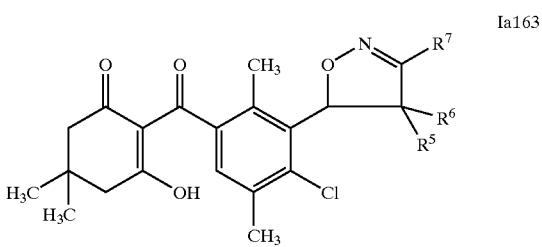

Ia163

Equally particularly preferred are the compounds Ia164., especially the compounds Ia164.1–Ia164.64, which differ from the compounds Ia1.1–Ia1.64 by the fact that $R^1$, $R^3$, $R^{13}$ and $R^{17}$ are methyl and $R^2$ is chlorine.

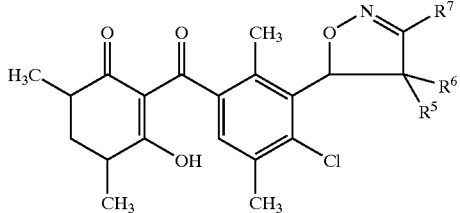

Ia164

Equally particularly preferred are the compounds Ia165., especially the compounds Ia165.1–Ia165.64, which differ from the compounds Ia1.1–Ia1.64 by the fact that $R^1$, $R^3$ and $R^{14}$ are methyl, $R^2$ is chlorine and $R^{13}$ is methylthio.

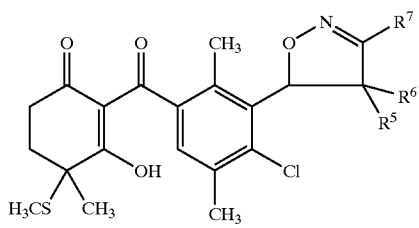

Ia165

Equally particularly preferred are the compounds Ia166., especially the compounds Ia166.1–Ia166.64, which differ from the compounds Ia1.1–Ia1.64 by the fact that $R^1$ and $R^3$ are methyl, $R^2$ is chlorine and $R^{14}$ and $R^{18}$ together are ethane-1,2-diyl.

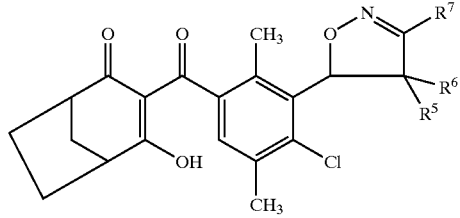

Ia166

Equally particularly preferred are the compounds Ia167., especially the compounds Ia167.1–Ia167.64, which differ from the compounds Ia1.1–Ia1.64 by the fact that $R^1$, $R^3$, $R^{13}$, $R^{14}$, $R^{17}$ and $R^{18}$ are methyl, $R^2$ is chlorine and $R^{15}$ and $R^{16}$ together are oxygen.

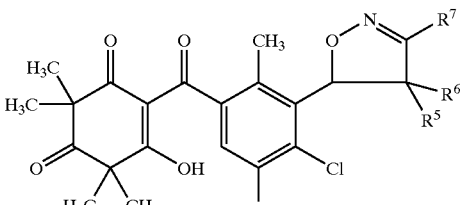

Ia167

Equally particularly preferred are the compounds Ia168., especially the compounds Ia168.1–Ia168.64, which differ from the compounds Ia1.1–Ia1.64 by the fact that $R^1$ and $R^3$ are methyl and $R^{15}$ is hydroxyl.

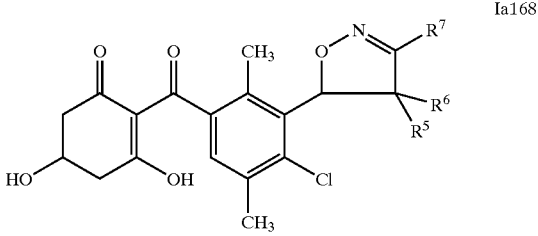

Ia168

In a further preferred embodiment of the compounds of the formula I, the variables, either alone or in combination, have the following meanings:

$R^1$ is halogen, $C_1$–$C_6$-alkyl or $C_1$–$C_6$-alkoxy; preferably halogen such as chlorine or bromine, $C_1$–$C_4$-alkyl such as methyl, ethyl or propyl, $C_1$–$C_4$-alkoxy such as methoxy or ethoxy; especially preferably chlorine, methyl or methoxy;

$R^2$ is halogen or $C_1$–$C_6$-alkylsulfonyl; preferably halogen such as chlorine or bromine or $C_1$–$C_4$-alkylsulfonyl such as methylsulfonyl or ethylsulfonyl; especially preferably chlorine or methylsulfonyl;

$R^3$ is hydrogen;

$R^4$ is hydrogen;

$R^5$ is hydrogen;

$R^6$ is hydrogen;

$R^7$ is $C_1$–$C_6$-alkyl, $C_1$–$C_4$-alkylcarbonyl or $C_1$–$C_4$-alkoxycarbonyl; preferably $C_1$–$C_6$-alkyl such as methyl, ethyl, 1-methylethyl or 1,1-dimethylethyl, methylcarbonyl or ethylcarbonyl, methoxycarbonyl or ethoxycarbonyl;

$R^{12}$ is hydroxyl;

$R^{13}$ is hydrogen or $C_1$–$C_4$-alkyl;

$R^{14}$ is hydrogen or $C_1$–$C_4$-alkyl;

$R^{15}$ is hydrogen or $C_1$–$C_4$-alkyl;

$R^{16}$ is hydrogen or $C_1$–$C_4$-alkyl;

$R^{17}$ is hydrogen or $C_1$–$C_4$-alkyl;

$R^{18}$ is hydrogen or $C_1$–$C_4$-alkyl; or $R^{15}$ and $R^{16}$ together are an oxygen atom; or $R^{14}$ and $R^{18}$ together are $C_1$–$C_5$-alkanediyl, in particular 1,2-ethanediyl.

The 3-(4,5-dihydroisoxazol-5-yl)benzoylcyclohexenones of the formula I can be obtained by various routes, for example by the following process:

Process A:

Reaction of cyclohexenones of the formula II (where $R^{12}$=OH) with an activated carboxylic acid IIIα or a carboxylic acid IIIβ which is preferably activated in situ, to give the acylation product which is subsequently subjected to a rearrangement reaction.

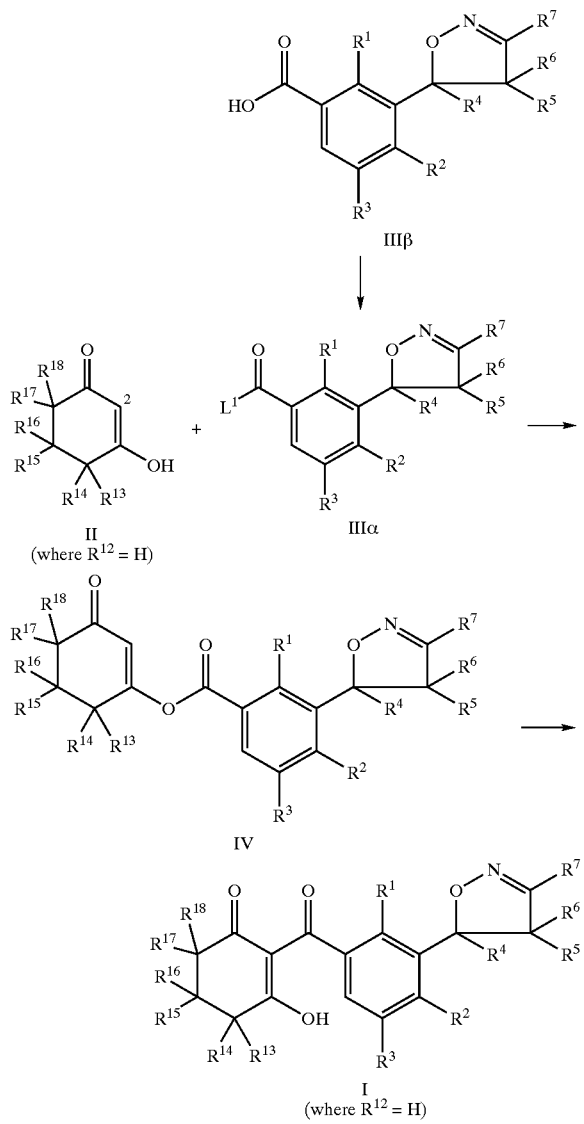

$L^1$ is a nucleophilically displaceable leaving group such as halogen, e.g. bromine or chlorine, hetaryl, e.g. imidazolyl or pyridyl, carboxylate, e.g. acetate, trifluoroacetate and the like.

The activated carboxylic acid can be employed directly, such as in the case of the carbonyl halides, or generated in situ, for example with dicyclohexylcarbodiimide, triphenylphosphane/azodicarboxylic ester, 2-pyridine disulfide/triphenylphosphane, carbonyldiimidazole and the like.

If appropriate, it may be advantageous to carry out the acylation reaction in the presence of a base. The reactants and the auxiliary base are expediently employed in equimolar amounts. An excess of the auxiliary base, for example 1.2 to 2.5 mol equivalents, especially 1.2 to 1.5 mol equivalents, based on II, may be advantageous under certain circumstances.

Auxiliary bases which are suitable are tertiary alkylamines, pyridine or alkali metal carbonates. Solvents which can be employed are, for example, chlorinated hydrocarbons such as methylene chloride, 1,2-dichloroethane, aromatic hydrocarbons such as toluene, xylene, chlorobenzene, ethers such as diethyl ether, methyl tert-butyl ether, tetrahydrofuran, dioxane, polar aprotic solvents such as acetonitrile, dimethylformamide, dimethyl sulfoxide, or esters such as ethyl acetate, or mixtures of these.

If carbonyl halides are employed as activated carboxylic acid component, it may be advantageous to cool the reaction mixture to 0–10° C. when adding this reactant. The mixture is subsequently stirred at 20–100° C., preferably at 25–50° C., until the reaction is complete. Work-up is carried out in the customary fashion, for example the reaction mixture is poured into water and the product of interest is extracted. Solvents which are suitable for this purpose are in particular methylene chloride, diethyl ether and ethyl acetate. After the organic phase has been dried and the solvent has been removed, the crude ester can be employed without further purification in the rearrangement reaction.

Rearrangement of the esters to give the compounds of the formula I is expediently carried out at temperatures of from 20 to 40° C. in a solvent and in the presence of a base and, if appropriate, with the aid of a cyano compound as catalyst.

Solvents which can be used are, for example, acetonitrile, methylene chloride, 1,2-dichloroethane, dioxane, ethyl acetate, toluene or mixtures of these. Preferred solvents are acetonitrile and dioxane.

Suitable bases are tertiary amines such as triethylamine, pyridine or alkali metal carbonates such as sodium carbonate or potassium carbonate, which are preferably employed in equimolar amounts or up to a four-fold excess based on the ester. By preference, triethylamine or alkali metal carbonates are employed, preferably in twice the equimolar ratio based on the ester.

Suitable cyano compounds are inorganic cyanides, such as sodium cyanide, potassium cyanide and organic cyano compounds such as acetone cyanohydrin or trimethylsilyl cyanide. They are employed in an amount of 1 to 50 mol percent based on the ester. Preferably, acetone cyanohydrin or trimethylsilyl cyanide are employed, for example in an amount of 5 to 25, preferably 5 to 15, in particular 10, mol percent based on the ester.

Work-up can be carried out in a conventional manner. For example, the reaction mixture is acidified with dilute mineral acid, such as 5% strength hydrochloric acid or sulfuric acid, and extracted with an organic solvent, for example methylene chloride or ethyl acetate. The organic extract can be extracted with 5–10% strength alkali metal carbonate solution, for example sodium carbonate or potassium carbonate solution. The aqueous phase is acidified, and the precipitate which forms is filtered off with suction and/or extracted with methylene chloride or ethyl acetate, dried and concentrated.

(Examples of the synthesis of hydroxypyrazole esters and of the rearrangement of the esters are given for example in EP-A 282 944 and U.S. Pat. No. 4,643,757).

Process B:

Reaction of 3-(4,5-dihydroisoxazol-5-yl) benzoylcyclohexenones of the formula I (where $R^{12}$=OH, SH) with a compound of the formula V:

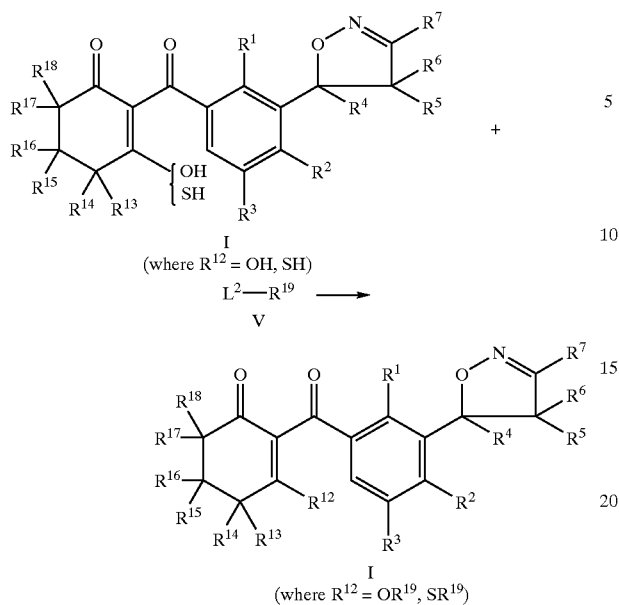

(where $R^{12}$ = OH, SH)

$L^2—R^{19}$
V (where $R^{12}$ = $OR^{19}$, $SR^{19}$)

$L^2$ is a nucleophilically displaceable leaving group such as halogen, e.g. bromine or chlorine, or hetaryl, e.g. imidazolyl, pyridyl, sulfonate.

The compounds of the formula V can be employed directly, such as, for example, in the case of the sulfonyl halides or sulfonic anhydrides, or generated in situ, for example activated sulfonic acids (by means of sulfonic acid and dicyclohexylcarbonyldiimide, carbonyldiimidazole and the like).

As a rule, the starting compounds are employed in an equimolar ratio. However, it may also be advantageous to employ one or the other component in excess.

If appropriate, it may be advantageous to carry out the reaction in the presence of a base. The reactants and the auxiliary base are expediently employed in equimolar amounts. Under certain circumstances, an excess of the auxiliary base, for example 1.5 to 3 mol equivalents based on II, may be advantageous.

Suitable auxiliary bases are tertiary alkylamines such as triethylamine or pyridine, alkali metal carbonates, e.g. sodium carbonate or potassium carbonate, and alkali metal hydrides, e.g. sodium hydride. Triethylamine and pyridine are preferably used.

Examples of suitable solvents are chlorinated hydrocarbons such as methylene chloride or 1,2-dichloroethane, aromatic hydrocarbons, e.g. toluene, xylene or chlorobenzene, ethers such as diethyl ether, methyl tert-butyl ether, tetrahydrofuran or dioxane, polar aprotic solvents such as acetonitrile, dimethylformamide or dimethyl sulfoxide, or esters such as ethyl acetate, or mixtures of these.

As a rule, the reaction temperature is in the range of from 0° C. up to the boiling point of the reaction mixture.

Work-up can be carried out in a conventional manner to give the product.

Process C:

Compounds of the formula I where $R^{12}$=halogen are obtained by reacting compounds of the formula I where $R^{12}$=hydroxyl with a halogenating agent (Hal represents halogen).

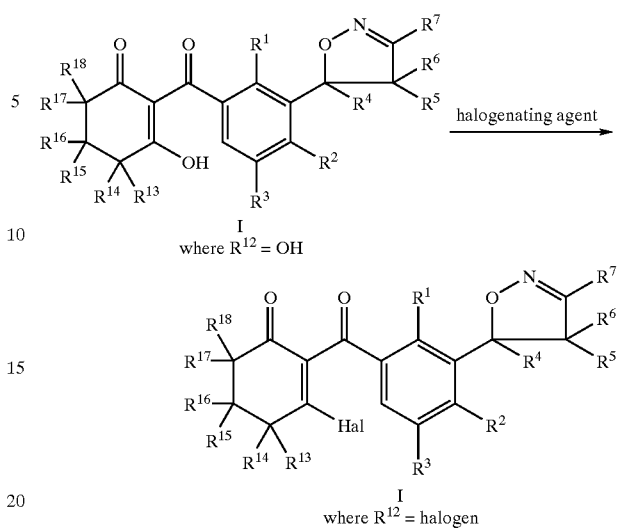

where $R^{12}$ = OH where $R^{12}$ = halogen

Examples of suitable halogating agents are phosgene, diphosgene, triphosgene, thionyl chloride, oxalyl chloride, phosphorus oxychloride, phosphorus pentachloride, mesyl chloride, chloromethylene-N,N-dimethylammonium chloride, oxalyl bromide, phosphorus oxybromide and the like.

As a rule, the starting compounds are employed in an equimolar ratio. It may also be advantageous to employ one or the other component in excess.

Examples of suitable solvents are chlorinated hydrcarbons such as methylene chloride or 1,2-dichloroethane, aromatic hydrocarbons, e.g. toluene, xylene or chlorobenzene, polar aprotic solvents such as acetonitrile, dimethylformamide or dimethyl sulfoxide, or mixtures of these. It is also possible to carry out the reaction without solvent.

As a rule, the reaction temperature is in the range of from 0° C. up to the boiling point of the reaction mixture.

Work-up can be carried out in a conventional manner to give the product.

Process D:

Compounds of the formula I where $R^{12}$=mercapto, $OR^{19}$ or $SR^{19}$ can be obtained by reacting compounds of the formula I where $R^{12}$=halogen with compounds VI in the presence or absence of a base or with or without previous salt formation.

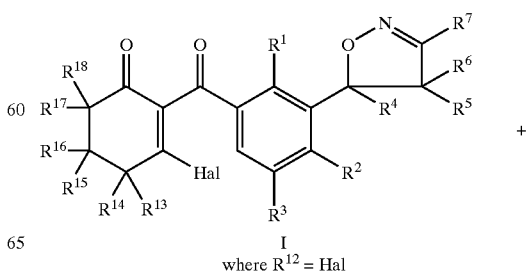

where $R^{12}$ = Hal

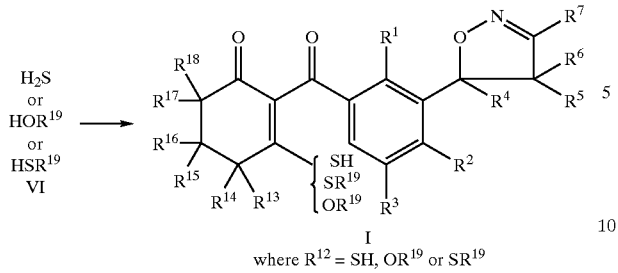

where $R^{12}$ = SH, $OR^{19}$ or $SR^{19}$

As a rule, the starting compounds are employed in an equimolar ratio. However, it may also be advantageous to employ one or the other component in excess.

If appropriate, it may also be advantageous to carry out the reaction in the presence of a base. The reactants and the base are expediently employed in equimolar quantities. An excess of base, for example 1.5 to 3 mol equivalents based on I where $R^8$=Hal, may be advantageous under certain circumstances.

Bases which are suitable are tertiary alkylamines such as triethylamine, aromatic amines such as pyridine, alkali metal carbonates, e.g. sodium carbonate or potassium carbonate, alkali metal hydrogen carbonates such as sodium hydrogen carbonate or potassium hydrogen carbonate, alkali metal alkoxides such as sodium methoxide, sodium ethoxide or potassium tert-butoxide, or alkali metal hydrides such as e.g. sodium hydride. Sodium hydride or potassium tert-butoxide are preferably used.

Examples of suitable solvents are chlorinated hydrocarbons such as methylene chloride or 1,2-dichloroethane, aromatic hydrocarbons, e.g. toluene, xylene or chlorobenzene, ethers such as diethyl ether, methyl tert-butyl ether, tetrahydrofuran or dioxane, polar aprotic solvents such as acetonitrile, dimethylformamide or dimethyl sulfoxide, or mixtures of these.

As a rule, the reaction temperature is in the range of from 0° C. up to the boiling point of the reaction mixture.

Work-up can be carried out in a conventional manner to give the product.

Process E:

Moreover, compounds of the formula I where $R^{12}$=$SOR^{20}$ or $SO_2R^{20}$ can be obtained by reaction with an oxidant.

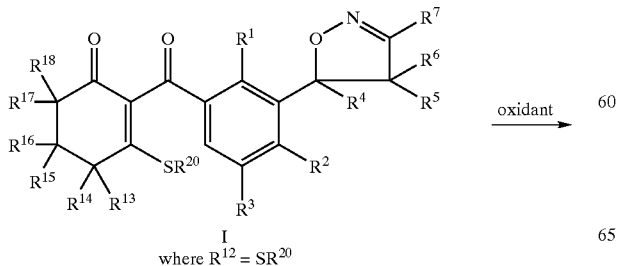

where $R^{12}$ = $SR^{20}$

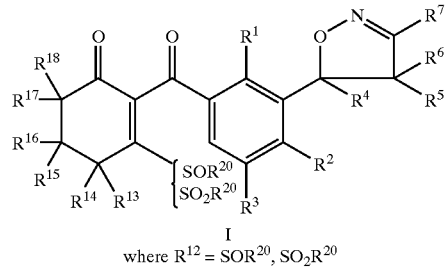

where $R^{12}$ = $SOR^{20}$, $SO_2R^{20}$

Examples of suitable oxidants are m-chloroperbenzoic acid, peroxyacetic acid, trifluoroperoxyacetic acid, hydrogen peroxide, in the presence or absence of a catalyst such as tungstate.

As a rule, the starting compounds are employed in an equimolar ratio. It may be advantageous to employ one or the other component in excess.

Examples of suitable solvents are chlorinated hydrocarbons such as methylene chloride or 1,2-dichloroethane, aromatic hydrocarbons, e.g. toluene, xylene or chlorobenzene, ethers such as diethyl ether, methyl tert-butyl ether, tetrahydrofuran or dioxane, polar aprotic solvents such as acetonitrile or dimethylformamide, or esters such as ethyl acetate, or mixtures of these.

As a rule, the reaction temperature is in the range of from 0° C. up to the boiling point of the reaction mixture.

Work-up can be carried out in a conventional manner to give the product.

The cyclohexenones of the formula II (where $R^{12}$=OH) which are used as starting materials are known or can be prepared by conventional processes (for example EP-A 240 001 and J. Prakt. Chem. 315, 383 (1973)).

3-(4,5-Dihydroisoxazol-5-yl)carboxylic acid derivatives of the formula III are novel,

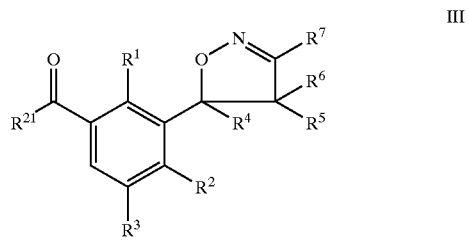

the variables having the following meanings:

$R^1$, $R^2$ are hydrogen, nitro, halogen, cyano, $C_1$–$C_6$-alkyl, $C_1$–$C_6$-haloalkyl, $C_1$–$C_6$-alkoxy, $C_1$–$C_6$-haloalkoxy, $C_1$–$C_6$-alkylthio, $C_1$–$C_6$-haloalkylthio, $C_1$–$C_6$-alkylsulfinyl, $C_1$–$C_6$-haloalkylsulfinyl, $C_1$–$C_6$-alkylsulfonyl or $C_1$–$C_6$-haloalkylsulfonyl;

$R^3$ is hydrogen, halogen or $C_1$–$C_6$-alkyl;

$R^4$ is hydrogen or $C_1$–$C_4$-alkyl;

$R^5$, $R^6$ are hydrogen, halogen, cyano, nitro, $C_1$–$C_4$-alkyl, $C_1$–$C_4$-alkoxy-$C_1$–$C_4$-alkyl, di($C_1$–$C_4$-alkoxy)-$C_1$–$C_4$-alkyl, di($C_1$–$C_4$-alkyl)amino-$C_1$–$C_4$-alkyl, di($C_1$–$C_4$-alkyl)aminoimino-$C_1$–$C_4$-alkyl, hydroxyimino-$C_1$–$C_4$-alkyl, $C_1$–$C_6$-alkoxyimino-$C_1$–$C_4$-alkyl, $C_1$–$C_4$-alkoxycarbonyl-$C_1$–$C_4$-alkyl, $C_1$–$C_4$-alkylthio-$C_1$–$C_4$-alkyl, $C_1$–$C_4$-haloalkyl, $C_1$–$C_4$-cyanoalkyl, $C_3$–$C_8$-cycloalkyl, $C_1$–$C_4$-alkoxy, $C_1$–$C_4$-alkoxy-$C_2$–$C_4$-alkoxy, $C_1$–$C_4$-haloalkoxy, $C_1$–$C_4$-alkylthio, $C_1$–$C_4$-haloalkylthio, di($C_1$–$C_4$-alkyl)amino, $COR^8$, phenyl or benzyl, it being possible for the two last-mentioned substituents to be partially or fully halogenated and/or to have attached to them one to three of the following groups: nitro, cyano, $C_1$–$C_4$-alkyl, $C_1$–$C_4$-haloalkyl, $C_1$–$C_4$-alkoxy or $C_1$–$C_4$-haloalkoxy; or $R^5$ and $R^6$ together form a $C_2$–$C_6$-alkanediyl chain which can be mono- to tetrasubstituted by $C_1$–$C_4$-alkyl and/or can be interrupted by oxygen or an unsubstituted or $C_1$–$C_4$-alkyl-substituted nitrogen;

$R^7$ is halogen, cyano, hydroxyl, $C_1$–$C_6$-alkyl, $C_1$–$C_6$-haloalkyl, $C_1$–$C_6$-alkoxy, $C_1$–$C_6$-haloalkoxy, $C_1$–$C_6$-alkylthio, $C_1$–$C_6$-haloalkylthio, $C_1$–$C_6$-aAlkylsulfinyl, $C_1$–$C_6$-haloalkylsulfinyl, $C_1$–$C_6$-alkylsulfonyl, $C_1$–$C_6$-haloalkylsulfonyl, amino, $C_1$–$C_6$-alkylamino, di($C_1$–$C_6$-alkyl)amino, di($C_1$–$C_4$-alkoxy)methyl, hydroxyimino-$C_1$–$C_4$-alkyl, $C_1$–$C_6$-alkoxyimino-$C_1$–$C_4$-alkyl or $COR^8$;

$R^8$ is hydrogen, $C_1$–$C_4$-alkyl, $C_1$–$C_4$-haloalkyl, hydroxyl, $C_1$–$C_4$-alkoxy, $C_1$–$C_4$-alkoxy-$C_2$–$C_4$-alkoxy, $C_1$–$C_4$-haloalkoxy, $C_3$–$C_6$-alkenyloxy, $C_3$–$C_6$-alkynyloxy or $NR^9R^{10}$;

$R^9$ is hydrogen or $C_1$–$C_4$-alkyl;

$R^{10}$ is $C_1$–$C_4$-alkyl;

$R^{15}$ is hydroxyl or a radical which can be eliminated by hydrolysis.

Examples of radicals which can be eliminated by hydrolysis are alkoxy, phenoxy, alkylthio or phenylthio radicals which can be unsubstituted or substituted, or halides, hetaryl radicals which are bound via nitrogen, or amino, imino radicals which can be unsubstituted or substituted, and the like.

Preferred are 3-(4,5-dihydroisoxazol-5-yl)carbonyl halides of the formula IIIα' where $L^1$=halogen ($\hat{=}$III where $R^{21}$=halogen),

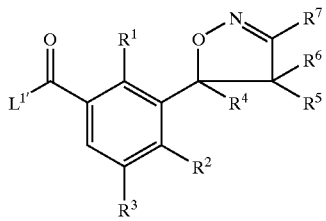

IIIα' where the variables $R^1$ to $R^7$ have the meanings stated under formula III and $L^1$ is halogen, in particular chlorine or bromine.

Equally preferred are 3-(4,5-dihydroisoxazol-5-yl) carboxylic acids of the formula IIIβ ($\hat{=}$III where $R^{21}$=hydroxyl),

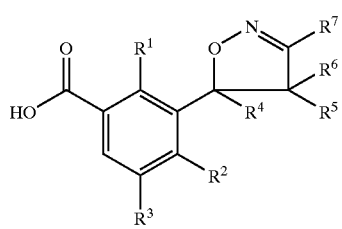

IIIβ where the variables $R^1$ to $R^7$ have the meanings stated under formula III.

Equally preferred are 3-(4,5-dihydroisoxazol-5-yl) carboxylic esters of the formula IIIγ ($\hat{=}$III where $R^{21}$=$C_1$–$C_6$-alkoxy),

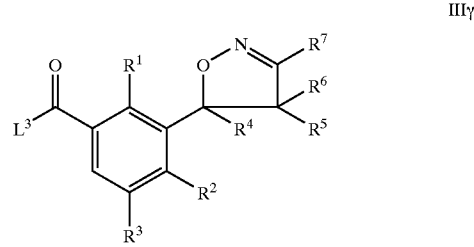

IIIγ where the variables $R^1$ to $R^7$ have the meanings stated under formula III and $L^3$ is $C_1$–$C_6$-alkoxy.

The especially preferred embodiments of the 3-(4,5-dihydroisoxazol-5-yl)carboxylic acid derivatives of the formula III with regard to the variables $R^1$ to $R^7$ correspond to those of the 3-(4,5-dihydroisoxazol-5-yl)cyclohexenones of the formula I.

The 3-(4,5-dihydroisoxazol-5-yl)carbonyl halides of the formula IIIα'(where $L^1$=Cl, Br,) can be prepared in a conventional manner by reacting the 3-(4,5-dihydroisoxazol-5-yl)carboxylic acids of the formula IIIβ with halogenating reagents such as thionyl chloride, thionyl bromide, phosgene, diphosgene, triphosgene, oxalyl chloride or oxalyl bromide.

The 3-(4,5-dihydroisoxazol-5-yl)carboxylic acids of the formula IIIβ can be prepared in a conventional manner from the corresponding esters of the formula IIIγ ($L^3$=$C_1$–$C_6$-alkoxy) by means of acid or alkaline hydrolysis.

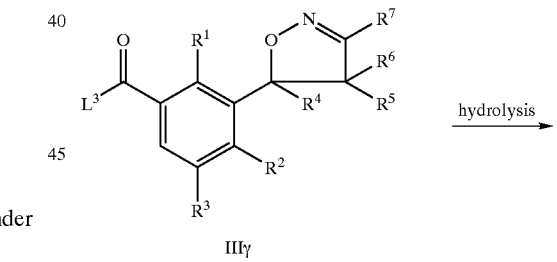

IIIγ hydrolysis

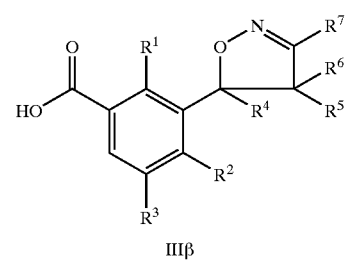

IIIβ

Equally, the 3-(4,5-dihydroisoxazol-5-yl)carboxylic acids of the formula IIIβ can be obtained by reacting corresponding halogen-substituted compounds of the formula VI ($L^4$=Hal), in particular the iodine or bromine compounds, with carbon monoxide and water under elevated pressure in the presence of a palladium, nickel, cobalt or rhodium transition metal catalyst and a base.

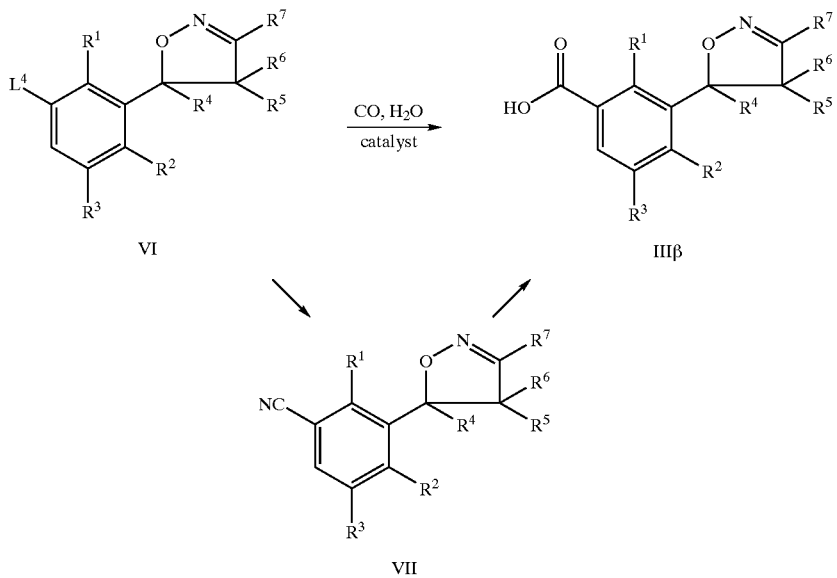

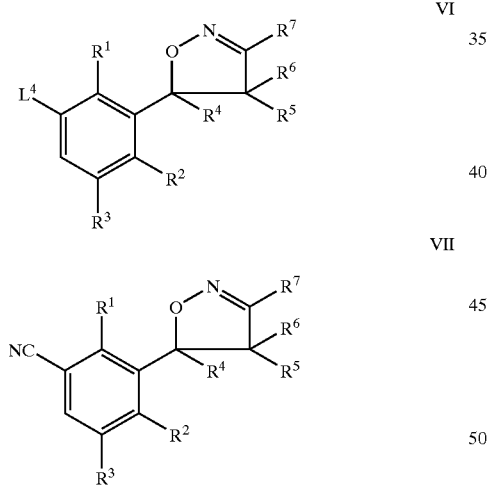

Furthermore, it is possible to convert compounds of the formula VI in a Rosenmund-von Braun reaction into the corresponding nitriles of the formula VII (cf., for example, Org. Synth. Vol. III, 212 (1955)) and to convert the latter into the compounds of the formula IIIβ by subsequently hydrolyzing them.

The compounds of the formula VI or VII are also novel, the variables having the following meanings:

$R^1$, $R^2$ are hydrogen, nitro, halogen, cyano, $C_1$–$C_6$-alkyl, $C_1$–$C_6$-haloalkyl, $C_1$–$C_6$-alkoxy, $C_1$–$C_6$-haloalkoxy, $C_1$–$C_6$-alkylthio, $C_1$–$C_6$-haloalkylthio, $C_1$–$C_6$-alkylsulfinyl, $C_1$–$C_6$-haloalkylsulfinyl, $C_1$–$C_6$-alkylsulfonyl or $C_1$–$C_6$-haloalkylsulfonyl;

$R^3$ is hydrogen, halogen or $C_1$–$C_6$-alkyl;

$R^4$ is hydrogen or $C_1$–$C_4$-alkyl;

$R^5$, $R^6$ are hydrogen, halogen, cyano, nitro, $C_1$–$C_4$-alkyl, $C_1$–$C_4$-alkoxy-$C_1$–$C_4$-alkyl, di($C_1$–$C_4$-alkoxy)-$C_1$–$C_4$-alkyl, di($C_1$–$C_4$-alkyl)amino-$C_1$–$C_4$-alkyl, di($C_1$–$C_4$-alkyl)aminoimino-$C_1$–$C_4$-alkyl, hydroxyimino-$C_1$–$C_4$-alkyl, $C_1$–$C_6$-alkoxyimino-$C_1$–$C_4$-alkyl, $C_1$–$C_4$-alkoxycarbonyl-$C_1$–$C_4$-alkyl, $C_1$–$C_4$-alkylthio-$C_1$–$C_4$-alkyl, $C_1$–$C_4$-haloalkyl, $C_1$–$C_4$-cyanoalkyl, $C_3$–$C_8$-cycloalkyl, $C_1$–$C_4$-alkoxy, $C_1$–$C_4$-alkoxy-$C_2$–$C_4$-alkoxy, $C_1$–$C_4$-haloalkoxy, $C_1$–$C_4$-alkylthio, $C_1$–$C_4$-haloalkylthio, di($C_1$–$C_4$-alkyl)amino, $COR^8$, phenyl or benzyl, it being possible for the two last-mentioned substituents to be partially or fully halogenated and/or to have attached to them one to three of the following groups: nitro, cyano, $C_1$–$C_4$-alkyl, $C_1$–$C_4$-haloalkyl, $C_1$–$C_4$-alkoxy or $C_1$–$C_4$-haloalkoxy; or $R^5$ and $R^6$ together form a $C_2$–$C_6$-alkanediyl chain which can be mono- to tetrasubstituted by $C_1$–$C_4$-alkyl and/or can be interrupted by oxygen or an unsubstituted or $C_1$–$C_4$-alkyl-substituted nitrogen;

$R^7$ is halogen, cyano, hydroxyl, $C_1$–$C_6$-alkyl, $C_1$–$C_6$-haloalkyl, $C_1$–$C_6$-alkoxy, $C_1$–$C_6$-haloalkoxy, $C_1$–$C_6$-alkylthio, $C_1$–$C_6$-haloalkylthio, $C_1$–$C_6$-alkylsulfinyl, $C_1$–$C_6$-haloalkylsulfinyl, $C_1$–$C_6$-alkylsulfonyl, $C_1$–$C_6$-haloalkylsulfonyl, amino, $C_1$–$C_6$-alkylamino, di($C_1$–$C_6$-alkyl)amino, di($C_1$–$C_4$-alkoxy)methyl, hydroxyimino-$C_1$–$C_4$-alkyl, $C_1$–$C_6$-alkoxyimino-$C_1$–$C_4$-alkyl or $COR^8$;

$R^8$ is hydrogen, $C_1$–$C_4$-alkyl, $C_1$–$C_4$-haloalkyl, hydroxyl, $C_1$–$C_4$-alkoxy, $C_1$–$C_4$-alkoxy-$C_2$–$C_4$-alkoxy, $C_1$–$C_4$-haloalkoxy, $C_3$–$C_6$-alkenyloxy, $C_3$–$C_6$-alkynyloxy or $NR^9R^{10}$;

$R^9$ is hydrogen or $C_1$–$C_4$-alkyl;

$R^{10}$ is $C_1$–$C_4$-alkyl; and $L^4$ is halogen.

The particular embodiments of the compounds of the formula VI or VII with regard to the variables $R^1$ to $R^7$ correspond to those of the 3-(4,5-dihydroisoxazol-5-yl) benzoylcyclohexenones of the formula I.

The esters of the formula IIIγ or the halogen compounds of the formula VI can be synthesized by subjecting nitrile oxides and corresponding alkenes of the formula VIII or IX to a 1,3-dipolar cycloaddition reaction.

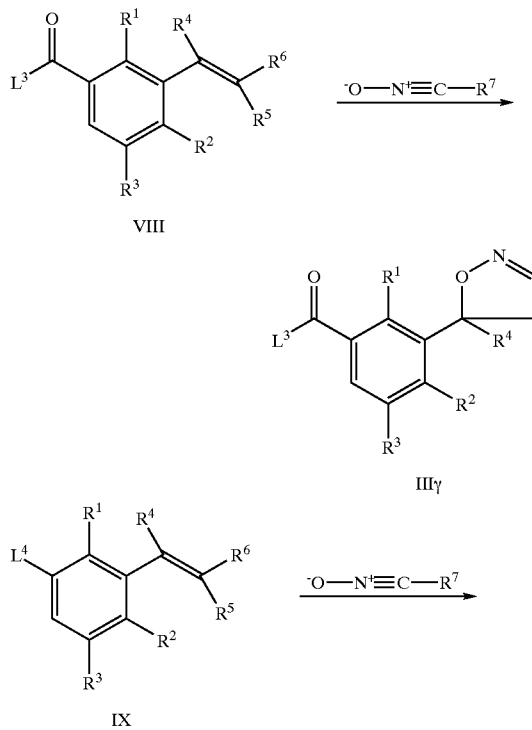

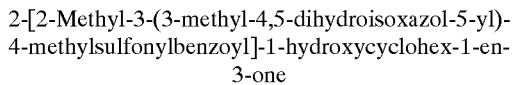

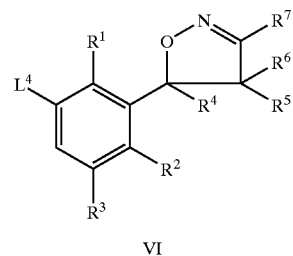

The nitrile oxides are generated in situ in a conventional-manner. The starting materials used for this purpose are, for example, aldoximes (cf., for example, Houben-Weyl X5, p. 858 et seq.) or nitroalkanes (cf., for example, Houben-Weyl E5/2, p. 1594 et seq.). The synthesis of the compounds of the formula VIII or IX is known (cf., for example, WO 98/50337 and WO 98/50366) or is carried out in analogy to processes known from the literature.

PREPARATION EXAMPLES

2-[2-Methyl-3-(3-methyl-4,5-dihydroisoxazol-5-yl)-4-methylsulfonylbenzoyl]-1-hydroxycyclohex-1-en-3-one A solution of 2.3 g (7.7 mmol) of 2-methyl-3-(3-methyl-4,5-dihydroisoxazol-5-yl)-4-methylsulfonylbenzoyl chloride in 50 ml of acetonitrile was added dropwise at 0–5° C. to a solution of 0.86 g (7.7 mmol) of 1-hydroxycyclohex-1-en-3-one and 2.13 ml (15.4 mmol) of triethylamine in 50 ml of acetonitrile. After the mixture had been stirred for three hours at room temperature, a further 0.64 ml (4.6 mmol) of triethylamine and 0.16 g (15 mmol) of trimethylsilyl cyanide were added and the mixture was stirred for twelve hours at room temperature. The reaction mixture was then stirred into 800 ml of water and washed with methylene chloride. The aqueous phase was then brought to pH 4 using 10% strength hydrochloric acid and extracted with methylene chloride. After the organic phase had been dried, the solvent was removed and the residue was taken up in diethyl ether and digested. The resulting residue was filtered off with suction. This gave 1.3 g (3.3 mmol; 43% of theory) of the title compounds.

M.p. 135–140° C.

Tables 2 and 3 show not only the above compound, but also further derivatives of the formula I which were, or can be, prepared analogously.

TABLE 2

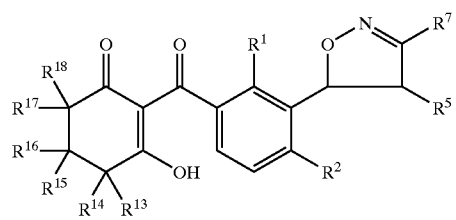

I where $R^3$, $R^4$ and $R^6$ = H

| No. | $R^1$ | $R^2$ | $R^5$ | $R^7$ | $R^{13}$ | $R^{14}$ | $R^{15}$ | $R^{16}$ | $R^{17}$ | $R^{18}$ | Physical data m.p. [° C.] |
|---|---|---|---|---|---|---|---|---|---|---|---|
| 2.1 | Cl | Cl | H | C(CH$_3$)$_3$ | H | H | H | H | H | H | 65–75 |
| 2.2 | Cl | SO$_2$CH$_3$ | H | CO$_2$CH$_2$CH$_3$ | H | H | H | H | H | H | 154–158 |
| 2.3 | Cl | Cl | H | CO$_2$CH$_2$CH$_3$ | H | H | H | H | H | H | 77–81 |
| 2.4 | Cl | Cl | H | CH$_3$ | H | H | H | H | H | H | 84–94 |
| 2.5 | CH$_3$ | SO$_2$CH$_3$ | H | CH$_3$ | H | H | H | H | H | H | 135–140 |
| 2.6 | Cl | SO$_2$CH$_3$ | H | CH$_3$ | H | H | H | H | H | H | 115–125 |
| 2.7 | Cl | Cl | H | CH$_3$ | CH$_3$ | CH$_3$ | =O | | CH$_3$ | CH$_3$ | 82–85 |
| 2.8 | Cl | SO$_2$CH$_3$ | H | CH$_3$ | H | H | CH$_3$ | H | H | H | 190–193 |
| 2.9 | Cl | SO$_2$CH$_3$ | H | CH$_3$ | H | H | CH$_3$ | CH$_3$ | H | H | 114–124 |
| 2.10 | Cl | SO$_2$CH$_3$ | H | CH$_3$ | H | H | H | H | CH$_3$ | CH$_3$ | 164–168 |
| 2.11 | Cl | SO$_2$CH$_3$ | H | CH$_3$ | CH$_3$ | CH$_3$ | =O | | CH$_3$ | CH$_3$ | 103–105 |
| 2.12 | CH$_3$ | SO$_2$CH$_3$ | H | CH$_3$ | CH$_3$ | CH$_3$ | =O | | CH$_3$ | CH$_3$ | 180–200 |

TABLE 2-continued

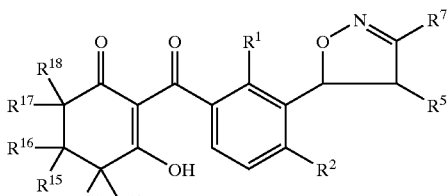

I where $R^3$, $R^4$ and $R^6$ = H

| No. | $R^1$ | $R^2$ | $R^5$ | $R^7$ | $R^{13}$ | $R^{14}$ | $R^{15}$ | $R^{16}$ | $R^{17}$ | $R^{18}$ | Physical data m.p. [° C.] |
|---|---|---|---|---|---|---|---|---|---|---|---|
| 2.13 | $CH_3$ | $SO_2CH_3$ | H | $CH_3$ | H | H | H | H | $CH_3$ | $CH_3$ | 190–195 |
| 2.14 | Cl | Cl | H | $CH_3$ | H | H | $CH_3$ | H | H | H | 81–84 |
| 2.15 | Cl | Cl | H | $CH_3$ | H | H | $CH_3$ | $CH_3$ | H | H | 63–65 |
| 2.16 | Cl | Cl | H | $CH_3$ | H | H | H | H | $CH_3$ | $CH_3$ | 74–84 |
| 2.17 | Cl | Cl | H | $CH_3$ | $CH_3$ | H | H | H | $CH_3$ | H | 80–85 |
| 2.18 | Cl | Cl | H | $CH_3$ | $CH_3$ | H | H | H | $CH_3$ | $CH_3$ | 80–85 |
| 2.19 | $OCH_3$ | $SO_2CH_3$ | H | $CH_3$ | H | H | $CH_3$ | $CH_3$ | H | H | 95–102 |
| 2.20 | $OCH_3$ | $SO_2CH_3$ | H | $CH_3$ | H | H | H | H | H | H | 175–185 |
| 2.21 | $CH_3$ | $SO_2CH_3$ | H | $CH_3$ | H | H | $CH_3$ | H | H | H | 134–138 |
| 2.22 | $CH_3$ | $SO_2CH_3$ | H | $CH_3$ | H | H | $CH_3$ | $CH_3$ | H | H | 183–186 |
| 2.23 | $OCH_3$ | $SO_2CH_3$ | H | $CH_3$ | $CH_3$ | $CH_3$ | =O | | $CH_3$ | $CH_3$ | 165–168 |
| 2.24 | Cl | Cl | H | $COCH_3$ | H | H | H | H | H | H | 73–78 |

TABLE 3

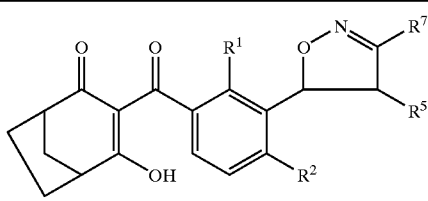

I where $R^3$, $R^4$, $R^{13}$, $R^{15}$, $R^{16}$ and $R^{17}$ = H
$R^{14} + R^{18}$ = —$CH_2$—$CH_2$—

| No. | $R^1$ | $R^2$ | $R^5$ | $R^7$ | Physical data m.p. [° C.] |
|---|---|---|---|---|---|
| 3.1 | Cl | $SO_2CH_3$ | H | $CH_3$ | 107–108 |
| 3.2 | $CH_3$ | $SO_2CH_3$ | H | $CH_3$ | 190–222 |
| 3.3 | Cl | Cl | H | $CH_3$ | 88–92 |
| 3.4 | $OCH_3$ | $SO_2CH_3$ | H | $CH_3$ | 88–106 |
| 3.5 | Cl | Cl | H | $COCH_3$ | 88–95 |

The syntheses of some starting materials are shown hereinbelow:

Methyl 2,4-dichloro-3-(3-t-butyl-4,5-dihydroisoxazol-5-yl)benzoate 17 ml of a 12% strength aqueous sodium hypochlorite solution were added dropwise at room temperature into a vigorously stirred solution of 2.6 g (10 mmol) of methyl 2,4-dichloro-3-ethenylbenzoate and 1 g (10 mmol) of 2,2-dimethylpropional-doxime in 100 ml of dichloromethane. After the mixture had been stirred for in each case 2 hours, two further portions of 0.5 g (5 mmol) of the oxime and 9 ml of the hypochlorite solution were added. Stirring was continued for 12 hours at room temperature, and the reaction mixture was then stirred into 350 ml of water. After extraction with dichloromethane, drying and removal of the solvent, the residue was chromatographed.

Yield: 1.5 g (45% of theory) of yellow resin.

Methyl 2-chloro-3-(3-ethoxycarbonyl-4,5-dihydroisoxazol-5-yl)-4-methylsulfonylbenzoate.

6.4 ml (46 mmol) of triethylamine were added slowly dropwise at room temperature to a solution of 8.5 g (31 mmol) of methyl 2-chloro-3-ethenyl-4-methylsulfonylbenzoate and 7.2 g (46 mmol) of ethyl 2-chloro-2-hydroxyiminoacetate in 200 ml of dichloromethane. After the mixture had been stirred for in each case 2 hours, 3 further portions of in each case 4.8 g (31 mmol) of ethyl 2-chloro-2-hydroxyiminoacetate and then 4.3 ml (31 mmol) of triethylamine were added. Stirring was continued for 12 hours at room temperature, and the reaction mixture was then stirred into 600 ml of water. After extraction with dichloromethane, drying and removal of the solvent, the residue was chromatographed.

Yield: 5.7 g (47% of theory) of clear resin.

2-Chloro-3-(3-methyl-4,5-dihydroisoxazol-5-yl)-4-methylsulfonylbenzoic acid a) Methyl 2-chloro-3-(3-methyl-4,5-dihydroisoxazol-5-yl)-4-methylsulfonylbenzoate.

One spatula-tip full of 4-dimethylaminopyridine was added to a solution of 40 g (145 mmol) of methyl 2-chloro-3-ethenyl-4-methylsulfonylbenzoate and 50 g (220 mmol) of di-t-butyl dicarbonate in 300 ml of acetonitrile, and 50 g (640 mmol) of nitroethane were then added dropwise. After the mixture had been stirred for 12 hours at room temperature, a further 32.8 g (145 mmol) of di-t-butyl dicarbonate and 22.9 g (290 mmol) of nitroethane were added. After a further 12 hours, the solvent was distilled off and the residue was digested with ethyl acetate. Following filtration with suction, 32.1 g of the desired compound remained. A further 6.3 g were obtained from the mother liquor after removal of the solvent followed by chromatography.

Yield: 39.4 g (82% of theory); M.p.: 175° C.

b) Methyl 2-chloro-3-(3-methyl-4,5-dihydroisoxazol-5-yl)-4-methylsulfonylbenzoic acid 69.4 g (174 mmol) of 10% strength sodium hydroxide solution were added to a solution of 38.4 g (116 mmol) of methyl 2-chloro-3-(3-methyl-4,5-dihydroisoxazol-5-yl)-4-methylsulfonylbenzoate in 400 ml of methanol and 400 ml of tetrahydrofuran. The mixture was stirred for 12 hours at room temperature, the solvent volume was reduced to half, and the mixture was poured into 1 1 of water. The pH was brought to 1 using 10% strength hydrochloric acid, and the precipitate which formed was filtered off with suction.

Yield: 35.2 g (96% of theory); M.p.: >220° C.
2-Methyl-3-(3-methyl-4,5-dihydroisoxazol-5-yl)-4-methylsulfonylbenzoic acid
a) 2-Methyl-3-(3-methyl-4,5-dihydroisoxazol-5-yl) methylsulfonylbenzoic acid One spatula-tip full of 4-dimethylaminopyridine was added to a solution of 13.6 g (50 mmol) of 2-methyl-3-ethenyl-4-methylsulfonylbromobenzene and 16.7 g (74 mmol) of di-t-butyl dicarbonate in 100 ml of acetonitrile, and 17.9 g (229 mmol) of nitroethane were then slowly added dropwise. After the mixture had been stirred for 6 hours at room temperature, a further 11.1 g (50 mmol) of di-t-butyl dicarbonate and 7.8 g (100 mmol) of nitroethane were added and the mixture was stirred for 12 hours at room temperature. After the solvent had been removed, the residue was chromatographed.

Yield: 6.4 g (38% of theory)
b) 2-Methyl-3-(3-methyl-4,5-dihydroisoxazol-5-yl)-4-methylsulfonylbenzoic acid 6.4 g (19 mmol) of 2-methyl-3-(3-methyl-4,5-dihydroisoxazol-5-yl)-4-methylsulfonylbromobenzene were dissolved in 65 ml of toluene and 30 ml of water and treated with 240 mg (1 mmol) of palladium acetate, 1.1 g (4 mmol) of tricyclohexylphosphane, 810 mg (19 mmol) of lithium chloride and 5.4 ml (38 mmol) of triethylamine. The resulting solution was then stirred in an autoclave for 36 hours at 140° C. under a carbon monoxide pressure of 20 bar. After cooling the autoclave and releasing the pressure, insoluble constituents were removed by filtration, and the phases were separated. The organic phase was subsequently extracted twice with water containing a little triethylamine. The combined aqueous phases were then brought to pH 1 using 10% hydrochloric acid, and the precipitate which formed was filtered off.

Yield: 2.5 g (44% of theory); M.p.: 199-205° C.

Table 4 which follows lists not only the above-described compounds, but also further 3-(4,5-dihydroisoxazol-5-yl) carboxylic acid derivatives of the formula III which are prepared, or can be prepared, analogously.

TABLE 4

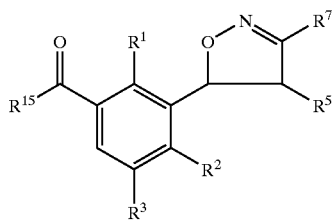

I where $R^4$ and $R^6$ = H

| No. | $R^1$ | $R^2$ | $R^3$ | $R^5$ | $R^7$ | $R^{15}$ | Physical data [° C.] |
|---|---|---|---|---|---|---|---|
| 4.1 | Cl | Cl | H | H | $CH_3$ | $OCH_3$ | Resin |
| 4.2 | Cl | Cl | H | H | $CH_3$ | OH | Resin |
| 4.3 | Cl | Cl | H | H | $C(CH_3)_3$ | $OCH_3$ | Resin |
| 4.4 | Cl | Cl | H | H | $C(CH_3)_3$ | OH | |
| 4.5 | Cl | $SO_2CH_3$ | H | H | $C(CH_3)_3$ | $OCH_3$ | 54–55 |
| 4.6 | Cl | $SO_2CH_3$ | H | H | $C(CH_3)_3$ | OH | 97–100 |
| 4.7 | Cl | Cl | H | H | COOEt | $OCH_3$ | Oil |
| 4.8 | Cl | Cl | H | H | COOEt | OH | |

TABLE 4-continued

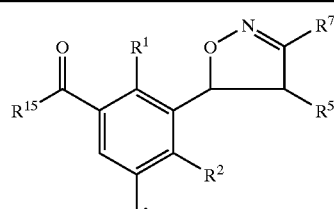

I where $R^4$ and $R^6$ = H

| No. | $R^1$ | $R^2$ | $R^3$ | $R^5$ | $R^7$ | $R^{15}$ | Physical data [° C.] |
|---|---|---|---|---|---|---|---|
| 4.9 | Cl | $SO_2CH_3$ | H | H | COOEt | $OCH_3$ | Resin |
| 4.10 | Cl | $SO_2CH_3$ | H | H | COOEt | OH | 82–90 |
| 4.11 | Cl | Cl | H | H | COOH | OH | 182–183 |
| 4.12 | Cl | Cl | H | H | $CF_3$ | $OCH_3$ | Oil |
| 4.13 | Cl | Cl | H | H | $CF_3$ | OH | |
| 4.14 | Cl | $SO_2CH_3$ | H | H | $CH_3$ | $OCH_3$ | 175 |
| 4.15 | Cl | $SO_2CH_3$ | H | H | $CH_3$ | OH | >220 |
| 4.16 | $CH_3$ | $SO_2CH_3$ | H | H | $CH_3$ | $OCH_3$ | 120–121 |
| 4.17 | $CH_3$ | $SO_2CH_3$ | H | H | $CH_3$ | OH | 199–205 |
| 4.18 | Cl | $SO_2CH_3$ | H | H | $CH(OC_2H_5)_2$ | $OCH_3$ | Resin |
| 4.19 | Cl | $SO_2CH_3$ | H | H | $CH(OC_2H_5)_2$ | OH | |
| 4.20 | Cl | $SO_2CH_3$ | H | H | CHO | $OCH_3$ | |
| 4.21 | Cl | $SO_2CH_3$ | H | H | CHO | OH | |
| 4.22 | Cl | Cl | H | $CH_3$ | $C(CH_3)_3$ | $OCH_3$ | |
| 4.23 | Cl | Cl | H | $CH_3$ | $C(CH_3)_3$ | OH | |
| 4.24 | Cl | Cl | H | H | $COCH_3$ | $OCH_3$ | |
| 4.25 | Cl | Cl | H | H | $COCH_3$ | OH | |
| 4.26 | Cl | Cl | H | H | Cl | $OCH_3$ | |
| 4.27 | Cl | Cl | H | H | Cl | OH | |

The 3-(4,5-dihydroisoxazol-5-yl)benzoylcyclohexenones of the formula I and their agriculturally useful salts, both in the form of the isomer mixtures and in the form of the pure isomers, are suitable as herbicides. The herbicidal compositions comprising compounds of the formula I effect very good control of vegetation on non-crop areas, especially at high rates of application. In crops such as wheat, rice, maize, soya and cotton, they act against broad-leaved weeds and grass weeds without damaging the crop plants significantly. This effect is observed especially at low application rates.

Depending on the application method in question, the compounds of the formula I or herbicidal compositions comprising them can additionally be employed in a further number of crop plants for eliminating undesired plants. Examples of suitable crop plants are:

*Allium cepa, Ananas comosus, Arachis hypogaea, Asparagus officinalis, Beta vulgaris* spec. *altissima, Beta vulgaris* spec. *rapa, Brassica napus* var. *napus, Brassica napus* var. *napobrassica, Brassica rapa* var. *silvestris, Camellia sinensis, Carthamus tinctorius, Carya illinoinensis, Citrus limon, Citrus sinensis, Coffea arabica (Coffea canephora, Coffea liberica), Cucumis sativus, Cynodon dactylon, Daucus carota, Elaeis guineensis, Fragaria vesca, Glycine max, Gossypium hirsutum, (Gossypium arboreum, Gossypium herbaceum, Gossypium vitifolium), Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus* spec., *Manihot esculenta, Medicago sativa, Musa* spec., *Nicotiana tabacum (N.rustica), Olea europaea, Oryza sativa, Phaseolus lunatus, Phaseolus vulgaris, Picea abies, Pinus* spec., *Pisum sativum, Prunus avium, Prunus persica, Pyrus communis, Ribes sylvestre, Ricinus communis, Saccharum officinarum, Secale cereale, Solanum tuberosum, Sorghum bicolor (s. vulgare), Theobroma cacao, Trifolium*

*pratense, Triticum aestivum, Triticum durum, Vicia faba, Vitis vinifera* and *Zea mays.*

Moreover, the compunds of the formula I can also be used in crops which tolerate the action of herbicides due to breeding, including recombinant methods.

The compounds of the formula I, or the herbicidal compositions comprising them, can be employed, for example, in the form of directly sprayable aqueous solutions, powders, suspensions, also highly-concentrated aqueous, oily or other suspensions or dispersions, emulsions, oil dispersions, pastes, dusts, materials for spreading or granules, by means of spraying, atomizing, dusting, spreading or pouring, or as a seed treatment or by mixing with the seed. The use forms depend on the intended purposes; in any case, they should guarantee the finest possible distribution of the active ingredients according to the invention.

The herbicidal compositions comprise a herbicidally active amount of at least one compound of the formula I or of an agriculturally useful salt of I and adjuvants conventionally used for the formulation of crop protection products.

Suitable inert auxiliaries are essentially: mineral oil fractions of medium to high boiling point such as kerosene and diesel oil, furthermore coal tar oils and oils of vegetable or animal origin, aliphatic, cyclic and aromatic hydrocarbons, e.g. paraffins, tetrahydronaphthalene, alkylated naphthalenes and their derivatives, alkylated benzenes and their derivatives, alcohols such as methanol, ethanol, propanol, butanol and cyclohexanol, ketones such as cyclohexanone, strongly polar solvents, e.g. amines such as N-methylpyrrolidone, and water.

Aqueous use forms can be prepared from emulsion concentrates, suspensions, pastes, wettable powders or water-dispersable granules by adding water. To prepare emulsions, pastes or oil dispersions, the 3-(4,5-dihydroisoxazol-5-yl)benzoylcyclohexenones, as such or dissolved in an oil or solvent, can be homogenized in water by means of wetters, tackifiers, dispersants or emulsifiers. However, it is also possible to prepare concentrates composed of active substance, wetter, tackifier, dispersant or emulsifier and, if appropriate, solvent or oil which are suitable for dilution with water.

Suitable surfactants (adjuvants) are the alkali metal salts, alkaline earth metal salts and ammonium salts of aromatic sulfonic acids, e.g. ligno-, phenol-, naphthalene- and dibutylnaphthalenesulfonic acid, and of fatty acids, of alkyl- and alkylarylsulfonates, of alkyl sulfates, lauryl ether sulfates and fatty alcohol sulfates, and salts of sulfated hexa-, hepta- and octadecanols, and of fatty alcohol glycol ether, condensates of sulfonated naphthalene and its derivatives with formaldehyde, condensates of naphthalene, or of the naphthalenesulfonic acids, with phenol and formaldehyde, polyoxyethylene octylphenol ether, ethoxylated isooctyl-, octyl- or nonylphenol, alkylphenyl and tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignin-sulfite waste liquors or methylcellulose.

Powders, materials for spreading and dusts can be prepared by mixing or concomitantly grinding the active substances with a solid carrier.

Granules, for example coated granules, impregnated granules and homogeneous granules, can be prepared by binding the active ingredients to solid carriers. Solid carriers are mineral earths such as silicas, silica gels, silicates, talc, kaolin, limestone, lime, chalk, bole, loess, clay, dolomite, diatomaceous earth, calcium sulfate, magnesium sulfate, magnesium oxide, ground synthetic materials, fertilizers such as ammonium sulfate, ammonium phosphate, ammonium nitrate, ureas and products of vegetable origin such as cereal meal, tree bark meal, wood meal and nutshell meal, cellulose powders or other solid carriers.

The concentrations of the compounds of the formula I in the ready-to-use products can be varied within wide ranges. In general, the formulations comprise approximately from 0.001 to 98% by weight, preferably 0.01 to 95% by weight, of at least one active ingredient. The active ingredients are employed in a purity of from 90% to 100%, preferably 95% to 100% (according to NMR spectrum).

The formulation examples below illustrate the preparation of such products:

I. 20 parts by weight of the compound No. 2.5 are dissolved in a mixture composed of 80 parts by weight of alkylated benzene, 10 parts by weight of the adduct of 8 to 10 mol of ethylene oxide and 1 mol of oleic acid N-monoethanolamide, 5 parts by weight of calcium dodecylbenzenesulfonate and 5 parts by weight of the adduct of 40 mol of ethylene oxide and 1 mol of castor oil. Pouring the solution into 100000 parts by weight of water and finely distributing it therein gives an aqueous dispersion which comprises 0.02% by weight of the active ingredient.

II. 20 parts by weight of the compound No. 2.9 are dissolved in a mixture composed of 40 parts by weight of cyclohexanone, 30 parts by weight of isobutanol, 20 parts by weight of the adduct of 7 mol of ethylene oxide and 1 mol of isooctylphenol and 10 parts by weight of the adduct of 40 mol of ethylene oxide and 1 mol of castor oil. Pouring the solution into 100000 parts by weight of water and finely distributing it therein gives an aqueous dispersion which comprises 0.02% by weight of the active ingredient.

III. 20 parts by weight of the active ingredient No. 2.5 are dissolved in a mixture composed of 25 parts by weight of cyclohexanone, 65 parts by weight of a mineral oil fraction of boiling point 210 to 280° C. and 10 parts by weight of the adduct of 40 mol of ethylene oxide and 1 mol of castor oil. Pouring the solution into 100000 parts by weight of water and finely distributing it therein gives an aqueous dispersion which comprises 0.02% by weight of the active ingredient.

IV. 20 parts by weight of the active ingredient No. 2.9 are mixed thoroughly with 3 parts by weight of sodium diisobutylnaphthalenesulfonate, 17 parts by weight of the sodium salt of a lignosulfonic acid from a sulfite waste liquor and 60 parts by weight of pulverulent silica gel, and the mixture is ground in a hammer mill. Finely distributing the mixture in 20000 parts by weight of water gives a spray mixture which comprises 0.1% by weight of the active ingredient.

V. 3 parts by weight of the active ingredient No. 2.5 are mixed with 97 parts by weight of finely divided kaolin. This gives a dust which comprises 3% by weight of the active ingredient.

VI. 20 parts by weight of the active ingredient No. 2.9 are mixed intimately with 2 parts by weight of calcium dodecylbenzenesulfonate, 8 parts by weight of fatty alcohol polyglycol ether, 2 parts by weight of the sodium salt of a phenol/urea/formaldehyde condensate and 68 parts by weight of a paraffinic mineral oil. This gives a stable oily dispersion.

VII. 1 part by weight of the active ingredient No. 2.5 is dissolved in a mixture composed of 70 parts by weight of cyclohexanone, 20 parts by weight of ethoxylated isooctylphenol and 10 parts by weight of ethoxylated castor oil. This gives a stable emulsion concentrate.

VIII,. 1 part by weight of the active ingredient No. 2.4 is dissolved in a mixture composed of 80 parts by weight of cyclohexanone and 20 parts by weight of Wettol® EM 31 (=nonionic emulsifier based on ethoxylated castor oil). This gives a stable emulsion concentrate.

The compounds of the formula I or the herbicidal compositions can be applied pre-emergence, post-emergence or together with the seed of a crop plant. It is also possible to apply the compounds of the formula I or the herbicidal compositions by sowing the seed, of a crop plant, which has been pretreated with the herbicidal compositions or active ingredients. If the active ingredients are less well tolerated by certain crop plants, application techniques may be used in which the herbicidal compositions are sprayed with the aid of the spraying equipment in such a way that they come into very little contact, if any, with the leaves of the sensitive crop plants, while the active ingredients reach the leaves of undesired plants growing underneath, or the naked soil surface (post-directed, lay-by).

Depending on the intended aim of the control measures, the season, the target plants and the growth stage, the application rates of compound of the formula I are from 0.001 to 3.0, preferably from 0.01 to 1.0, kg of active substance (a.s.) per ha.

To widen the spectrum of action and to achieve synergistic effects, the 3-(4,5-dihydroisoxazol-5-yl) benzoylcyclohexenones of the formula I can be mixed with a large number of representatives of other groups of active ingredients which act as herbicides or as growth regulators and applied together with these. Suitable components in mixtures are, for example, 1,2,4-thiadiazoles, 1,3,4-thiadiazoles, amides, aminophosphoric acid and its derivatives, aminotriazoles, anilides, aryloxy-/heteroaryloxyalkanoic acids and their derivatives, benzoic acid and its derivatives, benzothiadiazinones, 2-(hetaroyl/aroyl)-1,3-cyclohexanediones, heteroaryl aryl ketones, benzylisoxazolidinones, meta-$CF_3$-phenyl derivatives, carbamates, quinolinecarboxylic acid and its derivatives, chloroacetanilides, cyclohexenone oxime ether derivatives, diazines, dichloropropionic acid and its derivatives, dihydrobenzofurans, dihydrofuran-3-ones, dinitroanilines, dinitrophenols, diphenyl ethers, dipyridyls, halocarboxylic acids and their derivatives, ureas, 3-phenyluracils, imidazoles, imidazolinones, N-phenyl-3,4,5,6-tetrahydrophthalimides, oxadiazoles, oxiranes, phenols, aryloxy- and heteroaryloxyphenoxypropionic esters, phenylacetic acid and its derivatives, phenylpropionic acid and its derivatives, pyrazoles, phenylpyrazoles, pyridazines, pyridinecarboxylic acid and its derivatives, pyrimidyl ethers, sulfonamides, sulfonylureas, triazines, triazinones, triazolinones, triazolecarboxamides and uracils.

Moreover, it may be advantageous to apply the compounds of the formula I, alone or in combination with other herbicides, or in the form of a mixture with other crop protection agents, for example with agents for controlling pests or phytopathogenic fungi or bacteria. Also of interest is the miscibility with mineral salt solutions, which are employed for treating nutritional and trace element deficiencies. Nonphytotoxic oils and oil concentrates can also be added.

USE EXAMPLES

The herbicidal action of the 3-(4,5-dihydroisoxazol-5-yl) benzoylcyclohexenones of the formula I was demonstrated by the following greenhouse experiments:

The culture containers used were plastic flower pots containing loamy sand with approximately 3.0% of humus as substrate. The seeds of the test plant were sown separately for each species.

For the pre-emergence treatment, the active ingredients, which were suspended or emulsified in water, were applied directly after sowing by means of finely distributing nozzles. The containers were irrigated gently to promote germination and growth and subsequently covered with transparent plastic hoods until the plants had rooted. This cover caused uniform germination of the test plants unless this was adversely affected by the active ingredients.

For the post-emergence treatment, the test plants were first grown to a plant height of from 3 to 15 cm, depending on the plant habit, and only then treated with the active ingredients which had been suspended or emulsified in water. To this end, the test plants were either sown directly and grown in the same containers, or they were first grown separately as seedlings and transplanted into the test containers a few days prior to the treatment. The rate of application for the post-emergence the treatment was 125 or 62.5 g of a.s. (active substance) per ha.

Depending on the species, the plants were kept at temperatures of from 10 to 25° C. or from 20 to 35° C. The test period extended over 2 to 4 weeks. During this time, the plants were tended, and their response to the individual treatments was evaluated.

Evaluation was carried out using a scale of from 0 to 100. 100 means no emergence of the plants, or complete destruction of at least the aerial parts, and 0 means no damage or normal course of growth.

The plants used in the greenhouse experiments belonged to the following species:

| Scientific name | Common name |
| --- | --- |
| Amaranthus retroflexus | redroot pigweed |
| Chenopodium album | lambsquarters (goosefoot) |
| Digitaria sanguinalis | hairy fingergrass |
| Panicum dichotomiflorum | fall panicum |
| Polygonum persicaria | ladysthumb |
| Solanum nigrum | black nightshade |
| Stellaria media | common chickweed |
| Matricaria | false chamomile |
| Brachiaria platyphylla | broadleaf signal grass |
| Lamium amplexicaule | henbit |

When rates of application of 125 or 62.5 g/ha a.s. were employed, the compound 2.4 was very effective against *Brachiaria platyphylla*, lambsquarters, Lamium amplexicaule, chamomile and common chickweed. Equally, the compound 2.9 controlled redroot pigweed, lambsquarters, hairy fingergrass, ladysthumb and fall panicum very efficiently under analogous conditions. Used pre-emergence at application rates of 125 or 62.5 g/ha, the compound 2.5 controls redroot pigweed, hairy fingergrass, lambsquarters and black nightshade highly efficiently.

We claim:

1. A 3-(4,5-dihydroisoxazol-5-yl)benzoylcyclohexenone of the formula I

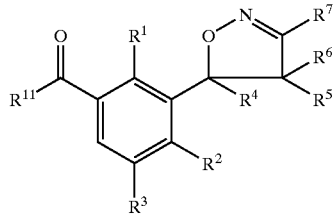

in which the variables have the following meanings:

$R^1$, $R^2$ are hydrogen, nitro, halogen, cyano, $C_1$–$C_6$-alkyl, $C_1$–$C_6$-haloalkyl, $C_1$–$C_6$-alkoxy, $C_1$–$C_6$-haloalkoxy, $C_1$–$C_6$-alkylthio, $C_1$–$C_6$-haloalkylthio, $C_1$–$C_6$-alkylsulfinyl, $C_1$–$C_6$-haloalkylsulfinyl, $C_1$–$C_6$-alkylsulfonyl or $C_1$–$C_6$-haloalkylsulfonyl;

$R^3$ is hydrogen, halogen or $C_1$–$C_6$-alkyl;

$R^4$ is hydrogen or $C_1$–$C_4$-alkyl;

$R^5$, $R^6$ are hydrogen, halogen, cyano, nitro, $C_1$–$C_4$-alkyl, $C_1$–$C_4$-alkoxy-$C_1$–$C_4$-alkyl, di($C_1$–$C_4$-alkoxy)-$C_1$–$C_4$-alkyl, di($C_1$–$C_4$-alkyl)amino-$C_1$–$C_4$-alkyl, di($C_1$–$C_4$-alkyl)aminoimino-$C_1$–$C_4$-alkyl, hydroxyimino-$C_1$–$C_4$-alkyl, $C_1$–$C_6$-alkoxyimino-$C_1$–$C_4$-alkyl, $C_1$–$C_4$-alkoxycarbonyl-$C_1$–$C_4$-alkyl, $C_1$–$C_4$-alkylthio-$C_1$–$C_4$-alkyl, $C_1$–$C_4$-haloalkyl, $C_1$–$C_4$-cyanoalkyl, $C_3$–$C_8$-cycloalkyl, $C_1$–$C_4$-alkoxy, $C_1$–$C_4$-alkoxy-$C_2$–$C_4$-alkoxy, $C_1$–$C_4$-haloalkoxy, $C_1$–$C_4$-alkylthio, $C_1$–$C_4$-haloalkylthio, di($C_1$–$C_4$-alkyl)amino, $COR^8$, phenyl or benzyl, it being possible for the two last-mentioned substituents to be partially or fully halogenated and/or to have attached to them one to three of the following groups: nitro, cyano, $C_1$–$C_4$-alkyl, $C_1$–$C_4$-haloalkyl, $C_1$–$C_4$-alkoxy or $C_1$–$C_4$-haloalkoxy; or $R^5$ and $R^6$ together form a $C_2$–$C_6$-alkanediyl chain which can be mono- to tetrasubstituted by $C_1$–$C_4$-alkyl and/or can be interrupted by oxygen or by unsubstituted or $C_1$–$C_4$-alkyl-substituted nitrogen;

$R^7$ is halogen, cyano, hydroxyl, $C_1$–$C_6$-alkyl, $C_1$–$C_6$-haloalkyl, $C_1$–$C_6$-alkoxy, $C_1$–$C_6$-haloalkoxy, $C_1$–$C_6$-alkylthio, $C_1$–$C_6$-haloalkylthio, $C_1$–$C_6$-alkylsulfinyl, $C_1$–$C_6$-haloalkylsulfinyl, $C_1$–$C_6$-alkylsulfonyl, $C_1$–$C_6$-haloalkylsulfonyl, amino, $C_1$–$C_6$-alkylamino, di($C_1$–$C_6$-alkyl)amino, di($C_1$–$C_4$-alkoxy)methyl, hydroxyimino-$C_1$–$C_4$-alkyl, $C_1$–$C_6$-alkoxyimino-$C_1$–$C_4$-alkyl or $COR^8$;

$R^8$ is hydrogen, $C_1$–$C_4$-alkyl, $C_1$–$C_4$-haloalkyl, hydroxyl, $C_1$–$C_4$-alkoxy, $C_1$–$C_4$-alkoxy-$C_2$–$C_4$-alkoxy, $C_1$–$C_4$-haloalkoxy, $C_3$–$C_6$-alkenyloxy, $C_3$–$C_6$-alkynyloxy or $NR^9R^{10}$;

$R^9$ is hydrogen or $C_1$–$C_4$-alkyl;

$R^{10}$ is $C_1$–$C_4$-alkyl;

$R^{11}$ is a cyclohexenone of the formula II

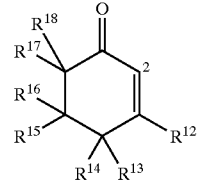

which is linked in the 2-position and where $R^{12}$ is hydroxyl, mercapto, halogen, $OR^{19}$, $SR^{19}$, $SOR^{20}$ or $SO_2R^{20}$;

$R^{13}$, $R^{17}$ are hydrogen, $C_1$–$C_4$-alkyl, $C_1$–$C_4$-alkylthio or $C_1$–$C_4$-alkoxycarbonyl;

$R^{14}$, $R^{16}$, $R^{18}$ are hydrogen or $C_1$–$C_4$-alkyl;

$R^{15}$ is hydrogen, hydroxyl, halogen, $C_1$–$C_6$-alkyl, $C_1$–$C_6$-haloalkyl, di($C_1$–$C_6$-alkoxy)methyl, ($C_1$–$C_6$-alkoxy)($C_1$–$C_6$-alkylthio)methyl, di($C_1$–$C_6$-alkylthio)methyl, $C_1$–$C_6$-alkoxy, $C_1$–$C_6$-haloalkoxy, $C_1$–$C_6$-alkylthio, $C_1$–$C_6$-haloalkylthio, $C_1$–$C_6$-alkoxycarbonyl, $C_1$–$C_6$-haloalkoxycarbonyl, 1,3-dioxolan-2-yl, 1,3-dioxan-2-yl, 1,3-oxathiolan-2-yl, 1,3-oxathian-2-yl, 1,3-dithiolan-2-yl or 1,3-dithian-2-yl, it being possible for the six last-mentioned radicals to have attached to them one, two or three substituents selected from amongst $C_1$–$C_4$-alkyl; or $R^{13}$ and $R^{14}$ or $R^{17}$ and $R^{18}$ together are $C_1$–$C_5$-alkanediyl which can have attached to it one, two or three substituents selected from amongst halogen, cyano, $C_1$–$C_4$-alkyl, $C_1$–$C_4$-haloalkyl or $C_1$–$C_4$-alkoxycarbonyl;

$R^{14}$ and $R^{15}$ or $R^{15}$ and $R^{18}$ together are a chemical bond or $C_1$–$C_5$-alkanediyl which can have attached to it one, two or three substituents selected from amongst halogen, cyano, $C_1$–$C_4$-alkyl, $C_1$–$C_4$-haloalkyl or $C_1$–$C_4$-alkoxycarbonyl; or $R^{14}$ and $R^{18}$ together are $C_1$–$C_5$-alkanediyl which can have attached to it one, two or three substituents selected from amongst halogen, cyano, $C_1$–$C_4$-alkyl, $C_1$–$C_4$-haloalkyl or $C_1$–$C_4$-alkoxycarbonyl; or $R^{15}$ and $R^{16}$ together are —O—$(CH_2)_p$—O—, —O—$(CH_2)_p$—S—, —S—$(CH_2)_p$—S—, —O—$(CH_2)_q$— or —S—$(CH_2)_q$—, each of which can have attached to it one, two or three substituents selected from amongst halogen, cyano, $C_1$–$C_4$-alkyl, $C_1$–$C_4$-haloalkyl or $C_1$–$C_4$-alkoxycarbonyl; or $R^{15}$ and $R^{16}$ together are an oxygen atom;

$R^{19}$ is $C_1$–$C_6$-alkyl, $C_3$–$C_6$-alkenyl, $C_3$–$C_6$-haloalkenyl, $C_3$–$C_6$-alkynyl, $C_3$–$C_6$-cycloalkyl, $C_1$–$C_{20}$-alkylcarbonyl, $C_2$–$C_{20}$-alkenylcarbonyl, $C_2$–$C_6$-alkynylcarbonyl, $C_1$–$C_6$-alkoxycarbonyl, $C_3$–$C_6$-alkenyloxycarbonyl, $C_3$–$C_6$-alkynyloxycarbonyl, $C_1$–$C_6$-alkylthiocarbonyl, $C_1$–$C_6$-alkylaminocarbonyl, $C_3$–$C_6$-alkenylaminocarbonyl, $C_3$–$C_6$-alkynylaminocarbonyl, N,N-di($C_1$–$C_6$-alkyl)aminocarbonyl, N-($C_3$–$C_6$-alkenyl)-N-($C_1$–$C_6$-alkyl)aminocarbonyl, N-($C_3$–$C_6$-alkynyl)-N-($C_1$–$C_6$-alkyl)aminocarbonyl, N-($C_1$–$C_6$-alkoxy)-N-($C_1$–$C_6$-alkyl)aminocarbonyl, N,N-di($C_1$–$C_6$-alkyl)aminothiocarbonyl, $C_1$–$C_6$-alkoxyimino-$C_1$–$C_6$-alkyl, it being possible for the abovementioned alkyl, alkoxy and cycloalkyl radicals to be partially or fully halogenated and/or to have attached to them one, two or three substituents selected from amongst cyano, $C_1$–$C_4$-alkoxy, $C_1$–$C_4$-alkylthio, di($C_1$–$C_4$-alkyl)amino, $C_1$–$C_4$-alkylcarbonyl, $C_1$–$C_4$-alkoxycarbonyl, $C_1$–$C_4$-alkoxy-$C_1$–$C_4$-alkoxycarbonyl, $C_1$–$C_4$-alkylaminocarbonyl, N,N-di($C_1$–$C_4$-alkyl)aminocarbonyl or $C_3$–$C_6$-cycloalkyl; phenyl, phenyl-$C_1$–$C_6$-alkyl, phenylcarbonyl-$C_1$–$C_6$-alkyl, phenylcarbonyl, phenoxycarbonyl, phenoxythiocarbonyl, heterocyclyl, heterocyclyl-$C_1$–$C_6$-alkyl, heterocyclylcarbonyl-$C_1$–$C_6$-alkyl, heterocyclylcarbonyl, heterocyclyloxycarbonyl, heterocyclyloxythiocarbonyl, it being possible for the phenyl or heterocyclyl radical of the abovementioned radicals to be partially or fully halogenated and/or to have attached to it one, two or three substituents selected from amongst nitro, cyano, $C_1$–$C_4$-alkyl, $C_1$–$C_4$-haloalkyl, $C_1$–$C_4$-alkoxy or $C_1$–$C_4$-haloalkoxy;

$R^{20}$ is $C_1$–$C_6$-alkyl, $C_3$–$C_6$-alkenyl, $C_3$–$C_6$-haloalkenyl, $C_3$–$C_6$-alkynyl or $C_3$–$C_6$-cycloalkyl, it being possible for the abovementioned alkyl and cycloalkyl radicals to be partially or fully halogenated and/or to have attached to them one, two or three substituents selected from amongst cyano, $C_1$–$C_4$-alkoxy, $C_1$–$C_4$-alkylthio, di($C_1$–$C_4$-alkyl)amino, $C_1$–$C_4$-alkylcarbonyl, $C_1$–$C_4$-alkoxycarbonyl, $C_1$–$C_4$-alkoxy-$C_1$–$C_4$-alkoxycarbonyl, $C_1$–$C_4$-alkylaminocarbonyl, N,N-di($C_1$–$C_4$-alkyl)aminocarbonyl or $C_3$–$C_6$-cycloalkyl; phenyl, phenyl-$C_1$–$C_6$-alkyl, phenylcarbonyl-$C_1$–$C_6$-alkyl, heterocyclyl, heterocyclyl-$C_1$–$C_6$-alkyl or heterocyclylcarbonyl-$C_1$–$C_6$-alkyl, it being possible for the phenyl or heterocyclyl radical of the abovementioned radicals to be partially or fully halogenated and/or to have attached to it one, two or three substituents selected from amongst nitro, cyano, $C_1$–$C_4$-alkyl, $C_1$–$C_4$-haloalkyl, $C_1$–$C_4$-alkoxy or $C_1$–$C_4$-haloalkoxy;

p is 2, 3 or 4;

q is 1, 2, 3, 4 or 5;

or an agriculturally useful salt thereof.

2. A 3-(4,5-dihydroisoxazol-5-yl)benzoylcyclohexenone of the formula I as claimed in claim 1, where $R^1$, $R^2$ are nitro, halogen, cyano, $C_1$–$C_6$-alkyl, $C_1$–$C_6$-haloalkyl, $C_1$–$C_6$-alkoxy, $C_1$–$C_6$-haloalkoxy, $C_1$–$C_6$-alkylthio, $C_1$–$C_6$-haloalkylthio, $C_1$–$C_6$-alkylsulfinyl, $C_1$–$C_6$-haloalkylsulfinyl, $C_1$–$C_6$-alkylsulfonyl or $C_1$–$C_6$-haloalkylsulfonyl.

3. A 3-(4,5-dihydroisoxazol-5-yl)benzoylcyclohexenone of the formula I as claimed in claim 1, where $R^3$ is hydrogen.

4. A 3-(4,5-dihydroisoxazol-5-yl)benzoylcyclohexenone of the formula I as claimed in claim 1, where $R^5$ is hydrogen, halogen, cyano, nitro, $C_1$–$C_4$-alkyl, ($C_1$–$C_4$-alkoxy-$C_1$–$C_4$-alkyl, $C_1$–$C_4$-alkoxycarbonyl-$C_1$–$C_4$-alkyl, $C_1$–$C_4$-alkylthio-$C_1$–$C_4$-alkyl, $C_1$–$C_4$-haloalkyl, $C_1$–$C_4$-cyanoalkyl, $C_3$–$C_8$-CYCloalkyl, $C_1$–$C_4$-alkoxy, $C_1$–$C_4$-alkoxy-$C_2$–$C_4$-alkoxy, $C_1$–$C_4$-haloalkoxy, $C_1$–$C_4$-alkylthio, $C_1$–$C_4$-haloalkylthio, di($C_1$–$C_1$–$C_4$-alkyl)amino, $COR^8$, phenyl or benzyl, it being possible for the two last-mentioned substituents to be partially or fully halogenated and/or to have attached to them one to three of the following groups: nitro, cyano, $C_1$–$C_4$-alkyl, $C_1$–$C_4$-haloalkyl, $C_1$–$C_4$-alkoxy or $C_1$–$C_4$-haloalkoxy;

$R^6$ is hydrogen or $C_1$–$C_4$-alkyl.

5. A 3-(4,5-dihydroisoxazol-5-yl)benzoylcyclohexenone of the formula I as claimed in claim 1, where $R^5$ and $R^6$ are hydrogen.

6. A 3-(4,5-dihydroisoxazol-5-yl)benzoylcyclohexenone of the formula I as claimed in claim 1, where $R^{12}$ is hydroxyl, $OR^{19}$ or $SR^{19}$; and $R^{19}$ is $C_1$–$C_6$-alkyl, $C_1$–$C_{20}$-alkylcarbonyl, $C_1$–$C_6$-alkoxycarbonyl, $C_1$–$C_6$-alkylthiocarbonyl, it being possible for the alkyl and alkoxy radicals to be partially or fully halogenated and/or to have attached to them one, two or three substituents selected from amongst cyano, $C_1$–$C_4$-alkoxy, $C_1$–$C_4$-alkylthio, $C_1$–$C_4$-alkylcarbonyl, $C_1$–$C_4$-alkoxycarbonyl or $C_3$–$C_6$-cycloalkyl;

phenyl, phenyl-$C_1$–$C_4$-alkyl, phenylcarbonyl-$C_1$–$C_4$-alkyl, phenylcarbonyl, phenoxycarbonyl, heterocyclyl, heterocyclyl-$C_1$–$C_4$-alkyl, heterocyclylcarbonyl-$C_1$–$C_4$-alkyl, heterocyclyloxycarbonyl, it being possible for the phenyl or heterocyclyl radical of the abovementioned radicals to be partially or fully halogenated and/or have attached to it one, two or three substituents selected from amongst nitro, cyano, $C_1$–$C_4$-alkyl, $C_1$–$C_4$-haloalkyl, $C_1$–$C_4$-alkoxy or $C_1$–$C_4$-haloalkoxy.

7. A 3-(4,5-dihydroisoxazol-5-yl)benzoylcyclohexenone of the formula I as claimed in claim 1, where $R^{12}$ is hydroxyl.

8. A 3-(4,5-dihydroisoxazol-5-yl)benzoylcyclohexenone of the formula I as claimed in claim 1, where $R^{13}$ and $R^{17}$ independently of one another are hydrogen, $C_1$–$C_4$-alkyl or $C_1$–$C_4$-alkylthio;

$R^{14}$, $R^{16}$, $R^{18}$ independently of one another are hydrogen or methyl;

$R^{15}$ is hydrogen, hydroxyl, $C_1$–$C_6$-alkyl or di($C_1$–$C_6$-alkoxy)methyl; or $R^{13}$ and $R^{14}$ or $R^{14}$ and $R^{15}$ or $R^{15}$ and $R^{18}$ or $R^{14}$ and $R^{18}$ or $R^{17}$ and $R^{18}$ together are $C_1$–$C_5$-alkanediyl which can have attached to it one, two or three substituents selected from amongst halogen, cyano, $C_1$–$C_4$-alkyl, $C_1$–$C_4$-haloalkyl or $C_1$–$C_4$-alkoxycarbonyl; or $R^{15}$ and $R^{16}$ together are an oxygen atom.

9. A process for the preparation of a 3-(4,5-dihydroisoxazol-5-yl)benzoylcyclohexenone of the formula I as claimed in claim 1, which comprises acylating the cyclohexenone of the formula II where $R^{12}$=OH, where the variables $R^{13}$ to $R^{18}$ have the meanings stated in claim 1,

II

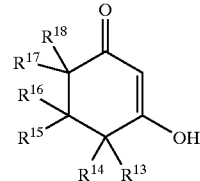

(where $R^{12}$ = OH)

with an activated carboxylic acid IIIα or with a carboxylic acid IIIβ,

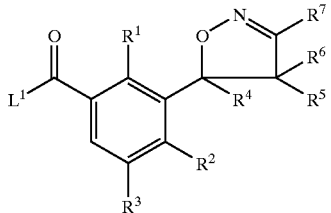
IIIα

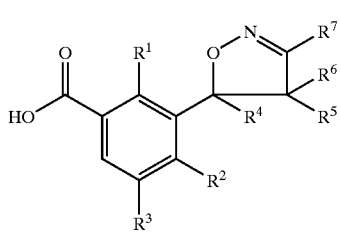
IIIβ where the variables $R^1$ to $R^7$ have the meanings stated in claim 1 and $L^1$ is a nucleophilically displaceable leaving group, and subjecting the acylation product to a rearrangement reaction in the presence of a catalyst to give the compounds I (where $R^{12}$=OH).

10. A process for the preparation of a 3-(4,5-dihydroisoxazol-5-yl)benzoylcyclohexenone of the formula I where $R^{12}$=$OR^{19}$ or $SR^{19}$ as claimed in claim 1, in which a compound of the formula I where $R^{12}$=OH or SH,

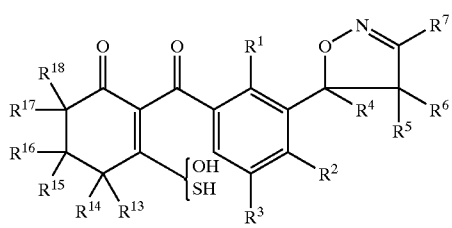

where $R^{12}$ = OH, SH where $R^1$ to $R^7$ and $R^{13}$ to $R^{18}$ have the meaning stated in claim 1 is reacted with a compound of the formula V $$L^2—R^{19} \qquad V$$

where the variable $R^{19}$ has the meaning stated in claim 1 and $L^2$ is a nucleophilically displaceable leaving group.

11. A process for the preparation of a 3-(4,5-dihydroisoxazol-5-yl)benzoylcyclohexenone of the formula I where $R^{12}$=halogen as claimed in claim 1, in which a compound of the formula I where $R^{12}$=OH,

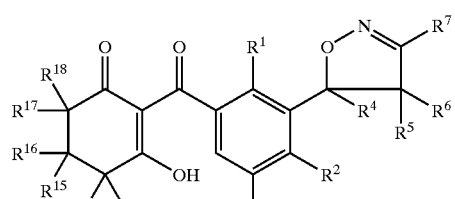

where $R^{12}$ = OH where the variables $R^1$ to $R^7$ and $R^{13}$ to $R^{18}$ have the meaning stated in claim 1 is reacted with a halogenating agent.

12. A process for the preparation of a 3-(4,5-dihydroisoxazol-5-yl)benzoylcyclohexenone of the formula I where $R^{12}$=mercapto, $OR^{19}$ or $SR^{19}$ as claimed in claim 1, in which a compound of the formula I where $R^{12}$=halogen,

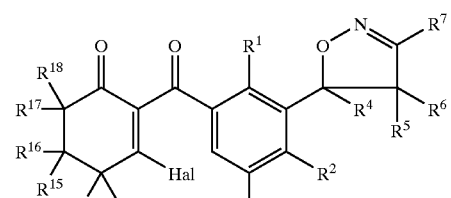

where $R^{12}$ = Hal where the variables $R^1$ to $R^7$ and $R^{13}$ to $R^{18}$ have the meaning stated in claim 1 is reacted with a compound of the formula VI $$H_2S \text{ or } HOR^{19} \text{ or } HSR^{19} \qquad VI$$

where $R^{19}$ has the meaning stated in claim 1, in the presence or absence of a base.

13. A process for the preparation of a 3-(4,5-dihydroisoxazol-5-yl)benzoylcyclohexenone of the formula I where $R^{12}$=$SOR^{20}$ or $SO_2R^{20}$ as claimed in claim 1, in which a compound of the formula I where $R^{12}$=$SR^{20}$,

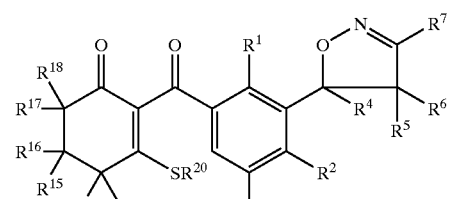

where $R^{12}$ = $SR^{14}$ where the variables $R^1$ to $R^7$ and $R^{13}$ to $R^{18}$ have the meaning stated in claim 1, is reacted with an oxidant.

14. A composition comprising a herbicidally active amount of at least one 3-(4,5-dihydroisoxazol-5-yl)benzoylcyclohexenone of the formula I or of an agriculturally useful salt thereof as claimed in claim 1 and adjuvants conventionally used for the formulation of crop protection products.

15. A process for the preparation of a composition as claimed in claim 14, which comprises mixing a herbicidally active amount of at least one 3-(4,5-dihydroisoxazol-5-yl)benzoylcyclo-hexenone of the formula I or of an agriculturally useful salt of I and adjuvants conventionally used for the formulation of crop protection products.

16. A method of controlling undesired vegetation, which comprises allowing a herbicidally active amount of at least one 3-(4,5-dihydroisoxazol-5-yl)benzoylcyclohexenone of the formula I or of an agriculturally useful salt thereof as claimed in claim 1 to act on plants, their environment and/or on seeds.

* * * * *

UNITED STATES PATENT AND TRADEMARK OFFICE
CERTIFICATE OF CORRECTION

PATENT NO.    : 6,645,919 B1
DATED         : November 11, 2003
INVENTOR(S)   : Baumann et al.

It is certified that error appears in the above-identified patent and that said Letters Patent is hereby corrected as shown below:

<u>Column 89,</u>
Line 61, "$C_3$-$C_8$-CYCloalkyl" should be -- $C_3$-$C_8$-cycloalkyl --;
Line 64, "di($C_1$-$C_1$-$C_4$-alkyl)amino" should be -- di($C_1$-$C_4$-alkyl)amino --.

Signed and Sealed this

Thirtieth Day of December, 2003

JAMES E. ROGAN
*Director of the United States Patent and Trademark Office*